United States Patent
Menn et al.

(10) Patent No.: US 10,792,041 B2
(45) Date of Patent: Oct. 6, 2020

(54) DEVICES AND METHODS FOR APPLYING SURGICAL CLIPS

(71) Applicant: CONMED Corporation, Utica, NY (US)

(72) Inventors: Pavel Menn, Marblehead, MA (US); Nathaniel Rosso, Brookline, MA (US)

(73) Assignee: CONMED Corporation, Utica, NY (US)

( * ) Notice: Subject to any disclaimer, the term of this patent is extended or adjusted under 35 U.S.C. 154(b) by 1051 days.

(21) Appl. No.: 14/593,481

(22) Filed: Jan. 9, 2015

(65) Prior Publication Data

US 2015/0196298 A1    Jul. 16, 2015

Related U.S. Application Data

(60) Provisional application No. 61/970,680, filed on Mar. 26, 2014, provisional application No. 61/926,251, filed on Jan. 10, 2014.

(51) Int. Cl.
*A61B 17/10* (2006.01)
*A61B 17/128* (2006.01)
(Continued)

(52) U.S. Cl.
CPC ........ *A61B 17/105* (2013.01); *A61B 17/1285* (2013.01); *A61B 17/122* (2013.01);
(Continued)

(58) Field of Classification Search
CPC ..... A61B 17/10; A61B 17/105; A61B 17/128; A61B 17/1285; A61B 17/07207; A61B 2017/00407; A61B 2017/00473; A61B 17/2909; A61B 17/0487; A61B 17/072; A61B 17/0682; A61B 17/0684; A61B 17/08; A61B 17/083; A61B 2017/291;
(Continued)

(56) References Cited

U.S. PATENT DOCUMENTS 5,171,247 A * 12/1992 Hughett ............ A61B 17/1285
606/142
5,607,436 A * 3/1997 Pratt .................. A61B 17/1285
227/901

(Continued)

*Primary Examiner* — Katherine H Schwiker
(74) *Attorney, Agent, or Firm* — Bond, Schoeneck & King, PLLC; Frederick J. M. Price

(57) ABSTRACT

An actuator is movable between a first position and a second position to move a drive mechanism between a first configuration and a second configuration relative to a housing. A cartridge assembly configured to be removably coupled to the housing to couple such that the cartridge assembly is coupled to the drive mechanism. A first member of the drive mechanism moves a first member of the cartridge assembly to advance a surgical clip of the cartridge assembly in a distal direction when the drive mechanism is placed in the first configuration. A second member of the drive mechanism moves a second member of the cartridge assembly relative to the clamp mechanism when the drive mechanism is placed in the second configuration to transition the clamp mechanism from a first configuration to a second configuration. The clamp mechanism is configured to clamp the surgical clip when in the second configuration.

20 Claims, 48 Drawing Sheets

FIG. 33

(51) Int. Cl.
*A61B 17/29* (2006.01)
*A61B 17/00* (2006.01)
*A61B 17/122* (2006.01)

(52) U.S. Cl.
CPC .............. *A61B 2017/0046* (2013.01); *A61B 2017/00407* (2013.01); *A61B 2017/291* (2013.01); *A61B 2017/2923* (2013.01); *A61B 2560/02* (2013.01)

(58) Field of Classification Search
CPC .... A61B 2017/2912; A61B 2017/2913; A61B 2017/2915; A61B 2017/2917; A61B 2017/2919; A61B 2017/292; A61B 2017/2922; A61B 2017/2923; A61B 2017/2924; A61B 2017/2925; A61B 2017/2931; A61B 2017/2932; A61B 2017/2933; A61B 2017/2934; A61B 2017/2936; A61B 2017/2937; A61B 2017/2938; A61B 2017/2939; A61B 2017/294; A61B 2017/2941; A61B 2017/2943; A61B 2017/2944; A61B 2017/2947; A61B 2017/2946; A61B 2017/0488; A61B 2017/049; A61B 2017/0688; A61B 2017/081; A61B 2017/088
USPC ................................................ 606/142–143
See application file for complete search history.

(56) References Cited

U.S. PATENT DOCUMENTS

| | | | |
|---|---|---|---|
| 5,766,184 A * | 6/1998 | Matsuno | A61B 90/94 606/142 |
| RE36,720 E * | 5/2000 | Green | A61B 17/122 227/19 |
| 6,099,537 A | 8/2000 | Sugai et al. | |
| 2005/0171560 A1* | 8/2005 | Hughett | A61B 17/10 606/142 |
| 2009/0228024 A1* | 9/2009 | Whitfield | A61B 17/1285 606/143 |
| 2013/0172911 A1* | 7/2013 | Rockrohr | A61B 17/064 606/143 |
| 2016/0296232 A1* | 10/2016 | Campbell | A61B 17/1285 |

* cited by examiner

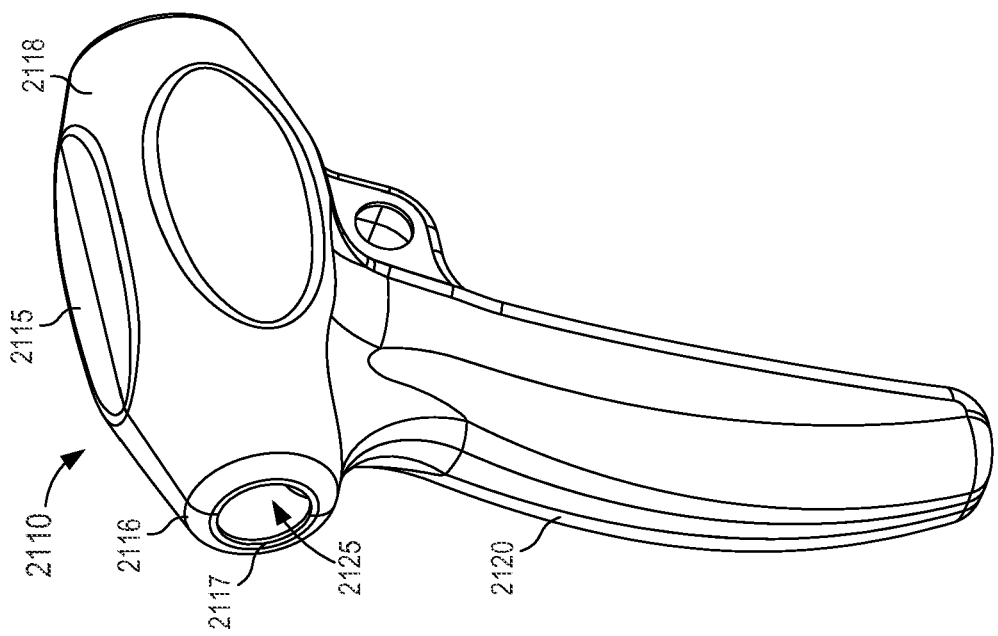
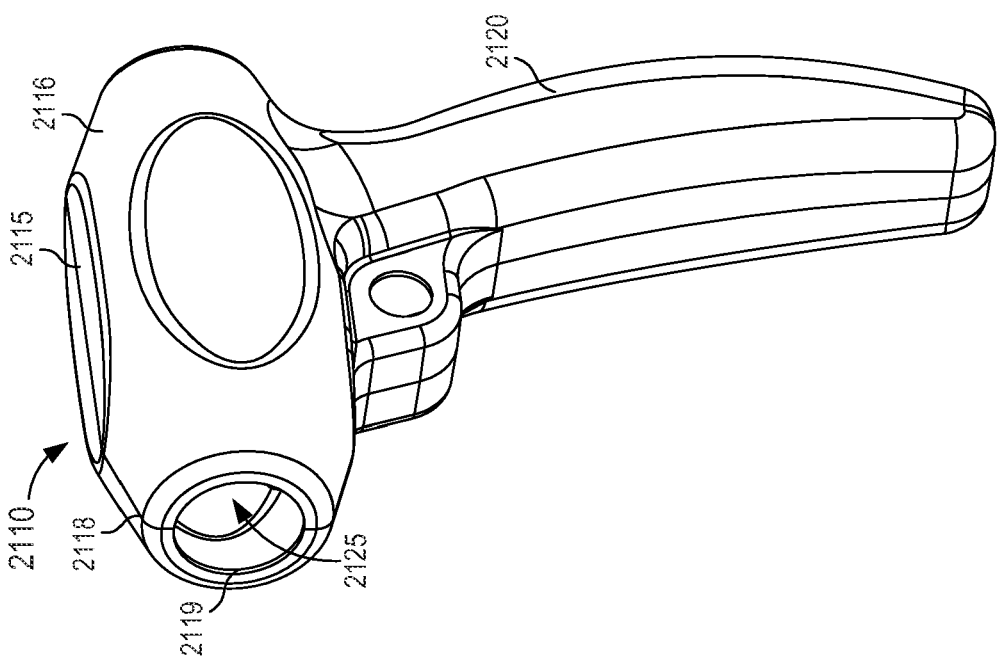

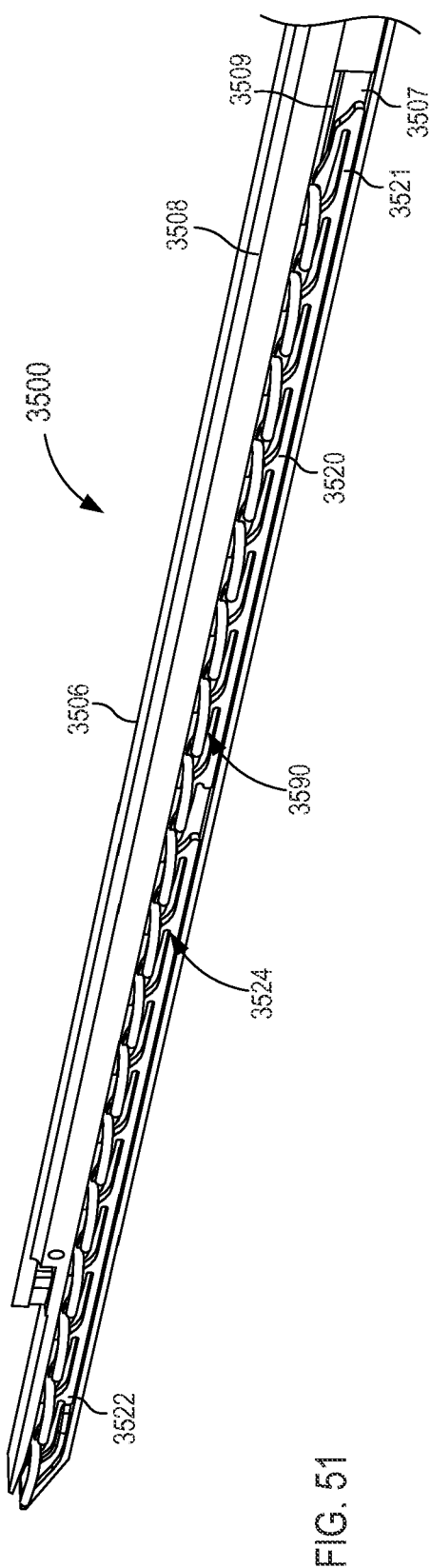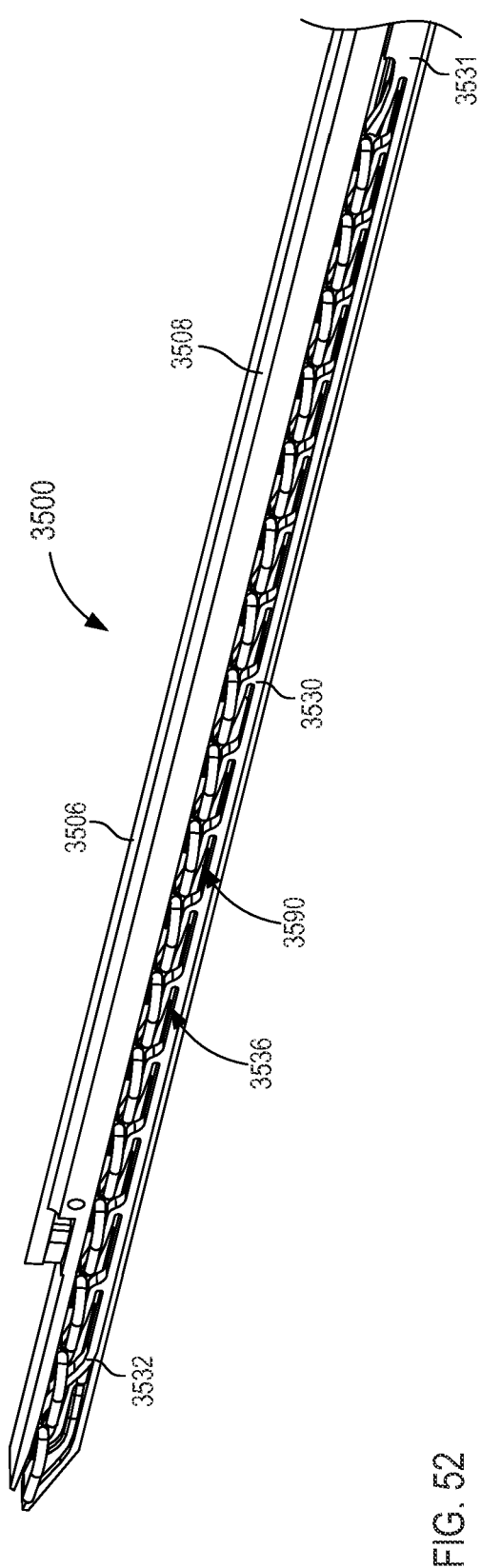

DEVICES AND METHODS FOR APPLYING SURGICAL CLIPS

CROSS-REFERENCE TO RELATED APPLICATIONS

This application claims priority to and the benefit of U.S. Provisional Patent Application Ser. Nos. 61/926,251 entitled, "Universal Reposable Platform for a Five MM Tip-first Surgical Clip Applier," filed Jan. 10, 2014, and 61/970,680 entitled, "Devices and Methods for Applying Surgical Clips," filed Mar. 26, 2014, the disclosures of which are incorporated herein by reference in their entireties.

BACKGROUND

The embodiments described herein relate generally to devices methods used, for example, in laparoscopic and/or endoscopic procedures and, more particularly, to a universal reposable device for applying surgical clips and methods of using the same.

In general, laparoscopic and endoscopic surgical procedures include inserting a relatively long and narrow disposable tubular shaft (e.g., a catheter) through a small incision or natural body orifice. In some known instances, at least a portion of a surgical clip device is inserted through and/or is otherwise included in such tubular shaft, which can be manipulated by a surgeon or the like to apply surgical clips to a target location or tissue within the body. For example, surgical clips are often used to ligate or occlude blood vessels in laparoscopic or endoscopic surgical procedures. Typically, the surgical clips are securely clamped about a blood vessel to completely occlude that blood vessel during the surgical procedure. In some instances, however, the relatively small size of the opening in the body and/or the relatively small size of the tubular shaft or any other portion of the surgical clip applier can result in difficulty in placing the surgical clips about a desired vascular structure. Moreover, in some instances, the size of the opening in the body and/or the diameter of the tubular shaft inserted therethrough can, at least partially, limit and/or otherwise determine the size of the blood vessels that can be occluded. For example, a tubular shaft with a relatively smaller diameter can occlude vessels in difficult to reach locations, however, the smaller diameter of the tubular shaft limits the overall width of the surgical clips that are included in and/or that otherwise can pass through the tubular shaft. As a result, the limited size of the surgical clips, in turn, limits the size and/or diameter of the blood vessels about which the surgical clips can be applied. In some instances, failure to securely clamp the surgical clips about the target blood vessels can result in, for example, damage to nearby tissue, interference with the surgical site, loss of the clip inside the patient, patient blood loss, and/or a potentially lethal drop in blood pressure.

Thus, a need exists for improved apparatus and methods for applying surgical clips to a target vascular structure.

SUMMARY

Apparatus and methods of a using a universal reposable device for applying surgical clips to a target vascular structure are described herein. In some embodiments, an apparatus includes a housing, a drive mechanism, an actuator, and a cartridge assembly. The drive mechanism being movably disposed in the housing and including a first member and a second member. The actuator is operably coupled to the drive mechanism. The actuator is movable between a first position relative to the housing and a second position relative to the housing to move the drive mechanism between a first configuration and a second configuration. The cartridge assembly is removably coupled to the housing. The cartridge assembly includes a first member, a second member, and a clamp mechanism. The first member of the cartridge assembly is removably coupled to the first member of the drive mechanism such that when the drive mechanism is placed in the first configuration, the first member of the cartridge assembly is moved relative to the clamp mechanism to advance a surgical clip included in the cartridge assembly in a distal direction. The second member of the cartridge assembly removably coupled to the second member such that when the drive mechanism is placed in the second configuration, the second member of the cartridge assembly is moved relative to the clamp mechanism. The clamp mechanism is transitioned from a first configuration to a second configuration when the second member of the cartridge assembly is moved relative to the clamp mechanism. The clamp mechanism is configured to clamp the surgical clip when in the second configuration.

BRIEF DESCRIPTION OF THE DRAWINGS

FIGS. 5 and 6 are a front perspective view and a rear perspective view of a housing included in the universal handle of FIG. 3.

FIG. 51 is a perspective view of a portion of the cartridge assembly of FIG. 48.

FIG. 52 is a perspective view of a portion of the cartridge assembly of FIG. 48.

DETAILED DESCRIPTION

Figure 1:
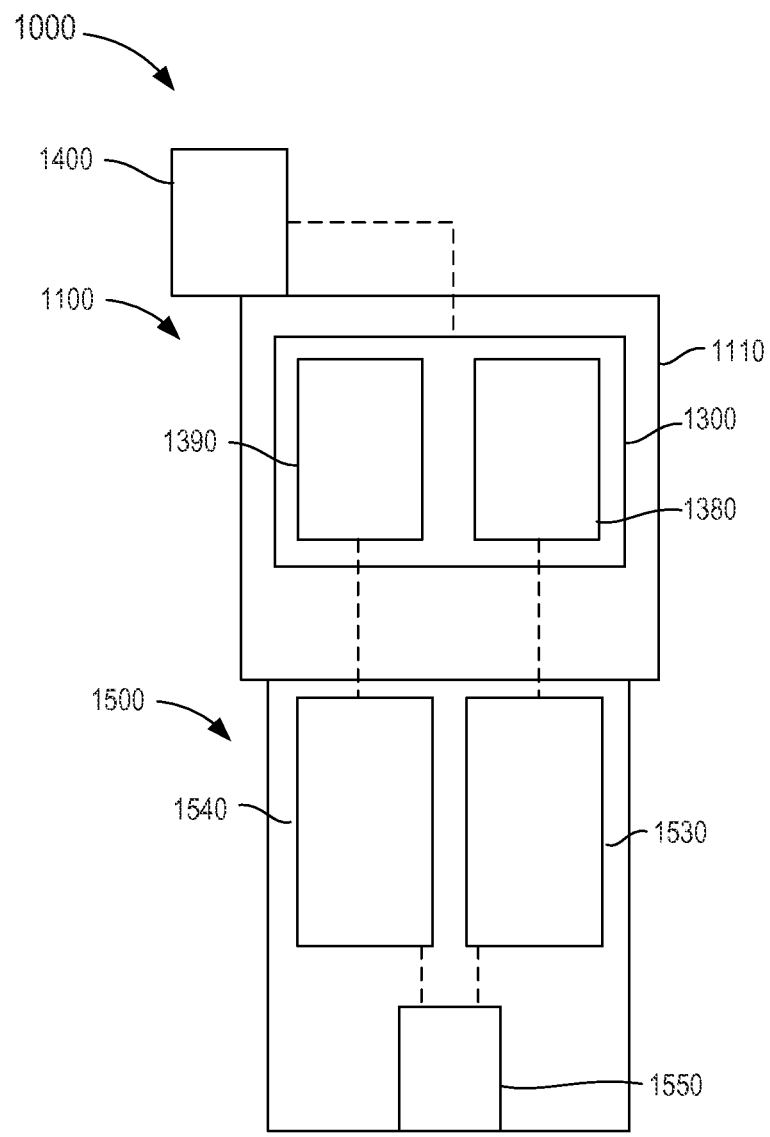
FIG. 1 is schematic illustration of a reposable device for applying surgical clips to a target tissue according to an embodiment.

In some embodiments, an apparatus includes a housing, a drive mechanism, an actuator, and a cartridge assembly. The drive mechanism being movably disposed in the housing and including a first member and a second member. The actuator is operably coupled to the drive mechanism. The actuator is movable between a first position relative to the housing and a second position relative to the housing to move the drive mechanism between a first configuration and a second configuration. The cartridge assembly is removably coupled to the housing. The cartridge assembly includes a first member, a second member, and a clamp mechanism. The first member of the cartridge assembly is removably coupled to the first member of the drive mechanism such that when the drive mechanism is placed in the first configuration, the first member of the cartridge assembly is moved relative to the clamp mechanism to advance a surgical clip included in the cartridge assembly in a distal direction. The second member of the cartridge assembly is removably coupled to the second member such that when the drive mechanism is placed in the second configuration, the second member of the cartridge assembly is moved relative to the clamp mechanism. The clamp mechanism is transitioned from a first configuration to a second configuration when the second member of the cartridge assembly is moved relative to the clamp mechanism. The clamp mechanism is configured to clamp the surgical clip when in the second configuration.

In some embodiments, an apparatus includes a housing, a drive mechanism, a lock mechanism, and a cartridge assembly. The drive mechanism being movably disposed in the housing and including a first member and a second member. The lock mechanism is coupled to the housing such that a portion of the first member of the drive mechanism and a portion of the second member of the drive mechanism extend into an inner volume defined by the lock mechanism. The lock mechanism includes a lock actuator configured to be transitioned between a first configuration and a second configuration. A portion of the cartridge assembly is configured to be inserted into the inner volume of the lock mechanism when the cartridge assembly is in a first orientation relative to the lock mechanism and the lock actuator is in the first configuration. The cartridge assembly is moved to a second orientation relative to the lock mechanism when the portion of the cartridge assembly is disposed in the inner volume such that a first member of the cartridge assembly is removably coupled to the first member of the drive mechanism and a second member of the cartridge assembly is removably coupled to the second member of the drive mechanism. The lock actuator is configured to be moved to the second configuration to at least temporarily maintain the cartridge assembly in the second orientation.

In some embodiments, an apparatus includes a drive mechanism disposed in a housing and movable between a first configuration and a second configuration. The drive mechanism includes a first member and a second member. The first member of the drive mechanism is configured to be moved between a first axial position and a second axial position relative to the drive mechanism. The second member of the drive mechanism is configured to be moved between the first axial position and the second axial position, at least a portion of the movement of the first member being independent of at least a portion of the movement of the second member. A cartridge assembly is removably couplable to the housing. The cartridge assembly includes a first member and a second member. The first member of the cartridge assembly is in contact with the first member of the drive mechanism when the cartridge assembly is coupled to the housing such that movement of the first member of the drive mechanism moves the first member of the cartridge assembly from a first axial position relative to the cartridge assembly to a second axial position relative to the cartridge assembly. The second member of the cartridge assembly is selectively placed in contact with the second member of the drive mechanism when the cartridge assembly is coupled to the housing.

As used in this specification and the appended claims, the singular forms "a," "an," and "the" include plural referents unless the context clearly dictates otherwise. Thus, for example, the term "a member" is intended to mean a single member or a combination of members, "a material" is intended to mean one or more materials, or a combination thereof.

As used herein, the term "set" can refer to multiple features or a singular feature with multiple parts. For example, when referring to a set of walls, the set of walls can be considered as one wall with multiple portions, or the set of walls can be considered as multiple, distinct walls. Thus, a monolithically constructed item can include a set of walls. Such a set of walls may include multiple portions that are either continuous or discontinuous from each other. A set of walls can also be fabricated from multiple items that are produced separately and are later joined together (e.g., via a weld, an adhesive, or any suitable method).

As used herein, the words "proximal" and "distal" refer to a direction closer to and away from, respectively, an operator of, for example, a medical device. Thus, for example, the end of the medical device contacting the patient's body would be the distal end of the medical device, while the end opposite the distal end would be the proximal end of the medical device.

The embodiments described herein can be formed or constructed of one or more biocompatible materials. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes, and/or blends and copolymers thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof.

FIG. 1 is a schematic illustration of a reposable device 1000 according to an embodiment. The reposable device 1000 can be used, for example, during laparoscopic surgical procedures, endoscopic surgical procedures, and/or the like to apply surgical clips to a target tissue. More specifically, in some instances, the reposable device 1000 can be used to apply surgical clips having a desired size and/or configuration to target vascular structures such as, for example, blood vessels and/or the like to ligate, occlude, and/or otherwise clamp the target vascular structures. As described in further detail herein, the reposable device 1000 (also referred to herein as "device") includes a reusable universal handle 1100 that can be removably coupled to and configured to manipulate a disposable cartridge assembly 1500.

The reusable universal handle 1100 (also referred to herein as "handle") includes a housing 1110, a drive mechanism 1300, and an actuator 1400. The housing 1110 can be any suitable shape, size, and/or configuration, as described below with respect to specific embodiments. In some embodiments, the housing 1110 can be configured to house and/or otherwise enclose at least a portion of the drive mechanism 1300 and the actuator 1400. For example, the housing 1110 can define an inner volume within which at least a portion of the drive mechanism 1300 and/or at least a portion of the actuator 1400 can be disposed.

As shown in FIG. 1, the drive mechanism 1300 includes a first member 1380 and a second member 1390. The drive mechanism 1300 can be any suitable shape, size, and/or configuration. For example, in some embodiments, at least a portion of the drive mechanism 1300 can be substantially cylindrical and can have a size that substantially corresponds to a portion of the housing 1110 and/or the inner volume defined thereby. As described above, at least a portion of the drive mechanism 1300 is disposed within the housing 1110. Expanding further, at least a portion of the drive mechanism 1300 can be disposed in the housing 1110 and can be moved between a first configuration and a second configuration. For example, in some embodiments, the drive mechanism 1300 can be moved in a substantially axial direction between the first configuration, associated with a proximal position of at least a portion of the drive mechanism 1300 relative to the housing 1110, and the second configuration, associated with a distal position of at least a portion of the drive mechanism 1300 relative to the housing 1110.

The first member 1380 and the second member 1390 of the drive mechanism 1300 can be any suitable shape, size, and/or configuration. For example, in some embodiments, the arrangement of the drive mechanism 1300 can be such that the first member 1380 and the second member 1390 are disposed adjacent to one another within the housing 1110. Moreover, the arrangement of the drive mechanism 1300 can be such that at least a portion of the first member 1380 and at least a portion of the second member 1390 extend substantially outside of the housing 1110, as described in further detail herein. In some embodiments, the drive mechanism 1300 can be moved between the first configuration and the second configuration to move the first member 1380 and/or the second member 1390 in an axial direction between a proximal position and a distal position relative to the housing 1110. Expanding further, the drive mechanism 1300 can be configured such that the movement of the first member 1380 is at least partially independent of the movement of the second member 1390. For example, in some embodiments, the first member 1380 can be moved relative to the second member 1390 during, for example, a first portion of the movement between its first position and its second position, and the first member 1380 can be moved substantially concurrently with the second member 1390 during, for example, a second portion of the movement between its first position and its second position, as described in further detail herein.

The actuator 1400 of the handle 1100 is coupled to the housing 1110 and is configured to be moved between a first configuration and a second configuration. For example, in some embodiments, the actuator 1400 can be rotatably coupled to a portion of the housing 1110, which in turn, can form and/or define an axis about which at least a portion of the actuator 1400 can pivot and/or rotate. For example, in some embodiments, a portion of the housing 1110 and a portion of the actuator 1400 can form a trigger-style configuration, in which the actuator 1400 can be pivoted relative to the portion of the housing 1110 to move the portion of the actuator 1400 between a first position and a second position (e.g., a first angular position and a second angular position and/or the like).

As shown in FIG. 1, the actuator 1400 is operably coupled to the drive mechanism 1300 such that movement of the actuator 1400 between its first configuration and its second configuration moves the drive mechanism between its first configuration and its second configuration. For example, in some embodiments, the actuator 1400 can include a portion such as, for example, a cam and/or the like that can engage a portion of the drive mechanism 1300 such as, for example, a shuttle and/or the like. In this manner, the portion of the actuator 1400 and the portion of the drive mechanism 1300 can form a kinematic linkage or the like that can convert a substantially rotational movement of the actuator 1300 to a substantially linear (e.g., axial) movement of the drive mechanism 1300, as described in detail below with respect to specific embodiments. In other embodiments, the actuator 1400 can be configured to be moved in a substantially linear motion, which in turn, can move the drive mechanism 1300 in a substantially linear manner.

The cartridge assembly 1500 can be any suitable shape, size, and/or configuration. For example, in some embodiments, at least a portion of the cartridge assembly 1500 can be a substantially cylindrical tube or the like such as, for example, a cannula, a catheter, and/or the like. In this manner, the cartridge assembly 1500 can include a set of surgical clips (not shown in FIG. 1) that are disposed in the substantially cylindrical tube. More specifically, in some embodiments, the set of surgical clips can be linearly disposed in the substantially cylindrical tube and arranged with a substantially uniform spacing. In some embodiments, the cartridge assembly 1500 can be configured to include, for example, a set of 5 millimeter (mm) and/or 10 mm surgical clips. In other embodiments, the cartridge assembly 1500 can include a set of surgical clips having any suitable size.

As described above, the cartridge assembly 1500 is configured to be removably coupled to a portion of the housing 1110. For example, in some embodiments, a proximal end portion of the cartridge assembly 1500 can include an adapter or the like that can be at least partially inserted into the inner volume of the housing 1110 to couple the cartridge assembly 1500 thereto. In some embodiments, the housing 1110 can include a portion, device, and/or mechanism that is configured to engage a portion of the cartridge assembly 1500 to retain the cartridge assembly 1500 in a relatively fixed position relative to the housing 1110. Expanding further, in some such embodiments, the cartridge assembly 1500 can be in a first orientation when inserted into the inner volume of the housing 1110 and can be rotated to a second orientation, in which the portion, device, and/or mechanism of the housing 1110 engages the cartridge assembly 1500 to retain the cartridge assembly 1500 in its second orientation.

As shown in FIG. 1, the cartridge assembly 1500 includes a first member 1530, a second member 1540, and a clamp mechanism 1550. The arrangement of the cartridge assembly 1500 can be such that when the cartridge assembly 1500 is coupled to the housing 1110, the first member 1530 and the second member 1540 of the cartridge assembly 1500 are removably coupled to the first member 1380 and the second member 1390, respectively, of the drive mechanism 1300. As such, the first member 1380 of the drive mechanism 1300 can be configured to move the first member 1530 of the cartridge assembly 1500, and the second member 1390 of the drive mechanism 1300 can be configured to move the second member 1540 of the cartridge assembly 1500, as described in further detail herein. More specifically, at least a portion of the first member 1530 can be disposed in the substantially cylindrical tube of the cartridge assembly 1500 and can be moved relative to the substantially cylindrical tube to advance the set of surgical clips disposed therein in the distal direction. In a similar manner, at least a portion of the second member 1540 can be disposed in the substantially cylindrical tube of the cartridge assembly 1500 and can be moved relative to the substantially cylindrical tube to transition the clamp mechanism 1550 between a first configuration and a second configuration, as described in further detail herein.

The clamp mechanism 1550 can be any suitable shape, size, and/or configuration. For example, in some embodiments, the clamp mechanism 1550 can include a first arm and a second arm that can be transitioned between a substantially open configuration to a substantially closed configuration. More specifically, in some embodiments, the clamp mechanism 1550 can include a portion, mechanism, and/or member that can be in contact with, for example, a distal end portion of the second member 1540 such that movement of the second member 1540 in the distal direction advances the portion, mechanism, and/or member relative to the first arm and the second arm of the clamp mechanism 1550 to transition the first arm and the second arm from substantially open configuration to the substantially closed configuration. In this manner, the clamp mechanism 1550 can be transitioned between a first configuration and a second configuration to clamp, pinch, close, and/or otherwise close a surgical clip (e.g., a surgical clip disposed between the first arm and the second arm of the clamp mechanism 1550), as described below with respect to specific embodiments.

In use, a user (e.g., a surgeon, a doctor, a physician, a technician, etc.) can engage the handle 1100 and the cartridge assembly 1500 to removably couple the cartridge assembly 1500 to the handle 1100. As described above, in some instances, the user can place the cartridge assembly 1500 in a first orientation and while in the first configuration, can insert a portion of the cartridge assembly 1500 into the inner volume of the housing 1110 to, for example, place the device 1000 in a first configuration. With the portion of the cartridge assembly 1500 disposed in the housing 1110, the user can, for example, rotate the cartridge assembly 1500 to its second orientation to removably couple the cartridge assembly 1500 to the handle 1100, thereby placing the device 1000 in a second configuration.

Once the cartridge assembly 1500 is coupled to the handle 1100, the user can manipulate the device 1000 to insert a portion of the cartridge assembly 1500 into an opening defined by a portion of the body of a patient (e.g., a body orifice or a surgical incision). Expanding further, the user can manipulate the device 1000 to position the clamp mechanism 1550 about, for example, a target vascular structure such as a blood vessel or the like. With the cartridge assembly 1500 inserted into the body of the patient, the user can manipulate the device 1000, for example, by moving the actuator 1400 relative to the housing 1100. Thus, with the actuator 1400 operably coupled to the drive mechanism 1300 (as described above), the movement of the actuator 1400 can move the drive mechanism 1300 from its first configuration to its second configuration. In this manner, the first member 1380 of the drive mechanism 1300 is moved in an axial manner from its first position towards its second position. Thus, with the first member 1380 of the drive mechanism 1300 coupled to the first member 1530 of the cartridge assembly 1500, the movement of the first member 1380 of the drive mechanism towards its second position, moves the first member 1530 of the cartridge assembly 1500 in the distal direction. Furthermore, with the first member 1530 of the cartridge assembly 1500 in contact with the set of surgical clips, the set of surgical clips are advanced relative to the substantially cylindrical tubing of the cartridge assembly 1500. More specifically, the first member 1380 of the drive mechanism 1300 and the first member 1530 of the cartridge assembly 1500 are moved to advance the surgical clips in the distal direction prior to a movement of the first member 1390 of the drive mechanism 1300. In this manner, the distal movement of the set of surgical clips can be such that a distal most surgical clip is advanced into a desired position relative to the clamp mechanism 1550. For example, in some embodiments, the distal movement of the surgical clips can be such that the distal most surgical clip is disposed between a first arm and a second arm of the clamp mechanism 1550. Moreover, with the clamp mechanism 1550 disposed about a target vascular structure, the set of surgical clips can be advanced such that the distal most surgical clip is disposed about the target vascular structure.

With the set of surgical clips advanced in the distal direction and prior to the actuator 1400 being placed in its second configuration, the movement of the actuator 1400 moves the second member 1390 of the drive mechanism 1300 from its first position towards its second position. As such, the movement of the second member 1390 of the drive mechanism 1300 moves the first member 1540 of the cartridge assembly 1500 relative to the substantially cylindrical tubing. As described above, the second member 1540 of the cartridge assembly 1500 is in contact with the clamp mechanism 1550 such that as the second member 1540 is moved relative to the substantially cylindrical housing, the clamp mechanism 1550 is transitioned from the substantially open configuration to the substantially closed configuration and as such, the clamp mechanism 1550 engages the distal most surgical clip such that the distal most surgical clip is transitioned to a substantially clamped configuration. Thus, with the distal most surgical clip disposed about the target vascular tissue, the clamp mechanism 1550 can clamp the distal most surgical clip about the target vascular tissue such that the target vascular structure is ligated and/or occluded.

In some embodiments, the actuator 1400 and/or the drive mechanism 1300 can include a bias member or the like that can be configured such that once the actuator 1400 is placed in its second configuration, the bias member can exert a force to move the actuator 1400 from its second configuration to its first configuration and the drive mechanism 1300 from its second configuration to its first configuration. Thus, the user can manipulate the device 1000 to dispose the clamp mechanism 1550 about a different target vascular structure and can further manipulate the device 1000 to clamp a surgical clip about that target vascular structure in a manner as described above.

Figure 2:
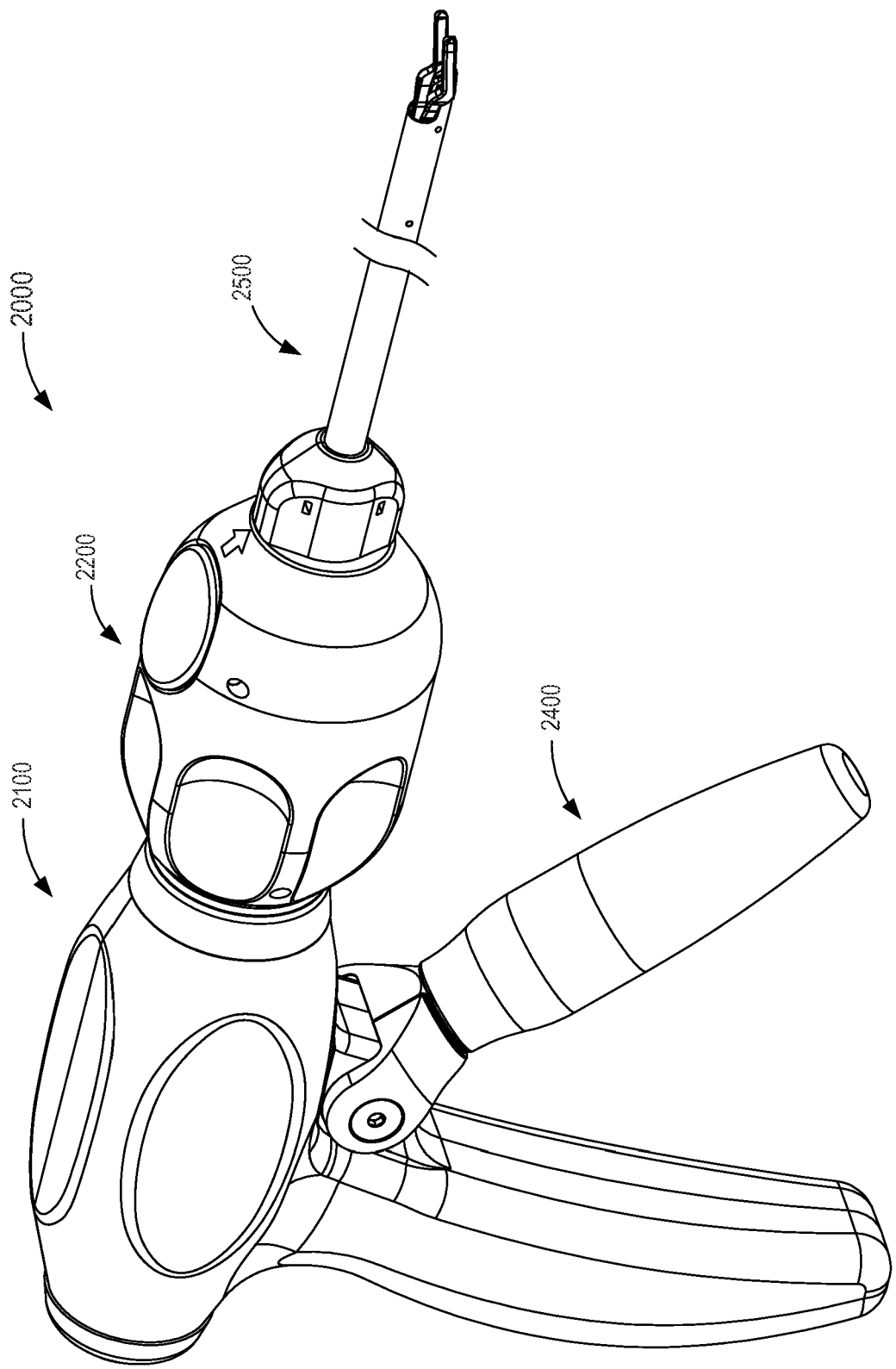
FIG. 2 is a perspective view of a reposable device for applying surgical clips to a target tissue according to an embodiment.

FIGS. 2-44 illustrate a universal reposable device 2000 according to an embodiment. The reposable device 2000 shown, for example, in FIG. 2, can be used during laparoscopic surgical procedures, endoscopic surgical procedures, and/or the like to apply surgical clips to a target tissue. More specifically, in some instances, the reposable device 2000 can be used to apply surgical clips having a desired size and/or configuration to target vascular structures such as, for example, blood vessels and/or the like to ligate, occlude, and/or otherwise clamp the target vascular structures. As described in further detail herein, the reposable device 2000 (also referred to herein as "device") includes a reusable universal handle 2100 (see e.g., FIGS. 3-18) that can be removably coupled to and configured to manipulate a disposable cartridge assembly 2500 (see e.g., FIGS. 19-30).

Figure 3:
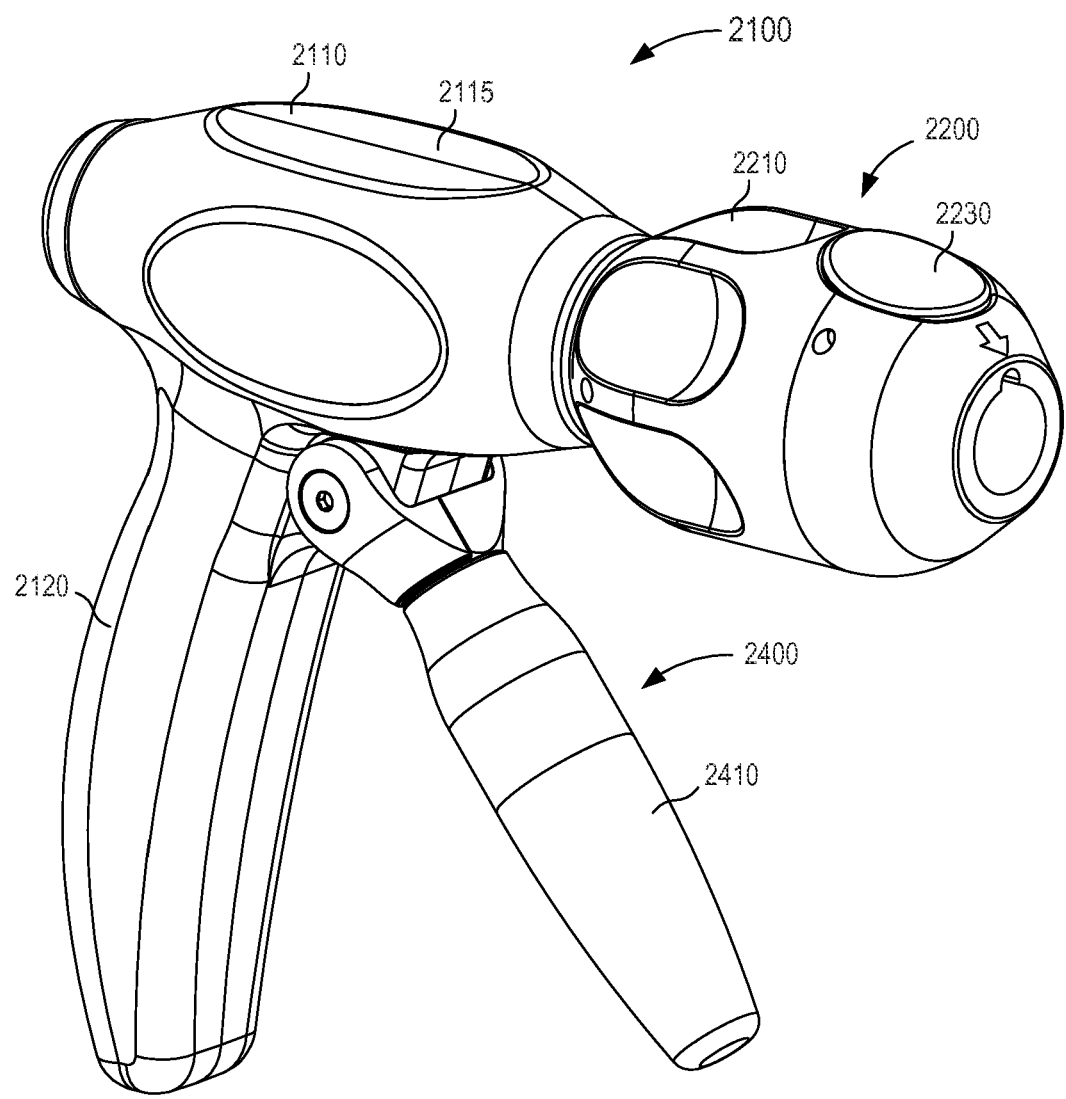
FIG. 3 is a perspective view of a universal handle included in the reposable device of FIG. 2.
Figure 4:
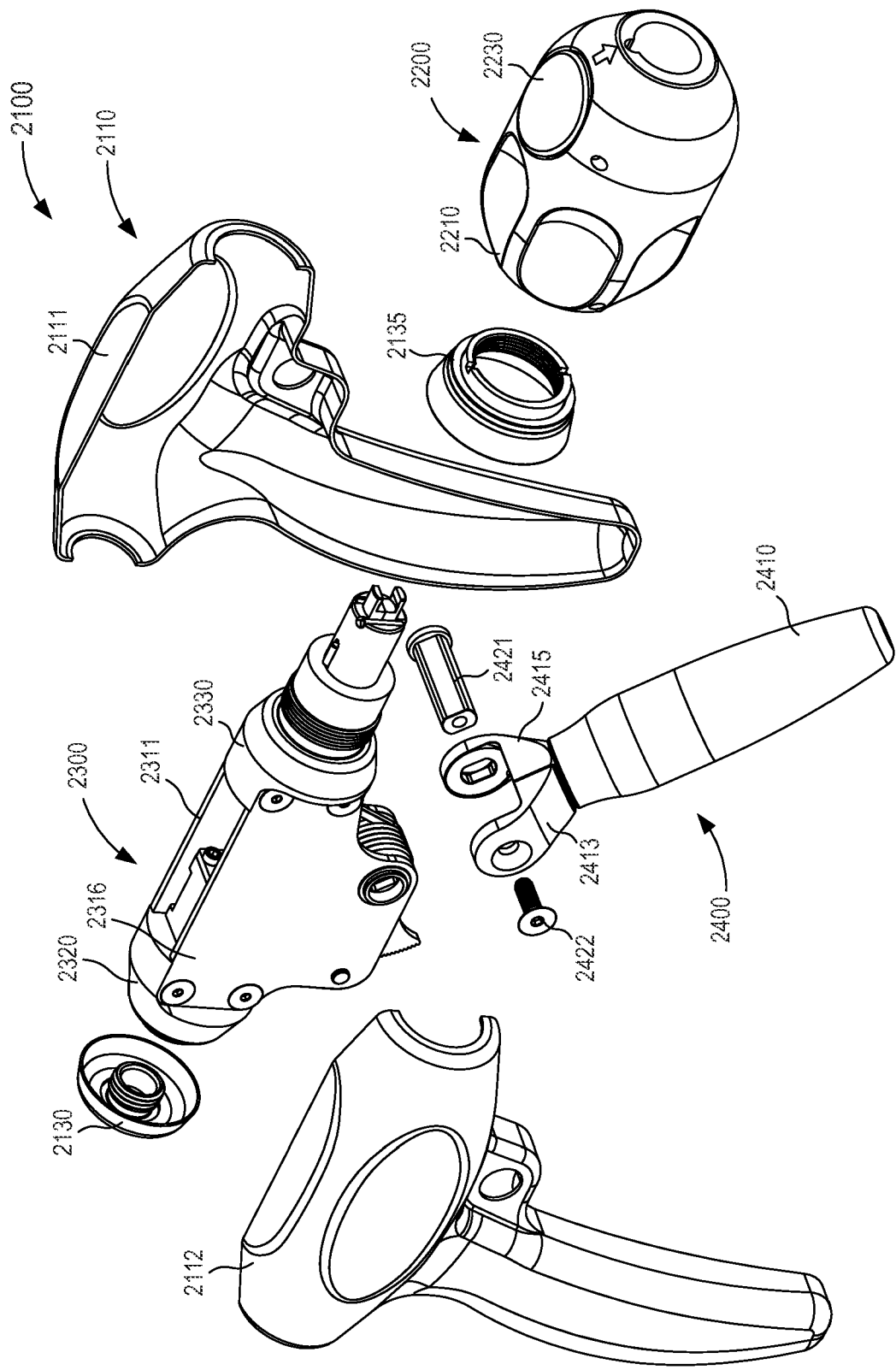
FIG. 4 is an exploded view of the universal handle of FIG. 3.

As shown in FIGS. 3 and 4, the reusable universal handle 2100 (also referred to herein as "handle") includes a housing 2110, a lock mechanism 2200, a drive mechanism 2300, and an actuator 2400. The housing 2110 can be any suitable shape, size, and/or configuration. For example, the housing 2110 includes a first member 2111 and a second member 2112 that are coupled together to collectively form the housing 2110, as shown in FIGS. 4-6. The housing 2110 includes and/or otherwise forms a body portion 2115 and a grip portion 2120. Moreover, the first member 2111 and the second members 2112 can be coupled together to define an inner volume 2125 of the housing 2110. As described in further detail herein, at least a portion of the drive mechanism 2300 and at least a portion of the actuator 2400 are movably disposed within the body portion of the housing 2110 (see e.g., FIG. 4). Similarly stated, a portion of the drive mechanism 2300 and a portion of the actuator 2400 are movably disposed in the inner volume 2125 in such a manner that the body portion 2115 of the housing 2110 substantially encloses the portion of the drive mechanism 2300 and the portion of the actuator 2400.

The grip portion 2120 of the housing 2110 extends from the body portion 2115 and is configured to be engaged by a user, as described in further detail herein. The body portion 2115 of the housing 2110 has a proximal end portion 2116 and a distal end portion 2118, as shown in FIGS. 5 and 6. The proximal end portion 2116 and the distal end portion 2118 define a proximal opening 2117 and a distal opening 2119, respectively. As such, the proximal opening 2117 and the distal opening 2119 can be configured to provide access to the inner volume 2115 defined by the housing 2110. For example, the housing 2110 includes a proximal coupler 2130 (see e.g., FIG. 4) that is disposed on and/or adjacent to an outer surface of the housing 2110 such that a portion of the proximal coupler 2130 extends into the inner volume 2125 to be coupled to a portion of the drive mechanism 2300. Furthermore, the arrangement of the drive mechanism 2300 within the inner volume 2125 of the housing 2110 can be such that a portion of the drive mechanism 2300 extends through the distal opening 2119 to be coupled to a distal coupler 2135 of the housing 2110. In this manner, the proximal coupler 2130 and the distal coupler 2135 can be coupled to the drive mechanism 2300 to suspend the drive mechanism 2300 in the inner volume 2125.

Figure 7:
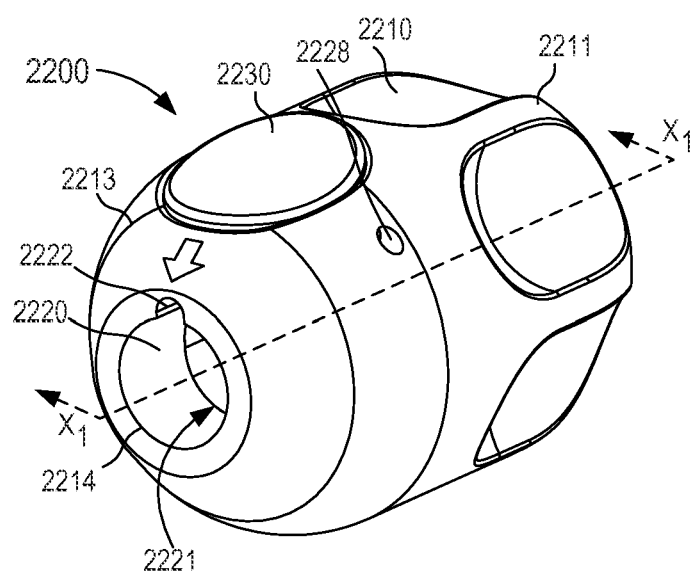
FIG. 7 is a perspective view of a lock mechanism included in the universal handle of FIG. 3.
Figure 8:
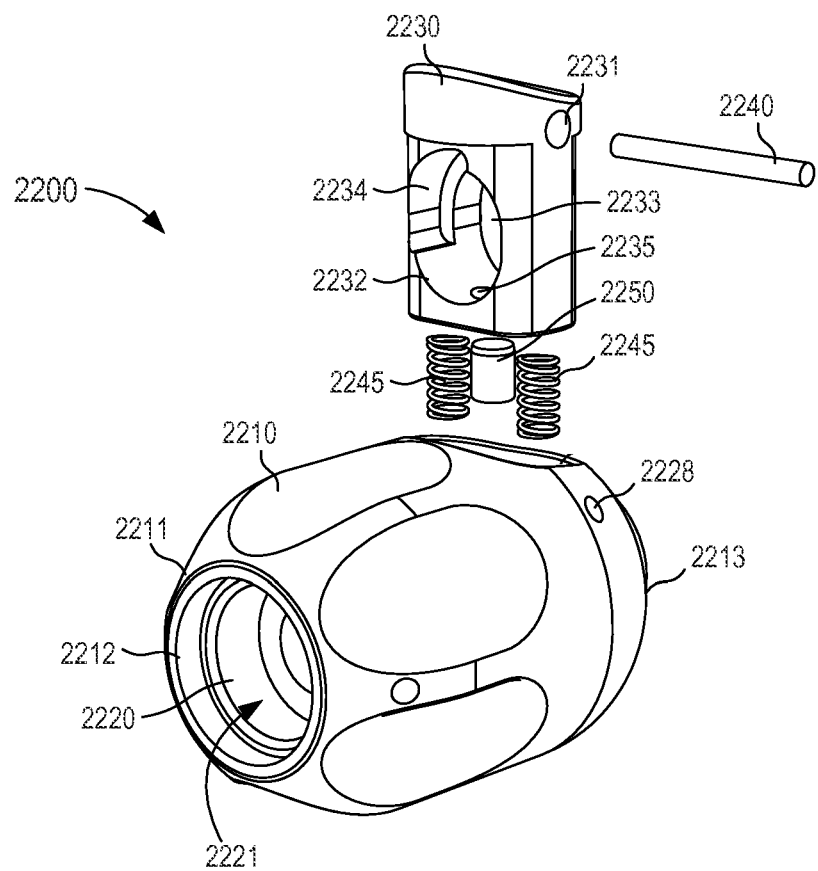
FIG. 8 is an exploded view of the lock mechanism of FIG. 7.
Figure 9:
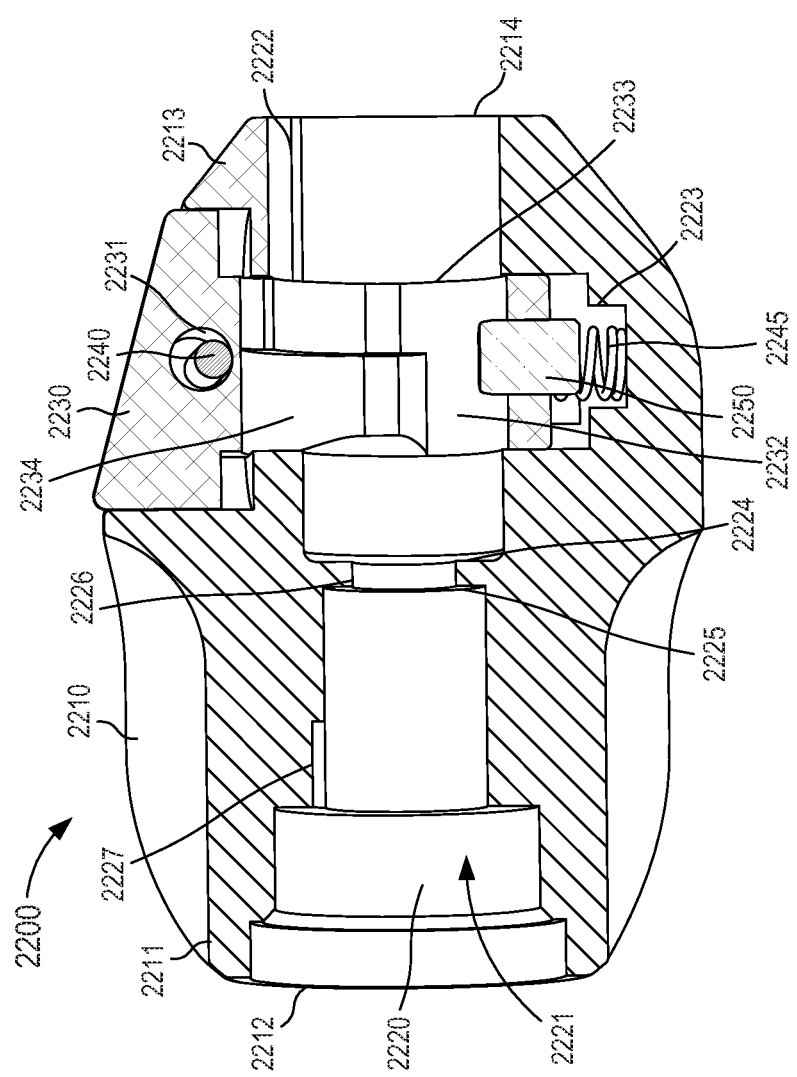
FIG. 9 is a cross-sectional view of the lock mechanism taken of FIG. 7, taken along the line $X_1$-$X_1$.

The lock mechanism 2200 of the handle 2100 is configured to be coupled to the distal end portion 2117 of the housing 2110 (see e.g., FIG. 3). More specifically, the lock mechanism 2200 can engage the distal coupler 2135 of the housing 2110 to couple the lock mechanism 2200 thereto. As shown in FIGS. 7-9, the lock mechanism 2200 includes a body portion 2210 and a lock actuator 2230. The body portion 2210 has a proximal end portion 2211 and a distal end portion 2213. The proximal end portion 2211 and the distal end portion 2213 each define an opening 2212 and 2214, respectively. The body portion 2210 further includes and/or forms an inner surface 2220 that defines an inner volume 2221, which is configured to receive a portion of the drive mechanism 2300 and a portion of the cartridge assembly 2500. As shown in FIG. 9, the inner surface 2220 is configured to form and/or define any suitable notch, recess, detent, channel, groove, and/or the like that can selectively receive and/or engage a portion of the drive mechanism 2300 and/or a portion of the cartridge assembly 2500. For example, the inner surface 2220 defines a first notch 2222, a second notch 2227, and a channel 2223. In addition, the inner surface 2220 includes a medial portion 2226 that forms and/or defines an annular proximal shoulder 2225 and an annular distal shoulder 2226. As described in further detail herein, the first notch 2222 defined by the inner surface 2220 is configured to selectively receive a portion of the cartridge assembly 2500, the second notch 2227 is configured to receive a portion of the drive mechanism 2300, and the channel 2223 is configured to movably receive the lock actuator 2230. Furthermore, the drive mechanism 2300 can be inserted into inner volume 2221 such that a distal surface of the drive mechanism 2300 is placed in contact with the proximal shoulder 2225, and the cartridge assembly 2500 can be inserted into the inner volume 2221 such that a proximal surface is placed in contact with the distal shoulder 2226.

As shown in FIGS. 8 and 9, the lock actuator 2230 is movably disposed in the channel 2223 defined and/or otherwise formed by the inner surface 2220 of the body portion 2210. The lock actuator 2230 has an inner surface 2232 that defines an opening 2233 extending through the lock actuator 2230. More specifically, the arrangement of the opening 2233 extending through the lock actuator 2230 can be such that an axial centerline of the opening 2233 is substantially parallel to and/or configured to be aligned with an axis defined by the inner volume 2221 of the body portion 2210, as shown in FIG. 9. The inner surface 2232 of the lock actuator 2230 further forms and/or defines a channel 2234 and a lock member aperture 2235 (FIG. 8). The channel 2234 is configured to selectively receive a portion of the cartridge assembly 2500, as described in further detail herein. The lock member aperture 2235 is configured to receive a lock member 2250. More specifically, the lock member 2250 can be disposed in the lock member aperture 2235 and arranged such that an outer surface of the lock member 2250 and the inner surface 2220 of the body portion 2210 collectively form and/or define a friction fit that is sufficient to retain the lock member 2250 in a substantially fixed position relative to the opening 2233 defined by the inner surface 2220. By way of example, the lock member 2250 can be disposed in the lock member aperture 2235 such that a portion of the lock member 2250 extends into the opening 2233, as described in further detail herein. Although the lock member 2250 and the lock actuator 2230 are shown and described as being formed independently and subsequently coupled together, in other embodiments, the lock member 2250 and the lock actuator 2230 can be monolithically and/or unitarily formed.

As described above, the lock actuator 2230 is movably disposed in the channel 2223 defined by the inner surface 2220. More specifically, the lock actuator 2230 can be moved in a transverse direction within the channel 2223 between a first position and a second position relative to the body portion 2210 of the lock mechanism 2200. The lock actuator 2230 can be movably retained within the channel 2223 in any suitable manner. For example, as shown in FIGS. 8 and 9, the body portion 2210 and the lock actuator 2230 each define a pin aperture 2228 and 2231, respectively, that receive a pin 2240. Expanding further, the pin 2240 can be disposed in the pin aperture 2228 defined by the body portion 2210 such that an outer surface of the pin 2240 and an inner surface defining the pin aperture 2228 collectively define and/or form a friction fit that is sufficient to maintain the pin 2240 in a relatively fixed position relative to the body portion 2210. Conversely, the pin aperture 2231 defined by the lock actuator 2230 can have a size and/or shape that is larger than a size and/or diameter of the pin 2240. Thus, with the pin 2240 maintained in a substantially fixed position relative to the body portion 2210, the lock actuator 2230 can be moved relative to the pin 2240.

As shown in FIGS. 8 and 9, the lock mechanism 2200 includes a set of bias members 2245 that are disposed between the inner surface 2220 of the body portion 2210 that defines a portion of the channel 2223 and a surface of the lock actuator 2230. As such, the bias members 2245 (e.g., springs or the like) can be transitioned between a first configuration of lower potential energy to a second configuration of greater potentially energy when the lock actuator 2230 is moved from its first position to its second position relative to the body portion 2210. Similarly stated, the bias members 2245 can exert a reaction force in response to a force exerted (e.g., by a user) to move the lock actuator 2230 from its first position to its second position. Thus, if the force that was exerted to move the lock actuator 2230 from its first position to its second position is removed, the bias members 2245 can exert a force to move the lock actuator 2230 from its first position to its second position, as described in further detail herein.

Figure 10:
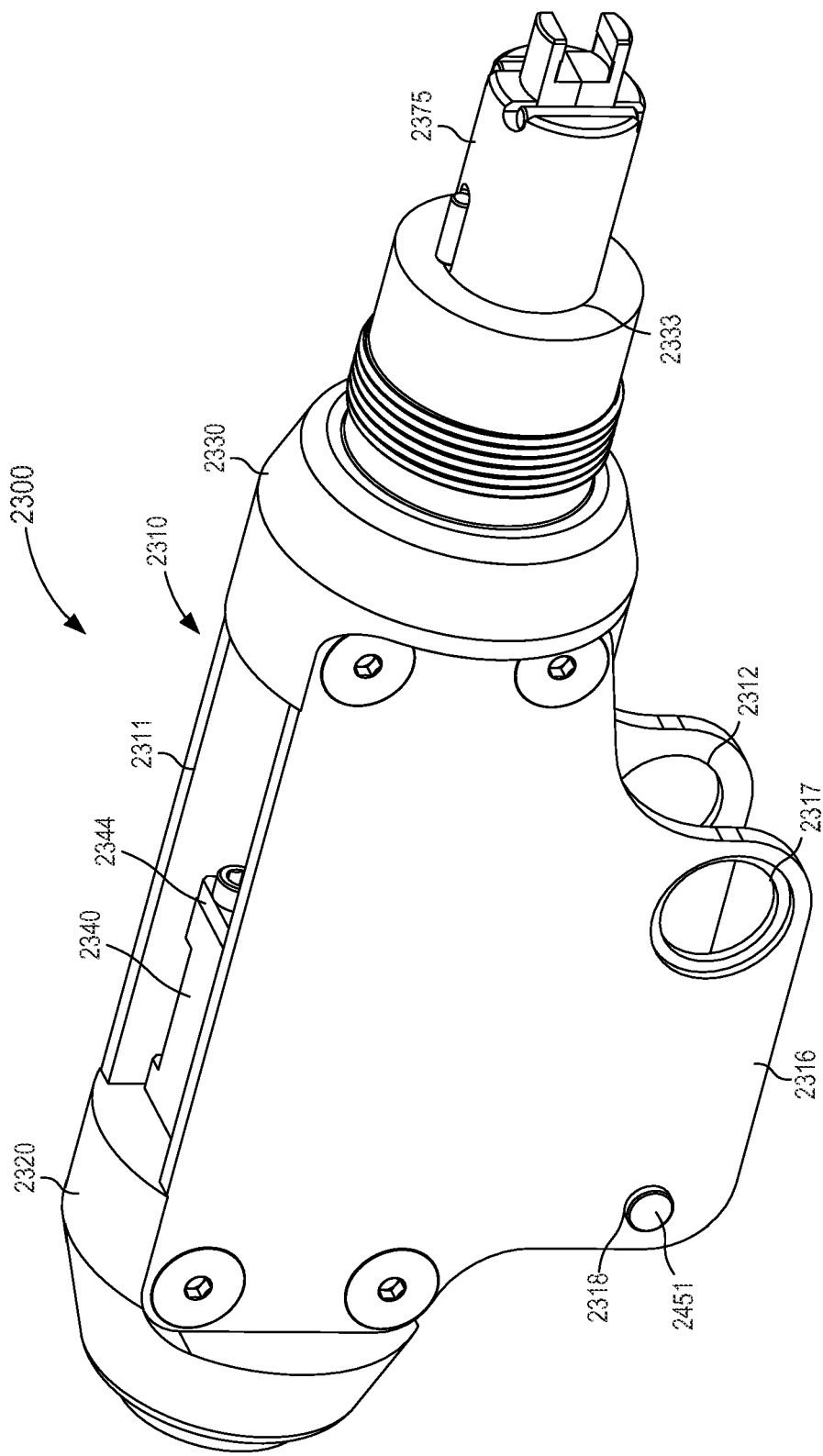
FIG. 10 is a perspective view of a drive mechanism included in the universal handle of FIG. 3.
Figure 12:
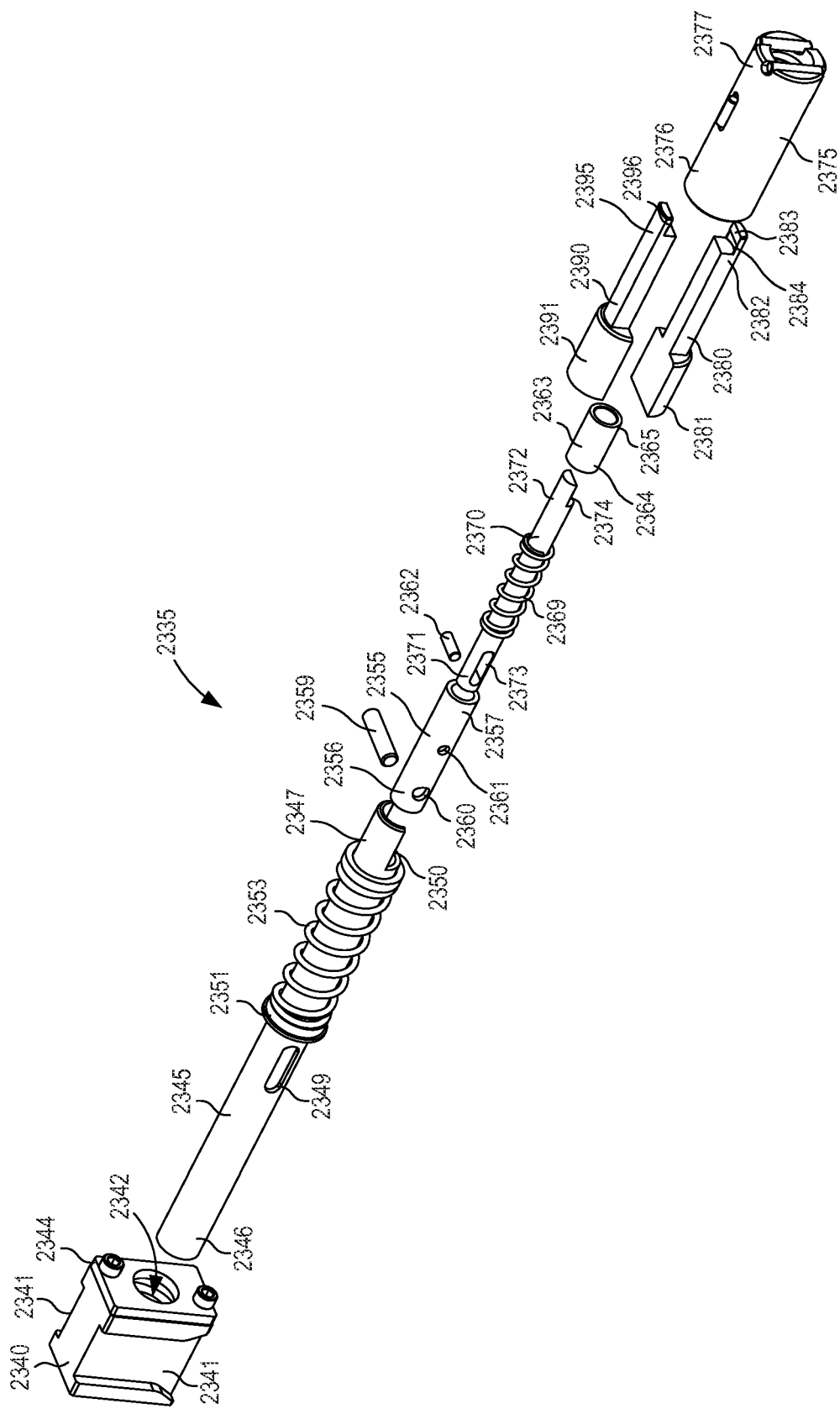
FIG. 12 is an exploded view of a portion of the drive mechanism of FIG. 10.
Figure 13:
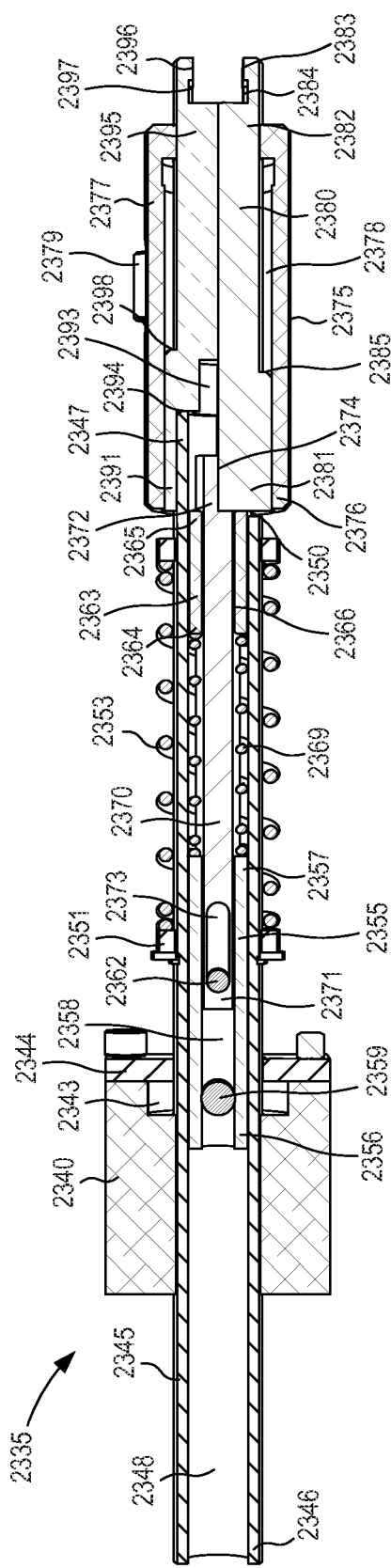
FIG. 13 is a cross-sectional view of the portion of the drive mechanism illustrated in FIG. 12, taken along the line $X_2$-$X_2$ in FIG. 11.
Figure 14:
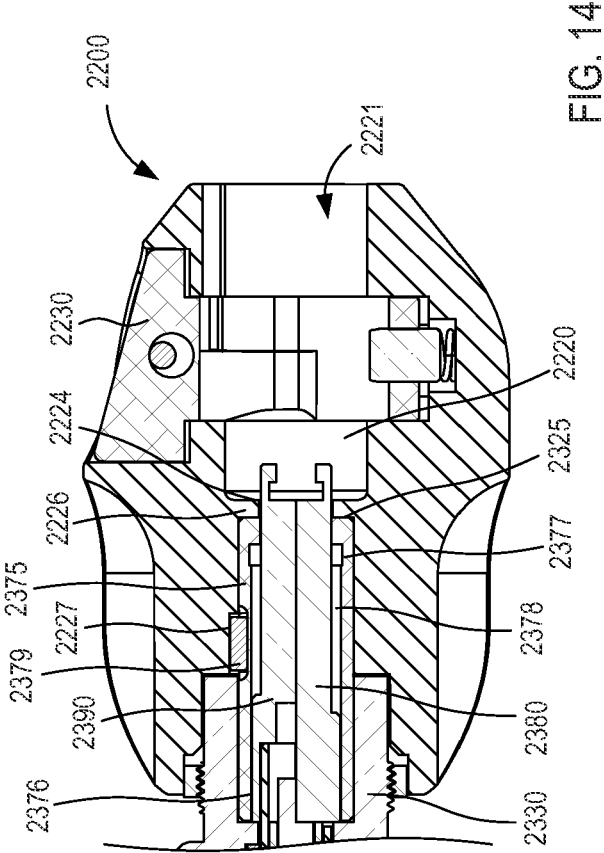
FIG. 14 is a cross-sectional view of a portion of the drive mechanism illustrated in FIG. 12 coupled to the lock mechanism of FIG. 7.
Figure 15:
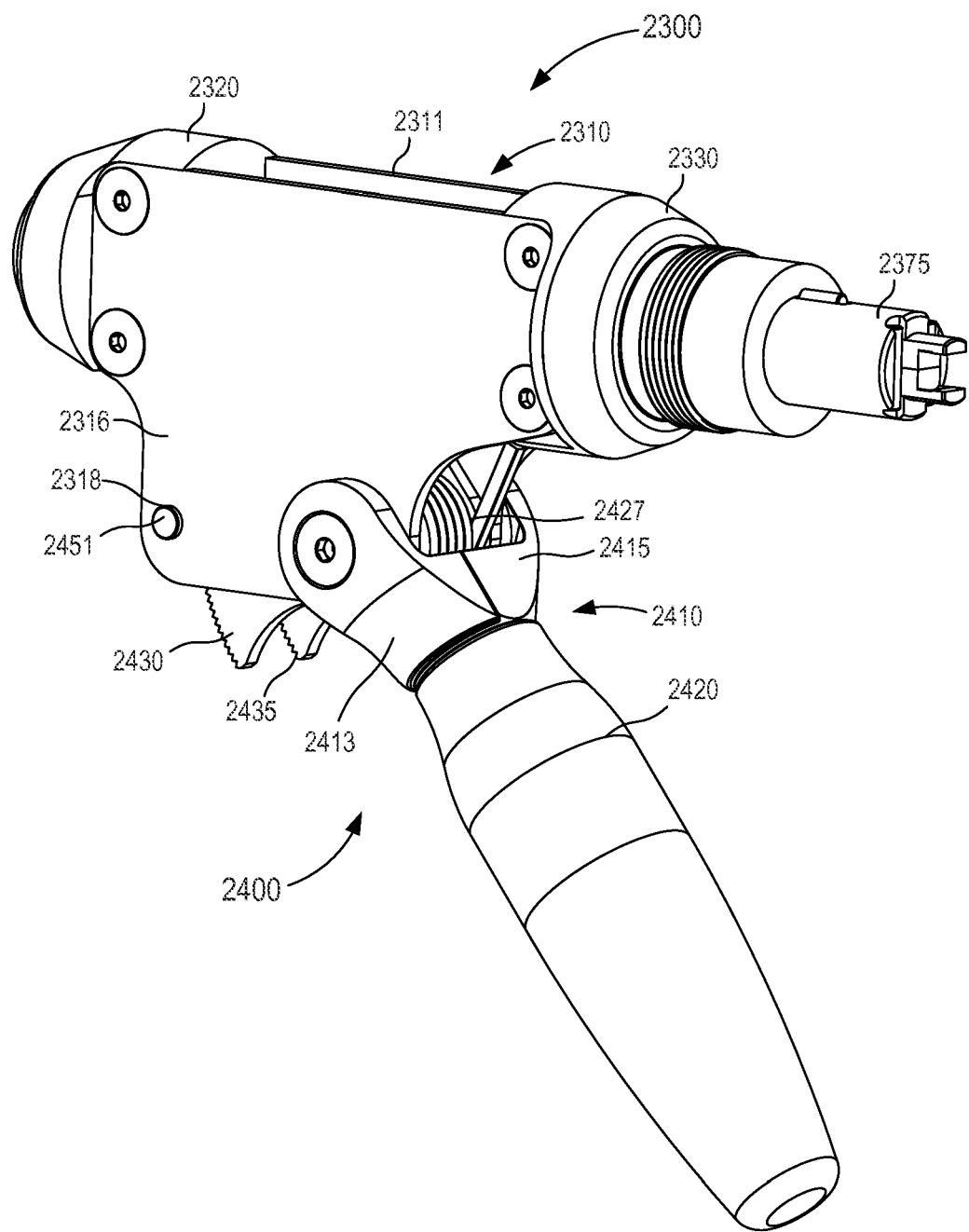
FIG. 15 is a perspective view of the drive mechanism coupled to an actuator included in the universal handle of FIG. 3.

As described above, at least a portion of the drive mechanism 2300 of the handle 2100 is movably disposed in the inner volume 2125 of the housing 2110. As shown in FIGS. 10-14, the drive mechanism 2300 includes a support structure 2310 and a movable portion 2335. The support structure 2310 can include any suitable structure and/or the like that is configured to support, at least in part, the movable portion 2335 and/or that is configured to couple the movable portion 2335 to the housing 2110. For example, the support structure 2310 includes a proximal support member 2320, a distal support member 2330, a first side plate 2311, and a second side plate 2316. The proximal support member 2320 defines an opening 2323 configured to receive a portion of the proximal coupler 2130 (as described above). More specifically, the proximal support member 2320 and the portion of the proximal coupler 2130 can form a threaded coupling or the like that can maintain the proximal support member 2320 in a substantially fixed position relative to the housing 2110. The arrangement of the drive mechanism 2300 in the inner volume 2125 of the housing 2100 is such that a portion of the distal support member 2330 extends through the distal opening 2119 defined by the housing 2110. In this manner, the distal coupler 2135 can be coupled to a portion of the distal support member 2330 to maintain the distal support member 2330 in a substantially fixed position relative to the housing 2110. For example, the distal coupler 2135 and a portion of the distal support member 2330 can form a threaded coupling or the like. In other embodiments, the distal coupler 2135 and the distal support member 2330 can form any suitable coupling such as, for example, a friction fit, a press fit, a snap fit, and/or can be coupled together via an adhesive or mechanical fastener (e.g., a screw, pin, bolt, etc.). As shown in FIGS. 10 and 14, the distal support member 2330 defines an opening 2333 that is configured to receive a distal sleeve 2375 of the movable portion 2335. Similarly, the opening 2323 defined by the proximal support member 2320 movably receives a first drive tube 2345 of the movable portion 2335. In this manner, the proximal support member 2320 and the distal support member 2330 can support and/or suspend the movable portion 2335 in the inner volume 2125 of the housing 2110.

Figure 11:
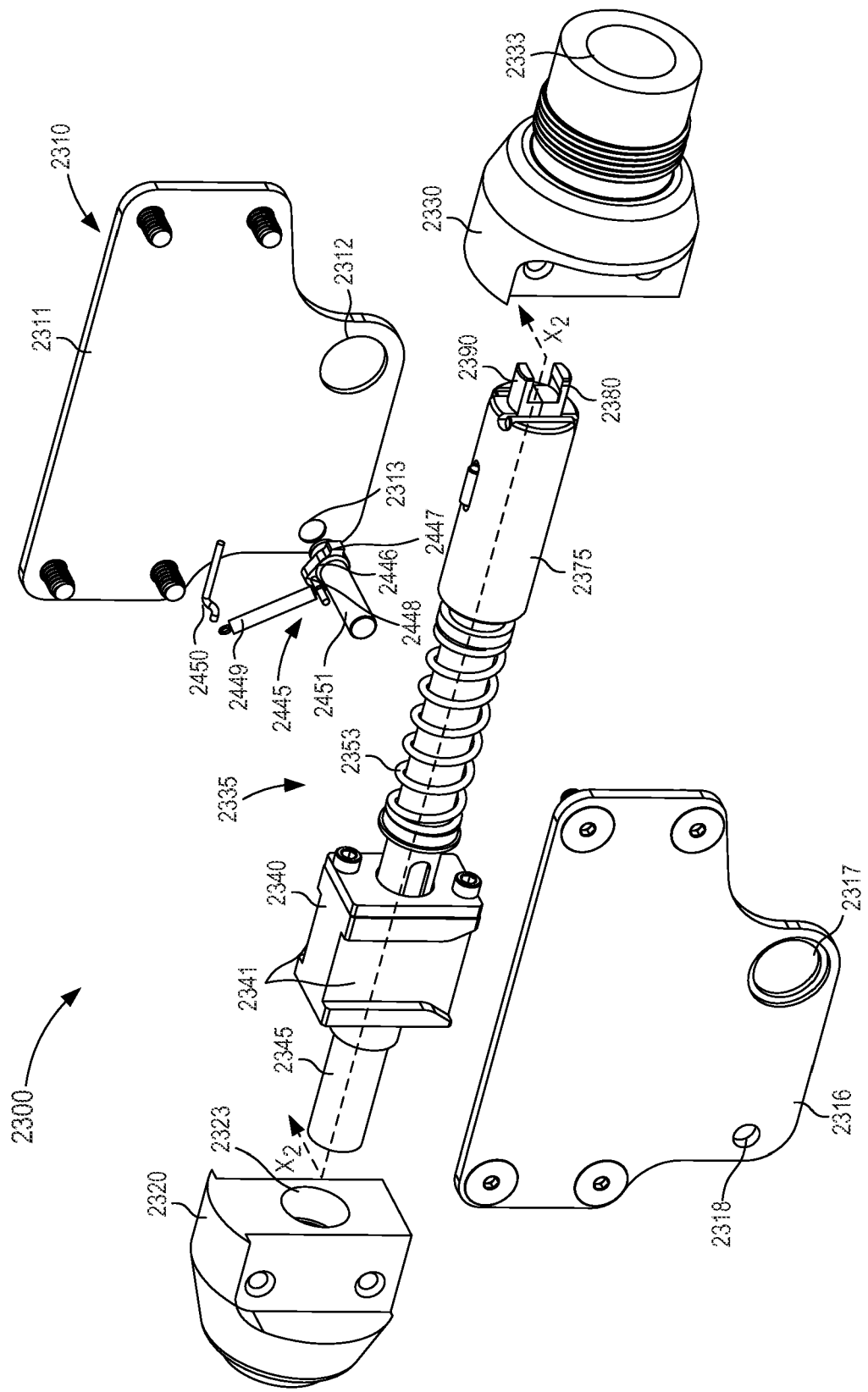
FIG. 11 is a partial exploded view of the drive mechanism of FIG. 10.

The first side plate 2311 and the second side plate 2316 are coupled to opposite sides of the proximal support member 2320 and the distal support member 2330, as shown in FIG. 10. Thus, the support structure 2110 can form a frame or the like configured to support the movable portion 2335. As shown in FIG. 11, the first side plate 2311 defines a first opening 2312 configured to receive a cam portion 2425 of the actuator 2400 and a second opening 2313 configured to receive a return portion 2445 of the actuator 2400. Similarly, the second plate 2316 defines an first opening 2317 configured to receive the first portion of the actuator 2400 and a second opening 2318 configured to receive the second portion of the actuator 2400, as described in further detail herein.

The movable portion 2335 of the drive mechanism 2300 is movably suspended and/or movably supported by the support structure 2310 and configured to be moved through any number of configurations and/or positions. The movable portion 2335 can be any suitable shape, size, or configuration. Moreover, the movable portion 2335 can include any number of parts, members, and/or subassemblies that can be moved in a substantially concurrent process and/or that can be moved in any number of independent processes. As shown in FIGS. 11-13, the movable portion 2335 includes a shuttle 2340, the first actuating tube 2345, a second actuating tube 2355, a first bias member 2353, a second bias member 2369, a push sleeve 2363, a push rod 2370, a first coupling member 2380, a second coupling member 2390, and the distal sleeve 2375. The shuttle 2340 defines a set of channels 2341 and an opening 2342. The channels 2341 movably receive a portion of the actuator 2400, as described in further detail herein. The opening 2342 movably receives the first actuating tube 2345. Similarly stated, the shuttle 2340 is movably disposed about the first actuating tube 2345.

The first actuating tube 2345 of the movable portion 2335 has a proximal end portion 2346 and a distal end portion 2347 and defines a lumen 2348 therethrough (see e.g., FIG. 13). The first actuating tube 2345 movably receives the second actuating tube 2355, the push sleeve 2363, and the push rod 2370. Similarly stated, the second actuating tube 2355, the push sleeve 2363, and the push rod 2370 are movably disposed within the lumen 2348 of the first actuating tube 2345. The proximal end portion 2346 of the first actuating tube 2345 is movably disposed in the opening 2323 defined by the proximal support member 2320. The distal end portion 2347 is configured to selectively engage the first coupling member 2380 and the second coupling member 2390. More specifically, the distal end portion 2347 defines a notch 2350 that can have a shape and/or arrangement such that the distal end portion 2347 selectively engages the first coupling member 2380 and/or the second coupling member 2390, as described in further detail herein. The first actuating tube 2345 also defines a slot 2349 (FIG. 12) that can movably receive a first pin 2359 (FIG. 13). The arrangement of the first pin 2359 within the slot 2349 can be such that each end portion of the first pin 2359 extends beyond an outer surface of the first actuating tube 2345. As such, when the first actuating tube 2345 is disposed in the opening 2342 defined by the shuttle 2340, the end portions of the first pin 2359 can be disposed in a recess 2343 defined by an inner surface of the shuttle 2340, as shown in FIG. 13. The shuttle 2340 also includes a distal cap 2344 that can be coupled to the shuttle 2340 to form, for example, a distal boundary of the recess 2343. In other words, the opening 2342 defined by the shuttle 2340 can include a first portion having a first diameter (i.e., the recess 2343) and a second portion having a second diameter that is smaller than the first diameter. Thus, when the distal cap 2344 is coupled to the shuttle 2340, the recess 2343 having, for example, the first diameter, is bounded in the distal direction by the distal cap 2344 and is bounded in the proximal direction by the smaller diameter of, for example, the second portion of the opening 2341. Furthermore, the size and/or shape of the recess 2343 can substantially correspond with the diameter and/or size of the first pin 2359. Therefore, when the pin 2359 is disposed in the slot 2349 defined by the first actuating tube 2345 and the first actuating tube 2345 is inserted through the opening 2341 defined by the shuttle 2340, the pin 2359 is maintained in a substantially fixed position (e.g., an axial position) within the recess 2343 of the shuttle 2340. This arrangement can be such that movement of the shuttle 2340 in an axial direction relative to the first actuating tube 2345 results in a similar and/or concurrent movement of the first pin 2359, as described in further detail herein.

As shown, the first bias member 2353 is disposed about a portion of the first actuating tube 2345. The first bias member 2353 can be any suitable device and/or member such as, for example, a spring or the like. The first actuator tube 2345 includes and/or is fixedly coupled to a proximal stop 2351 that is configured to limit a proximal movement of a portion of the first bias member 2353. Similarly, although not shown in FIGS. 10-14, the distal support member 2330 can include and/or can form a shoulder or surface that can contact the first bias member 2353 (and/or a washer or the like disposed therebetween) to limit a distal movement of a portion of the first bias member 2353. In this manner, the first bias member 2353 can be transitioned between a first configuration having a first potential energy and a second configuration having a second potential energy that is greater than the first potential energy, as described in further detail herein.

The second actuating tube 2355 of the movable portion 2335 has a proximal end portion 2356 and a distal end portion 2357 and defines a lumen 2358 therethrough (see e.g., FIG. 13). The second actuating tube 2355 movably receives the push rod 2370. Similarly stated, the push rod 2370 is movably disposed in the lumen 2358 defined by the second actuating tube 2355. The second actuating tube 2355 also defines a first transverse opening 2360 and a second transverse opening 2361 (e.g., transverse to an axis defined by the lumen 2358). The first transverse opening 2360 is configured to receive the first pin 2359 and the second transverse opening 2361 is configured to receive a second pin 2362. The size and/or diameter of the first transverse opening 2360 and the size and/or diameter of the second transverse opening 2361 can substantially correspond with the size and/or diameter of the first pin 2359 and a size and/or diameter of the second pin 2362, respectively. Thus, when the first pin 2359 is inserted into the first transverse opening 2360, the first pin 2359 is maintained in a substantially fixed axial position relative to the second actuating tube 2355. Moreover, with the first pin 2359 maintained in the substantially fixed axial position relative to the shuttle 2340 (as described above) and the substantially fixed axial position relative to the second actuating tube 2355, movement of the shuttle 2340 in the axial direction results in a similar and/or concurrent movement of the second actuating tube 2355, as described in further detail herein. Similarly, when the second pin 2362 is inserted into the second transverse opening 2361 of the second actuating tube 2355, the second pin 2362 is maintained in a substantially fixed axial position relative to the second actuating tube 2355. Therefore, movement of the second actuating tube 2355 in the axial direction results in a similar and/or concurrent movement of the second pin 2362, as described in further detail herein.

The push sleeve 2363 of the movable portion has a proximal end portion 2364 and a distal end portion 2365 and defines a lumen 2366 therethrough. The push sleeve 2363 movably receives the push rod 2370. Similarly stated, the push rod 2370 is movably disposed in the lumen 2366 defined by the push sleeve 2363. As shown in FIG. 13, the arrangement of the second actuating tube 2355, the push sleeve 2363, the push rod 2370 can be such that the second bias member 2369 is disposed between the distal end portion 2357 of the second actuating tube 2355 and the proximal end portion 2364 of the push sleeve 2363. As described above with reference to the first bias member 2353, the second bias member 2369 can be transitioned between a first configuration having a first potential energy and a second configuration having a second potential energy that is greater than the first potential energy. Moreover, the second actuating tube 2355 can exert a force on the second bias member 2369 as the second actuating tube 2355 is moved in the distal direction (e.g., moved axially in the lumen 2348 defined by the first actuating tube 2348), and in turn, the second bias member 2369 can exert at least a portion of the force on the push sleeve 2363. In some instances, the portion of the force exerted by the second bias member 2369 on the push sleeve 2363 is sufficient to overcome a reaction exerted by the push sleeve 2363 and thus, the push sleeve 2363 can be moved in a substantially concurrent manner with the second actuating tube 2355. In other instances, the drive mechanism 2300 can be placed in a configuration in which the push sleeve 2363 exerts a reaction force that is sufficient to overcome the portion of the force exerted by the second bias member 2369. Thus, further distal movement of the second actuating tube 2355 can transition the second bias member 2369 from substantially its first configuration towards its second configuration, as described in further detail herein.

The push rod 2370 of the movable portion 2335 has a proximal end portion 2371 and a distal end portion 2372. The proximal end portion 2371 is movably disposed in the second actuating tube 2355. Moreover, as shown in FIGS. 12 and 13, the push rod 2370 defines a slot 2373 that is configured to movably receive the second pin 2362. Therefore, with the second pin 2362 disposed in a substantially fixed axial position relative to the second actuating tube 2355, movement of the second actuating tube 2355 in an axial direction (e.g., a distal direction and/or a proximal direction) can move the second pin 2362 within the slot 2373 until the second pin 2362 is placed in contact with an inner surface defining a boundary of the slot 2373. The distal end portion 2372 of the push rod 2370 is configured to selectively engage the first coupling member 2380 and the second coupling member 2390. For example, the distal end portion 2372 defines a notch 2374 that can have a shape and/or arrangement such that the distal end portion 2372 can be matingly coupled to the first coupling member 2380. More specifically, in some embodiments, the distal end portion 2372 of the push rod 2370 can be fixedly coupled to the first coupling member 2380 via, for example, welding (e.g., ultrasonic welding), an adhesive, a mechanical fastener, and/or the like. Moreover, in some embodiments, the arrangement of the notch 2374 can be such that the distal end portion 2372 selectively engages the second coupling member 2390, as described in further detail herein.

The first coupling member 2380 of the movable portion 2335 has a proximal end portion 2381 and a distal end portion 2382. The first coupling member 2380 is movably disposed in a lumen 2378 defined by the distal sleeve 2375. The arrangement of the first coupling member 2380 and the distal sleeve 2375 can be such that when the first coupling member 2380 is disposed in the lumen 2378, the distal end portion 2382 of the first coupling member 2380 extends through the lumen 2378 to be disposed in a distal position relative to the distal sleeve 2375, as shown in FIG. 13. Moreover, the first coupling member 2380 also includes and/or forms a shoulder 2385 that can be selectively placed in contact with an inner surface of the distal sleeve 2375 that defines a portion of the lumen 2378, as described in further detail herein.

The proximal end portion 2381 of the first coupling member 2380 is in contact with the distal end portion 2365 of the push sleeve 2363 and the distal end portion 2372 of the push rod 2370. In this manner, axial movement of the push sleeve 2363 and/or the push rod 2370 in the distal direction moves the first coupling member 2380 in a substantially similar and/or concurrent manner in the distal direction, as described in further detail herein. The distal end portion 2382 of the first coupling member 2380 includes an extension 2383 that protrudes from a distal surface of the first coupling member 2380. Moreover, a surface of the extension 2383 forms and/or defines a recess 2384. As described in further detail herein, the recess 2384 can have and/or can define a shape and/or a radius that can, for example, selectively receive a portion of the cartridge assembly 2500.

The second coupling member 2390 of the movable portion 2335 has a proximal end portion 2391 and a distal end portion 2395. The second coupling member 2390 is movably disposed in the lumen 2378 defined by the distal sleeve 2375. The arrangement of the second coupling member 2390 and the distal sleeve 2375 can be such that when the second coupling member 2390 is disposed in the lumen 2378, the distal end portion 2395 of the second coupling member 2390 extends through the lumen 2378 to be disposed in a distal position relative to the distal sleeve 2375, as shown in FIG. 13. The proximal end portion 2391 of the second coupling member 2390 includes a contoured surface 2393 that can have a shape, size, and/or configuration that substantially corresponds with the distal end portion 2347 of the first actuating tube 2345, the distal end portion 2365 of the push sleeve 2363, and/or the distal end portion 2372 of the push rod 2370. For example, as shown in FIG. 13, the contoured surface 2393 can form and/or define a first shoulder 2394 that can be in contact with the distal end portion 2347 of the first actuating tube 2345 and that can be configured to allow the distal end portion 2372 of the push rod 2370 to extend beyond the first shoulder 2394, as described in further detail herein. As such, the first coupling member 2380 and the second coupling member 2390 can be selectively moved relative to the second coupling member 2390 or the first coupling member 2380, respectively. Moreover, this arrangement can be such that a portion of an axial movement of the first coupling member 2380 and a portion of an axial movement of the second coupling member 2390 is substantially similar and/or concurrent (e.g., the first coupling member 2380 and the second coupling member 2390 are collectively moved with substantially the same velocity). As described in further detail herein, an outer surface of the second coupling member 2390 defines and/or forms a second shoulder 2398 that can be selectively placed in contact with an inner surface of the distal sleeve 2375. The distal end portion 2395 of the second coupling member 2390 includes an extension 2396 that protrudes from a distal surface of the second coupling member 2390. Moreover, a surface of the extension 2396 forms and/or defines a recess 2397 that can have and/or can define a shape and/or a radius that can, for example, selectively receive a portion of the cartridge assembly 2500, as described in further detail herein.

The distal sleeve 2375 of the movable portion 2335 can be any suitable shape, size, and/or configuration. The distal sleeve 2375 has a proximal end portion 2376 and a distal end portion 2377 and defines the lumen 2378 therethrough. As described above, the lumen 2378 movably receives the first coupling member 2380 and the second coupling member 2390 such that a portion of the first coupling member 2380 and a portion of the second coupling member 2390 extend through the lumen 2378 to be disposed in a distal position relative to the distal sleeve 2375, as described in further detail herein. The proximal end portion 2376 of the distal sleeve 2375 is disposed in the opening 2333 defined by the distal support member 2330 (see e.g., FIG. 14). The distal end portion 2377 is disposed in the inner volume 2221 defined by the lock mechanism 2200. More particularly, as shown in FIG. 14, the distal end portion 2377 of the distal sleeve 2375 can be inserted into the inner volume 2221 of the lock mechanism 2200 such that a distal surface of the distal sleeve 2375 is placed in contact with the proximal shoulder 2325 formed by the medial portion 2226 of the lock mechanism 2200. The arrangement of the first coupling member 2380, the second coupling member 2390, the distal sleeve 2375, and the lock mechanism 2200 can be such that when the distal sleeve 2375 is placed in contact with the proximal shoulder 2225, a portion of the first coupling member 2380 and a portion of the second coupling member 2390 are disposed in a distal position relative to the distal shoulder 2224 formed by the medial portion 2226 of the lock mechanism 2200, as described in further detail herein. Furthermore, as shown in FIG. 14, the distal sleeve 2375 includes a key member 2379 that is partially disposed in the second notch 2227 defined by the inner surface 2220 of the lock mechanism 2200. As such, the lock mechanism 2200 can be maintained in a substantially fixed orientation relative to the drive mechanism 2300 (and vice versa).

Figure 16:
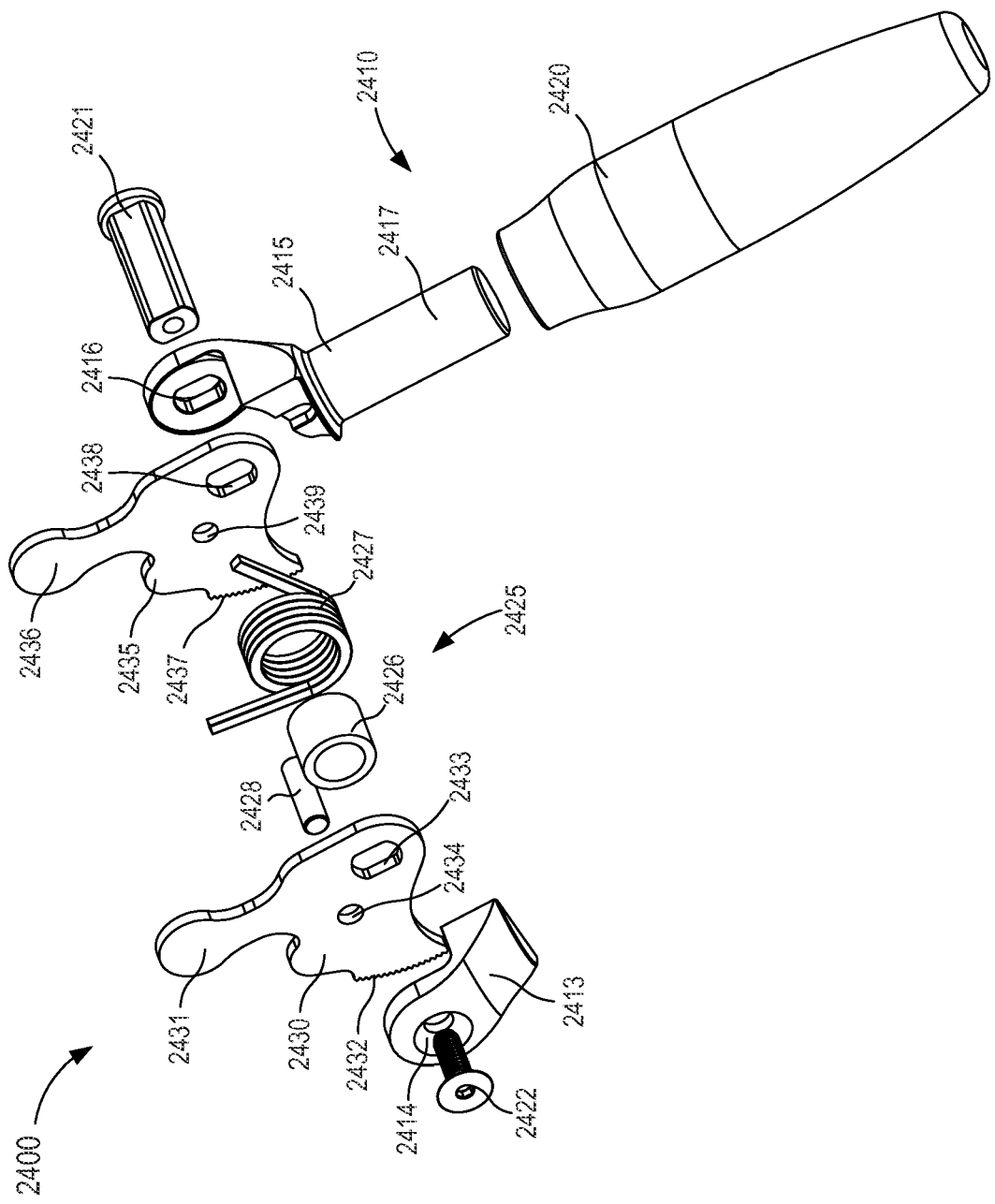
FIG. 16 is an exploded perspective view of the actuator illustrated in FIG. 15.

As described above, a portion of the actuator 2400 of the handle 2100 is movably disposed in the inner volume 2125 of the housing 2110 and is configured to be moved between any number of configurations and/or positions. As shown in FIGS. 15-18, a portion of the actuator 2400 can be rotatably coupled to the housing 2110 and/or the drive mechanism 2300. The actuator 2400 includes an engagement portion 2410, the cam portion 2425, and the return portion 2445. The engagement portion 2410 can be any suitable shape, size, and/or configuration. For example, as shown in FIG. 16, the engagement portion 2410 includes a trigger 2420, a first arm 2413 and a second arm 2415. The trigger 2420 can be disposed about and/or otherwise coupled to an extension 2417 of the second arm 2415. The first arm 2413 and the second arm 2415 can be coupled together to form a substantially bifurcated arrangement that can correspond to and/or otherwise be associated with a portion of the housing 2110 to which the first arm 2413 and the second arm 2415 are coupled (see e.g., FIGS. 3 and 4). More specifically, the first arm 2413 defines an opening 2414 that can receive a fastener 2422, and the second arm 2415 defines an opening 2416 that can receive an axle 2421. As shown in FIG. 16, the opening 2416 defined by the second arm 2415 can have a size and/or a shape that substantially corresponds to a size and/or a shape of the axle 2421. Thus, first arm 2415 can maintain the axle 2421 in a substantially fixed angular position relative to the engagement portion 2410. As such, the axle 2421 can extend through a set of corresponding holes defined by the first member 2111 and the second member 2112 of the housing 2110 in such a manner that the axle 2421 traverses the inner volume 2125 defined by the housing 2110 to be coupled to the fastener 2422, thereby coupling the engagement portion 2410 to the housing 2110. Furthermore, the drive mechanism 2300 can be arranged within the inner volume 2125 of the housing 2110 such that the first opening 2312 defined by the first side plate 2311 and the first opening 2317 of the second side plate 2316 are substantially aligned (e.g., coaxial) with the openings defined by the housing 2110. Thus, the axle 2421 can extend through the first opening 2312 of the first side plate 2311 and the first opening 2317 of the second side plate 2316 to rotatably couple the actuator 2400 to the drive mechanism 2300. Although not shown, in some embodiments, the first side plate 2311 and the second side plate 2316 can each include and/or can be coupled to a bearing or the like that can, for example, facilitate a rotation of the axle 2421 within the openings 2312 and 2317, respectively, as described in further detail herein.

As shown in FIG. 16, the cam portion 2425 includes a spacer 2426, a spring 2427, a post 2428, a first cam 2430, and a second cam 2430. The first cam 2430 includes an actuation portion 2431 and a rack portion 2432, and defines a first aperture 2433 and a second aperture 2434. The second cam 2435 can be substantially similar to or the same as the first cam 2430. Accordingly, the second cam 2435 includes an actuation portion 2436 and a rack portion 2437, and defines a first aperture 2438 and a second aperture 2439. Therefore, with the second cam 2435 being substantially similar to or the same as the first cam 2430, a discussion of the arrangement and function of the first cam 2430 with reference to FIGS. 16 and 17 applies to the second cam 2435 with reference to FIGS. 16 and 18, unless explicitly expressed otherwise.

Figure 17:
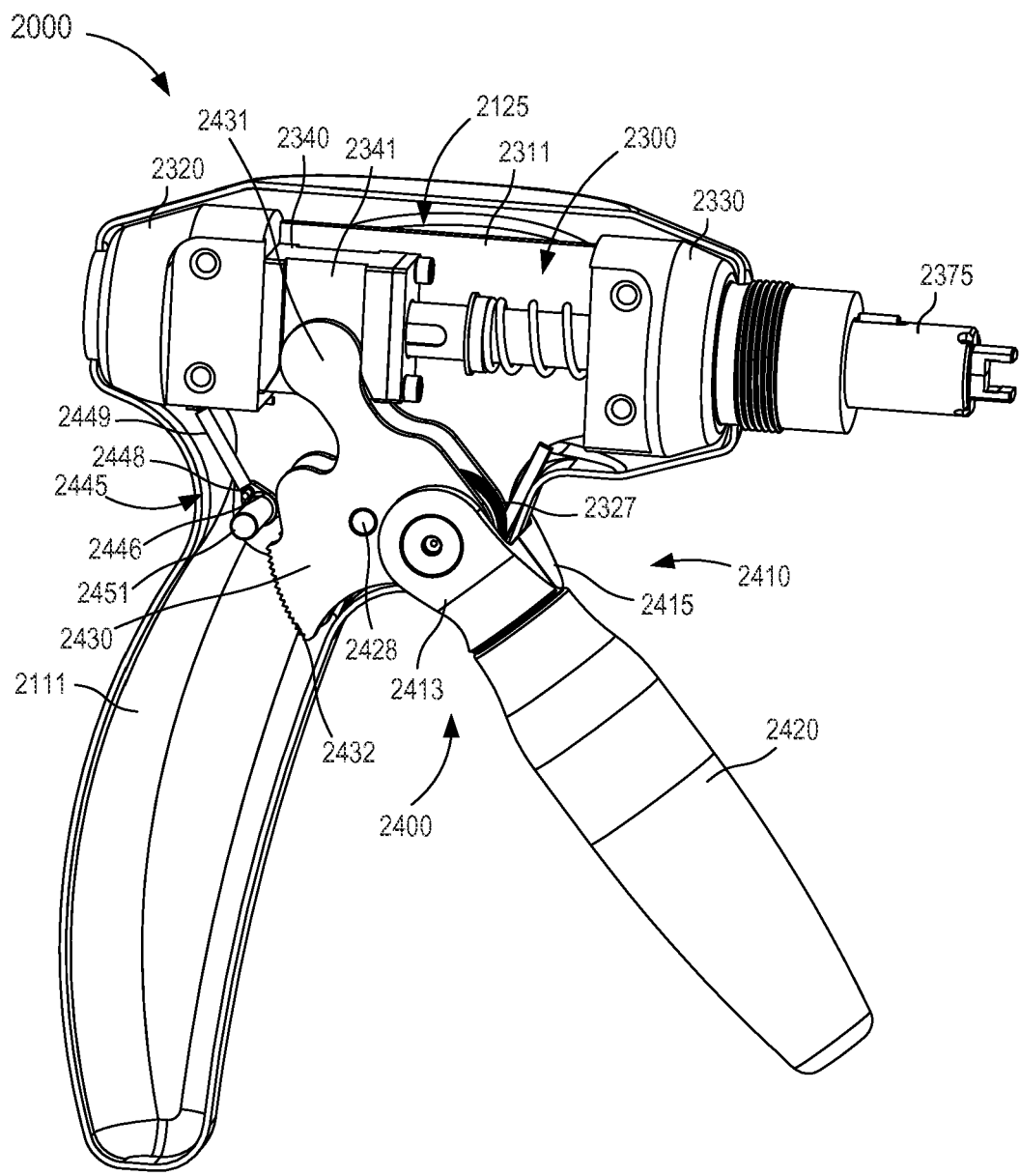
FIG. 17 is a right perspective view of a portion of the universal handle of FIG. 3 illustrating an engagement of a portion of the actuator of FIG. 15 and a portion of the drive mechanism of FIG. 10.

The actuation portion 2431 of the first cam 2430 can be movably disposed in one of the channels 2341 defined by the shuttle 2340 of the drive mechanism 2300 (e.g., the channel 2341 defined by a corresponding side of the shuttle 2340, as shown in FIG. 17). In this manner, the actuation portion 2431 and the shuttle 2340 can form a kinematic link and/or the like that can, for example, convert a rotational and/or pivoting motion of the first cam 2430 to a translational (e.g., axial) motion of the shuttle 2340, as described in further detail herein. The rack portion 2432 includes a set of teeth (e.g., similar to, for example, a gear or the like) that are configured to selectively engage a cam follower 2446 included in the return portion 2445, as described in further detail herein. The first aperture 2433 of the first cam 2430 receives a portion of the axle 2421. More specifically, the first aperture 2433 can have a size and/or shape that substantially corresponds with a shape and/or size of the axle 2421. In this manner, the axle 2421 is maintained in a substantially fixed position (e.g., angular position) relative to the first cam 2430. The second aperture 2434 of the cam 2430 receives a portion of the post 2428 to couple the post 2428 thereto (e.g., via a friction fit, a weld, an adhesive, and/or the like). As such, the post 2428 can be fixedly disposed in the second aperture 2434 of the first cam 2430 and can traverse a space defined between the first cam 2430 and the second cam 2435 to be fixedly disposed in the second aperture 2439 of the second cam 2435.

As shown, the spring 2427 is disposed between the first cam 2430 and the second cam 2435. More specifically, the spring 2427 is disposed about the spacer 2426, which in turn, is substantially aligned (i.e., coaxial) with the first openings 2433 and 2438 defined by the first cam 2430 and the second cam 2435, respectively. Thus, the axle 2421 can extend through the first openings 2433 and 2438 of the first cam 2430 and the second cam 2435, respectively, and the spacer 2426 to retain the spacer 2426 and the spring 2427 in a substantially fixed position (e.g., a linear position) relative to the drive mechanism 2300. Furthermore, in some embodiments, the spring 2427 can be, for example, a rotational spring or the like that includes a first end portion in contact with the post 2428 (not shown in FIGS. 15-18) and a second end portion in contact with an inner surface of the housing 2110 (see e.g., FIGS. 17 and 18).

The arrangement described above of the engagement portion 2410 and the cam portion 2425 of the actuator 2400 can be such that the engagement portion 2410 and the cam portion 2425 can pivot about an axis defined by the axle 2421. For example, in some instances, a force can be exerted on the engagement portion 2410 to pivot the trigger 2420 of the engagement portion 2410 towards the grip portion 2120 of the housing 2110. With the axle 2421 disposed in a substantially fixed angular position relative to the second arm 2415 of the engagement portion 2410 (e.g., due at least in part to the configuration of the opening 2416, as described above), the pivoting motion of the engagement portion 2410 can concurrently rotate the axle 2421 about its axis. Moreover, with the axle 2421 fixedly disposed in the first apertures 2433 and 2438 of the first cam 2430 and the second cam 2435, respectively (as described above), the pivoting motion of the axle 2421 can concurrently pivot the cam portion 2425 about the axis defined by the axle 2421. The pivoting motion of the engagement portion 2410 and the cam portion 2420 can, for example, transition the spring 2427 from a first configuration of lower potential energy to a second configuration of greater potential energy. In this manner, the actuator 2400 can be moved from, for example, a first angular position to a second angular position in which the spring 2427 can exert a force to move the actuator 2400 from its second angular position towards to its first angular position, as described in further detail herein.

Figure 18:
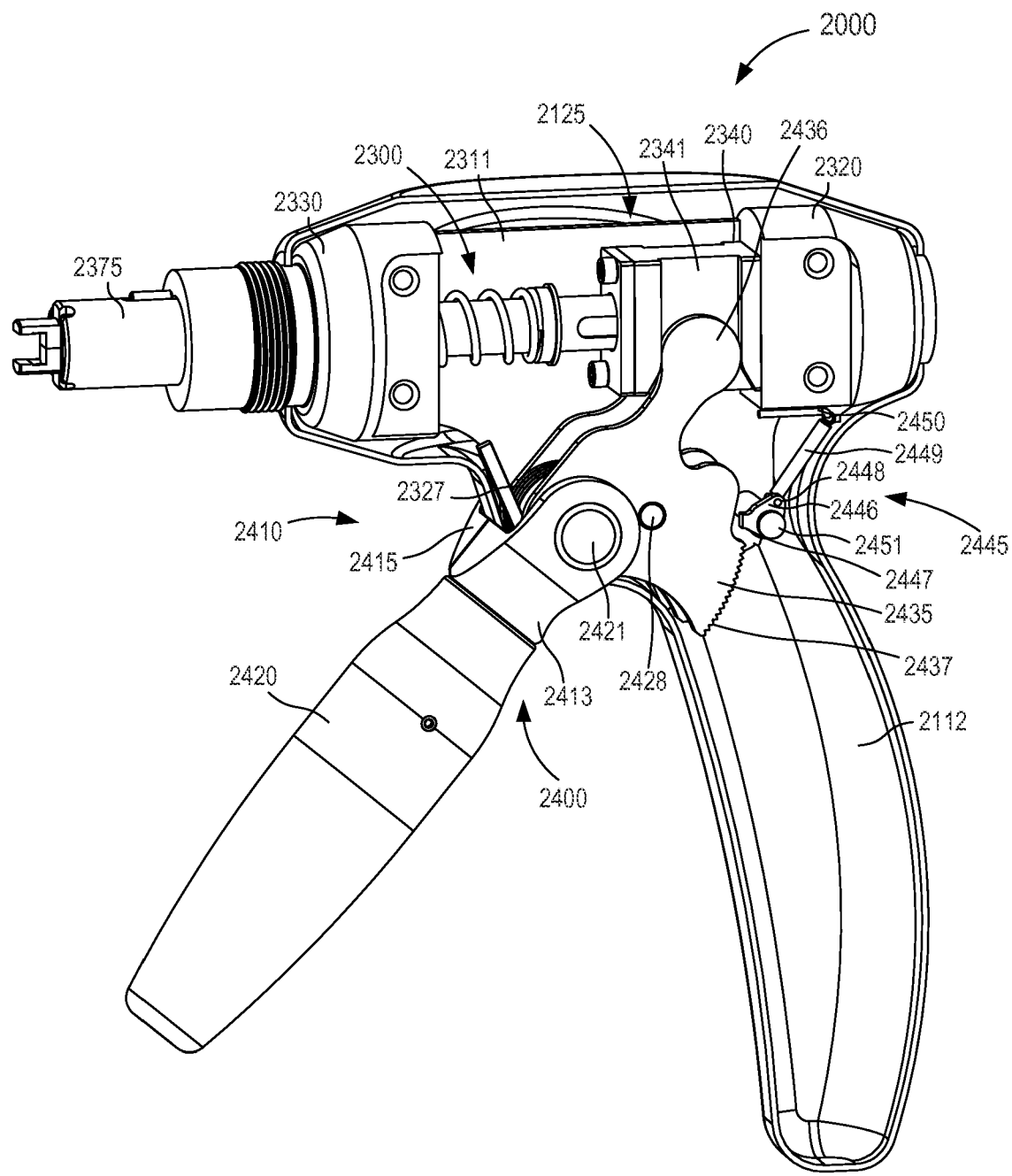
FIG. 18 is a left perspective view of a portion of the universal handle of FIG. 3 illustrating an engagement of a portion of the actuator of FIG. 15 and a portion of the drive mechanism of FIG. 10.

The return portion 2445 of the actuator 2400 can be any suitable configuration. For example, as shown in FIGS. 17 and 18, the return portion 2445 includes a cam follower 2446, a spring 2449, a post 2450, and an axle 2451. The axle 2451 is disposed in the second openings 2313 and 2318 of the first the first side plate 2311 and the second side plate 2316, respectively, of the drive mechanism 2300. Moreover, the arrangement of the axle 2451 and the first side plate 2311 and the second side plate 2316 is such that axle 2451 is maintained in a substantially fixed position relative to the drive mechanism 2300 as well as the remaining portions of the actuator 2400. The cam follower 2446 is rotatably disposed about the axle 2451. The cam follower 2446 includes a ratchet portion 2447 and a return portion 2448. The ratchet portion 2447 can be, for example, a substantially rectangular and/or polygonal protrusion that extends from the cam follower 2446. In this manner, the ratchet portion 2447 is configured to selectively engage the rack portion 2437 of the second cam 2435 to substantially limit a rotation of the second cam 2345.

The return portion 2448 of the cam follower 2448 is coupled to a first end portion of the spring 2449, as shown, for example, in FIG. 17. A second end portion (i.e., the end portion opposite the first end portion) of the spring 2449 is coupled to the post 2450. The post 2450 can be coupled to (e.g., via an adhesive, a weld, a mechanical fastener, and/or the like) and/or unitarily formed with the first side plate 2311 and/or the proximal support member 2320. This arrangement can be such that as the cam follower 2446 is rotated about the axle 2451 (e.g., in response to a rotation of the second cam 2435) between a first angular position and a second angular position, the return portion 2448 is rotated, for example, in an angular motion away from the post 2450, thereby placing the spring 2449 in tension. Thus, if an exerted force sufficient to rotate the cam follower 2446 is removed, the spring 2449 can exert a force to that can, in some instances, be sufficient to rotate the cam follower 2446 about the axle 2451 from the second angular position towards the first angular position, as described in further detail herein. For example, the rack portion 2437 of the second cam 2435 can selectively engage the ratchet portion 2447 such that, as the cam portion 2425 is rotated about the axis defined by the axle 2421 (e.g., in response to the trigger 2420 being rotated towards the grip portion 2120 of the housing 2110, as described above), the rack portion 2437 rotates the cam follower 2446 about the axle 2451 from a first angular direction, thereby rotating the return portion 2448 away from the post 2450. Thus, the ratchet portion 2447 of the cam follower 2446 can be moved along a surface of the rack portion 2437 (e.g., advanced along the teeth of the rack portion 3437). With the ratchet portion 2447 in contact with the rack portion 2437, the cam follower 2446 can substantially limit a rotational motion of the cam portion 2425 in a substantially opposite direction (e.g., in response to a force exerted by the spring 2427, as described above) until the second cam 2435 is rotated to a position in which the ratchet portion 2447 is no longer in contact with the rack portion 2437 of the second cam 2435, thereby allowing the spring 2449 to exert a force to rotate the cam follower 2446 in a second angular direction (e.g., an opposite angular direction), as described in further detail herein.

As described above, the handle 2100 is configured to be removably coupled to a cartridge assembly 2500. The cartridge assembly 2500 can be any suitable shape and/or size and can be configured to, at least temporarily, include and/or otherwise house a set of surgical clips, as described in further detail herein. As shown FIGS. 19-28, the cartridge assembly 2500 includes an adapter 2501, an outer sheath 2513, a spine 2520, a first push rod 2530, a second push rod 2540, a coupler 2518, a clamp mechanism 2550, and a set of surgical clips 2590. The outer sheath 2513 has a proximal end portion 2514 and a distal end portion 2515 and defines a lumen 2516 therethrough. The outer sheath 2513 is configured to substantially enclose and/or circumscribe a portion of the spine 2520, the first push rod 2530, the second push rod 2540, and the clamp mechanism 2550. More specifically, a portion of the first push rod 2530, a portion of the second push rod 2540, and a portion of the clamp mechanism 2550 can be movably disposed in the lumen 2516 defined by the outer sheath 2513, while the spine 2520 is fixedly disposed in the lumen 2516. Thus, the first push rod 2530, the second push rod 2540, and the clamp mechanism 2550 can be moved in an axial direction in the lumen 2516 relative to the spine 2520, as described in further detail herein.

Figure 19:
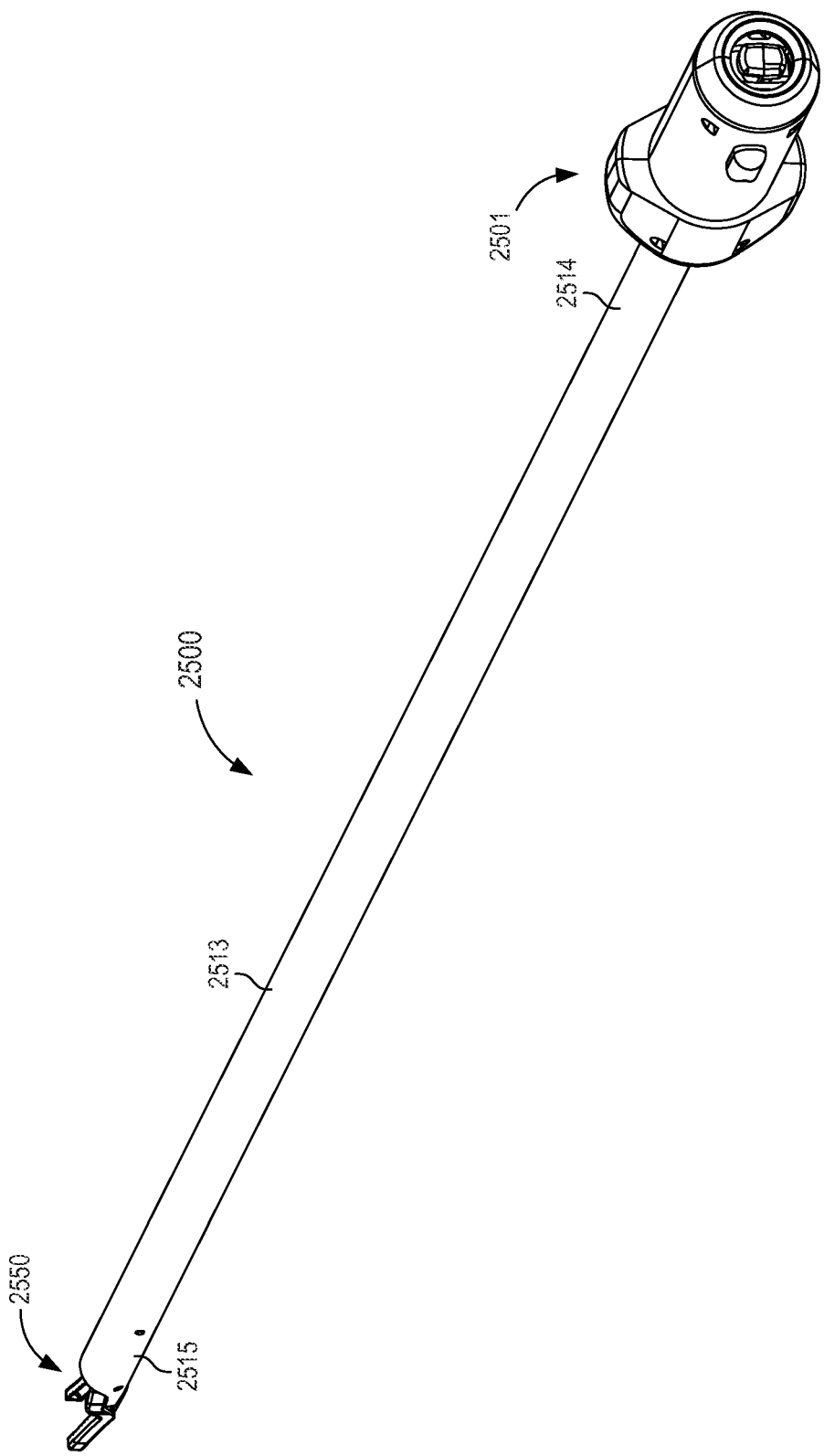
FIG. 19 is a perspective view of a cartridge assembly included in the reposable device of FIG. 2.
Figure 20:
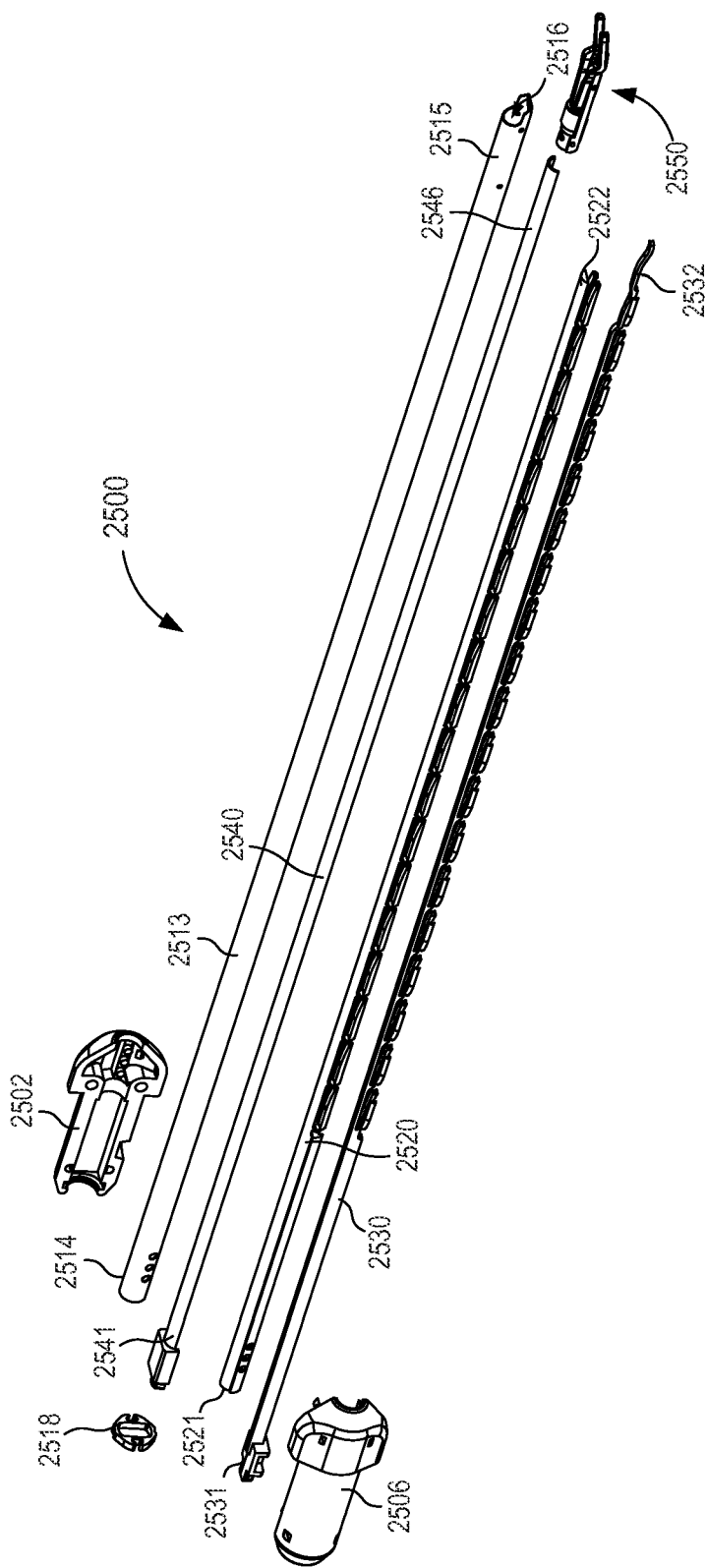
FIG. 20 is an exploded perspective view of the cartridge assembly of FIG. 19.
Figure 21:
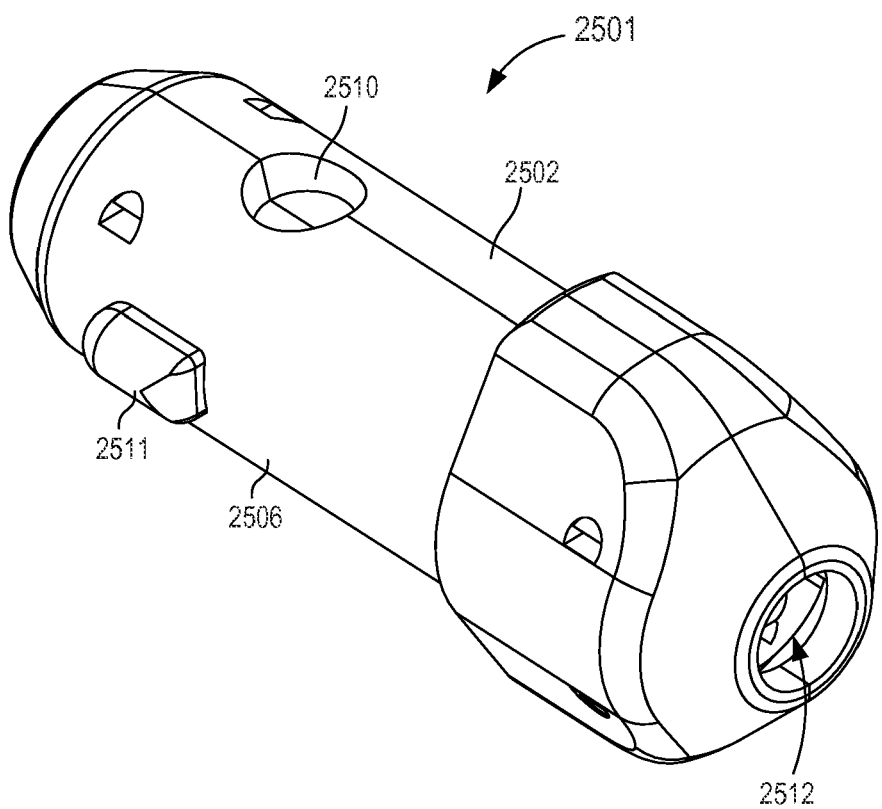
FIG. 21 is a perspective view of an adapter included in the cartridge assembly of FIGS. 19 and 20.

As shown in FIGS. 19-21, the adapter 2501 includes a first member 2502 and a second member 2506 that can be coupled together to collectively define an inner volume 2512 and a recess 2510. Moreover, the arrangement of the first member 2502 and the second member 2506 is such that, when coupled together, the adapter 2501 is substantially open at a proximal end portion and at a distal end portion. The inner volume 2512 is configured to receive the coupler 2518 and a portion (e.g., a proximal end portion) of the outer sheath 2513, the first push rod 2530, the second push rod 2520, and the spine 2520. As shown, for example, in FIG. 21, the second member 2506 includes a protrusion 2511 that extends from an outer surface. The adapter 2501 can be configured to be inserted into the inner volume 2221 defined by the lock mechanism 2200 (as described above) with an orientation that substantially aligns the protrusion 2511 with the notch 2222 defined by the inner surface 2220 of the lock mechanism 2200. Thus, the protrusion 2511 can be, for example, a clocking and/or reference feature that can facilitate the coupling of the cartridge assembly 2500 to the lock mechanism 2200, as described in further detail herein.

The recess 2510 collectively formed and/or defined by the first member 2502 and the second member 2506 is configured to selectively engage the lock member 2250 of the lock mechanism 2200. For example, as described above, the lock actuator 2230 can be moved within the channel 2223 defined by the inner surface 2220 of the body portion 2210 included in the lock mechanism 2200 to move the lock member 2250 relative to the inner surface 2220 between a first position, in which a surface of the lock member 2250 is disposed at a first distance from a portion of the inner surface 2220 defining the channel 2223, and a second position, in which the surface of the lock member 2250 is disposed at a second distance, smaller than the first distance, from the portion of the inner surface 2220. In this manner, the adapter 2501 of the cartridge assembly 2500 can be inserted in the inner volume 2221 defined by the body portion 2210 such that when the lock member 2250 is in the first position, a portion of the lock member 2250 is disposed in the recess 2510 defined by the adapter 2501 to temporarily couple the cartridge assembly 2500 to the lock mechanism 2200.

Figure 22:
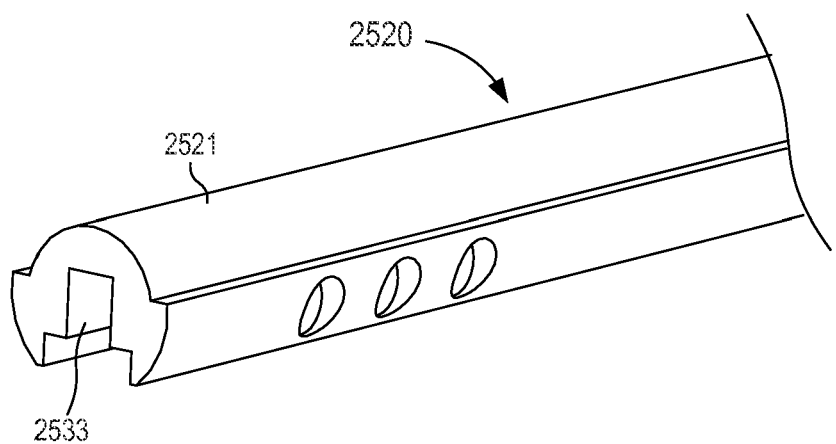
FIG. 22 is a perspective view of a proximal end portion of a spine included in the cartridge assembly of FIGS. 19 and 20.
Figure 23:
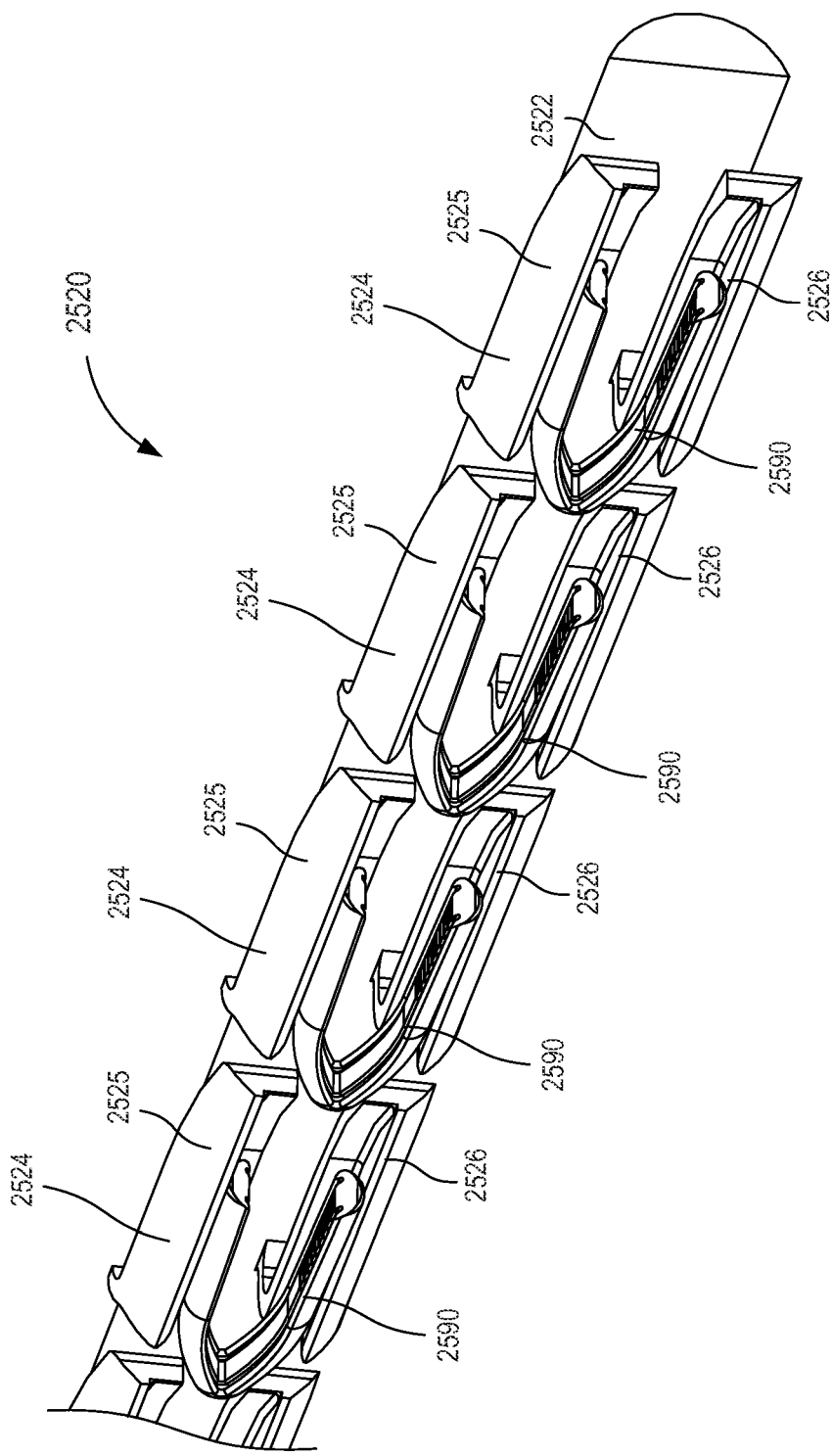
FIG. 23 is a perspective view of a distal end portion of the spine of FIG. 22 coupled to a set of surgical clips included in the cartridge assembly of FIGS. 19 and 20.
Figure 24:
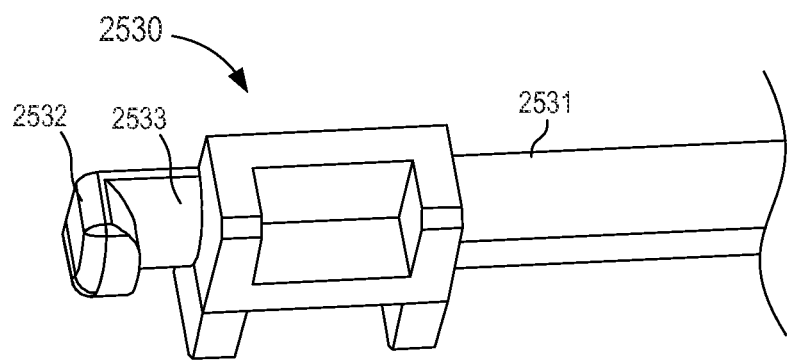
FIGS. 24 and 25 are perspective views of a proximal end portion and a distal end portion, respectively, of a first push rod included in the cartridge assembly of FIGS. 19 and 20.
Figure 25:
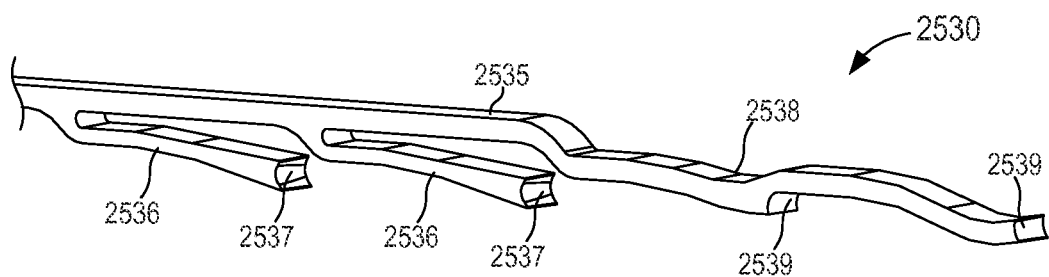

As described above, the spine 2520 of the cartridge assembly 2500 is fixedly disposed in the outer sheath 2513. The spine 2520 has a proximal end portion 2521 (FIG. 22) and a distal end portion 2525 (FIG. 23), and defines a channel 2533 therethrough (FIG. 22). The proximal end portion 2521 is disposed in and/or coupled to the adapter 2501. Thus, the spine 2520 is maintained in a substantially fixed position relative to the adapter. The spine 2520 includes a set of clip retainers 2524 that are linearly arranged along a length of the spine 2520 with each clip retainer 2524 being disposed at a substantially uniform spacing from an adjacent clip retainer 2524. More specifically, as shown in FIGS. 20 and 23, the set of clip retainers 2524 extends into and/or along the distal end portion 2522 of the spine 2520 such that the distal most clip retainer 2524 is disposed substantially at the distal end of the spine 2520. Each clip retainer 2524 includes a first arm 2525 disposed on and/or defining a first side of the channel 2533 and a second arm 2526 disposed on and/or defining a second side of the channel 2533. In this manner, the clip retainers 2524 can selectively receive a surgical clip 2590 to temporarily couple each surgical clip 2590 to a different clip retainer 2524. In some embodiments, the spine 2520 can include, for example, nineteen clip retainers 2524, thereby retaining nineteen surgical clips 2590. Although not shown, in some embodiments, the cartridge assembly 2500 can be configured to retain one surgical clip 2590 in a distal position relative to the spine 2520. Thus, prior to use, the cartridge assembly 2500 can be configured to include and/or retain twenty surgical clips 2590. In other embodiments, the cartridge assembly 2500 can be configured to retain more than twenty surgical clips 2590 or less than twenty surgical clips 2590.

As described above, a portion of the first push rod 2530 of the cartridge assembly 2500 is disposed in the outer sheath 2513 and can be moved in an axial direction between a first position (e.g., a proximal position) and a second position (e.g., a distal position). As shown in FIGS. 22 and 23, respectively, the first push rod 2530 has a proximal end portion 2531 and a distal end portion 2535. The proximal end portion 2531 is movably disposed in the adapter 2501 and is configured to be selectively coupled to the first coupling member 2380 of the drive mechanism 2300. More specifically, as shown in FIG. 22, the proximal end portion 2531 includes a substantially L-shaped protrusion 2532 that extends in a proximal direction. The substantially L-shaped protrusion 2532 (referred to henceforth as "protrusion") includes a substantially radiused surface that defines a notch 2533 that is similarly radiused. In this manner, the adapter 2501 can be positioned in the inner volume 2221 of the lock mechanism 2200 such that the protrusion 2532 of the first push rod 2530 is substantially adjacent to the extension 2383 of the first coupling member 2380 of the drive mechanism 2300. More specifically, the adapter 2501 can be placed in an orientation relative to the lock mechanism 2200 in which a portion of the protrusion 2532 is disposed in the recess 2384 defined by the extension 2383, and a portion of the extension 2383 is disposed in the notch 2533 defined by the protrusion 2532. Thus, the first push rod 2530 of the cartridge assembly 2500 can be coupled to the first coupling member 2380 of the drive mechanism 2300 when the cartridge assembly 2500 is coupled to the handle 2100.

As shown in FIGS. 20 and 23, the first push rod 2530 includes a set of push arms 2536 that are linearly arranged along a length of the first push rod 2530 with each push arm 2536 being disposed at a substantially uniform spacing from an adjacent push arm 2536. Each push arm 2536 includes an engagement surface 2537 that is configured to be placed in contact with a proximal surface of a different surgical clip 2590 included in the cartridge assembly 2500. As shown in FIG. 23, the set of push arms 2536 extend into and/or along the distal end portion 2535 of the first push rod 2530. Moreover, the distal end portion 2535 of the first push rod 2530 includes and/or forms an extension 2538 that includes a pair of engagement surfaces 2539 that are configured to engage a proximal surface of a surgical clip 2590 in a similar manner to the engagement surface 2537 of each push arm 2536. In this manner, the engagement surfaces 2537 and 2539 can contact a different surgical clip 2590 (e.g., temporarily retained by the spine 2520 and/or other portion of the cartridge assembly 2500) and can be configured to advance the surgical clips 2590 relative to the spine 2520 in response to force exerted on the first push rod, as shown, for example in FIG. 27.

Figure 26:
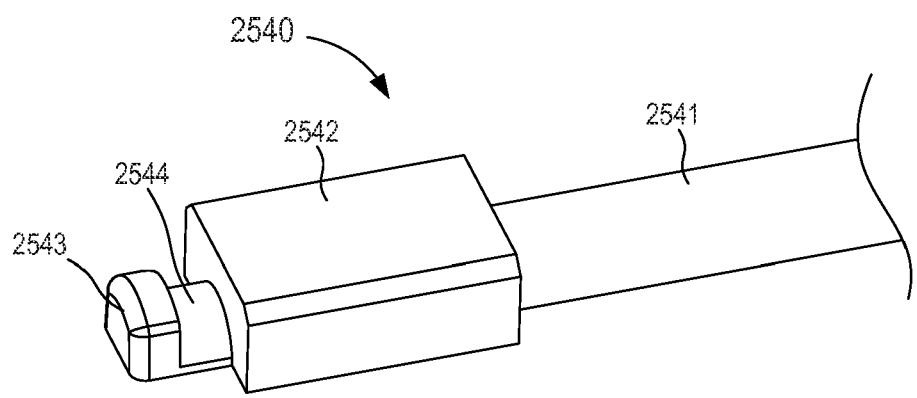
FIG. 26 is a perspective view of a proximal end portion of a second push rod included in the cartridge assembly of FIGS. 19 and 20.
Figure 27:
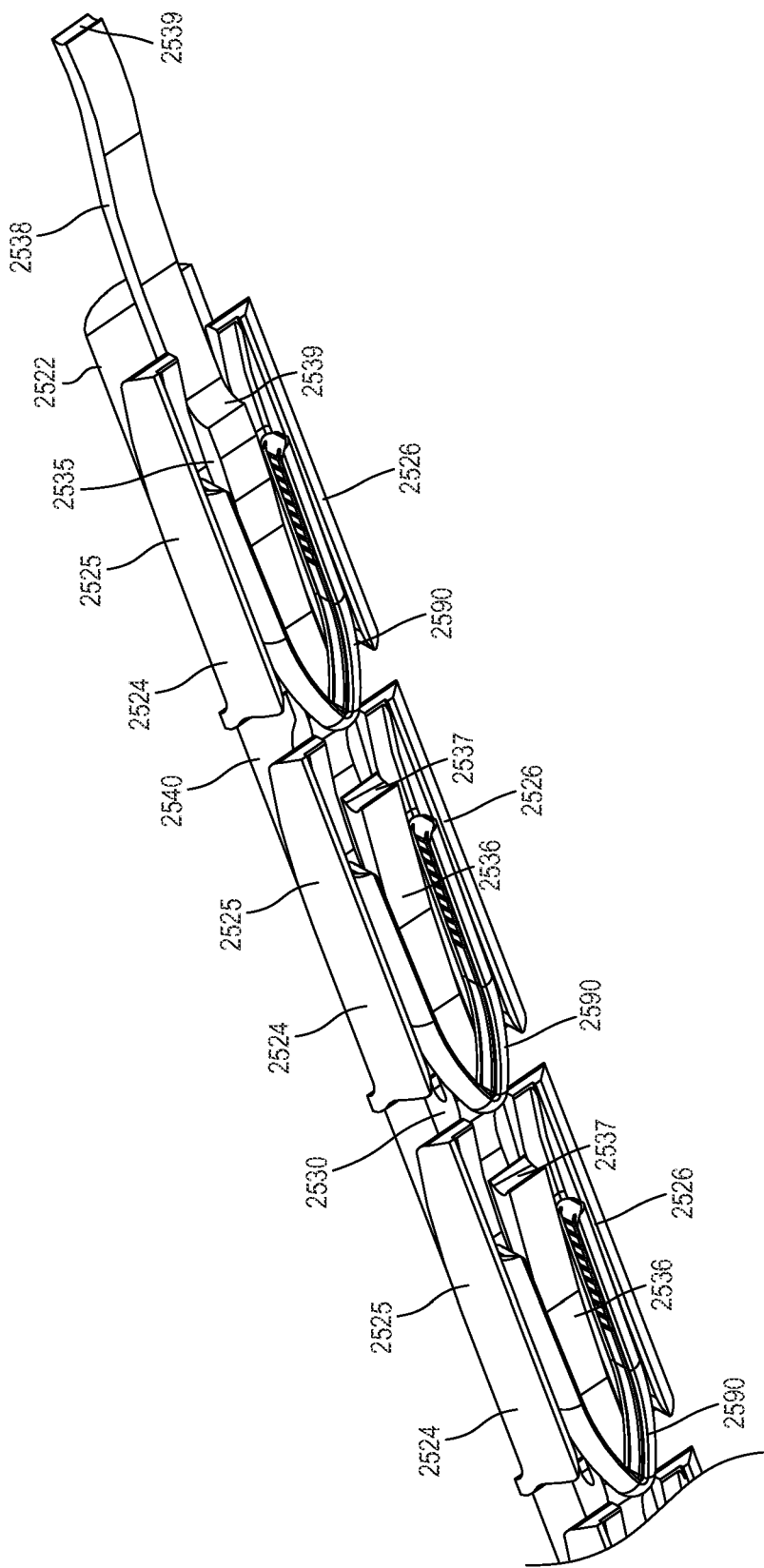
FIG. 27 is a perspective view of the distal end portion of the spine illustrated in FIG. 23 and the distal end portion of the first push rod illustrated in FIG. 25.

As described above, a portion of the second push rod 2540 of the cartridge assembly 2500 is disposed in the outer sheath 2513 and can be moved in an axial direction between a first position (e.g., a proximal position) and a second position (e.g., a distal position). The second push rod 2540 has a proximal end portion 2541 and a distal end portion 2545. The distal end portion 2545 is configured to extend through the lumen 2516 defined by the outer sheath 2531 to contact a portion of the clamp mechanism 2550, as described in further detail herein. The proximal end portion 2541 of the second push rod 2540 includes an adapter 2542. The adapter 2542 can be fixedly coupled to the proximal end portion of 2541 via, for example, a weld, an adhesive, a friction fit, a press fit, and/or the like. As shown in FIG. 26, the adapter 2542 includes a substantially L-shaped protrusion 2543 that extends in a proximal direction. The substantially L-shaped protrusion 2543 (referred to henceforth as "protrusion") includes a substantially radiused surface that defines a notch 2544 that is similarly radiused. The protrusion 2543 can be substantially similar in form and function to the protrusion 2532 of the first push rod 2530. Thus, the adapter 2542 can be positioned in the inner volume 2221 of the lock mechanism 2200 such that the protrusion 2544 of the adapter 2542 is substantially adjacent to the extension 2396 of the second coupling member 2390. Moreover, the adapter 2501 can be placed in an orientation relative to the lock mechanism 2200 to dispose a portion of the protrusion 2543 in the recess 2397 defined by the extension 2396 and a portion of the extension 2396 in the notch 2544 defined by the protrusion 2543, thereby coupling the second push rod 2540 of the cartridge assembly 2500 to the second coupling member 2390 of the drive mechanism 2300.

The coupler 2518 of the cartridge assembly 2500 is configured to be fixedly disposed in the inner volume 2512 of the adapter 2501. The coupler 2518 defines an opening 2519 that is configured to receive, for example, the protrusion 2532 of the first push rod 2530 and the protrusion 2543 of the adapter 2542. More specifically, the protrusion 2532 of the first push rod 2530 and the protrusion 2543 of the adapter 2542 can be disposed in the opening 2519 such that the coupler 2518 is disposed about the notch 2533 defined by the protrusion 2532 of the first push rod 2530 and the notch 2544 defined by the protrusion 2543 of the adapter 2542. Thus, the coupler 2518 can retain the first push rod 2530 in a substantially fixed axial position relative to adapter 2542 and hence, the second push rod 2540 (or vice versa) and/or the remaining portions of the cartridge assembly 2500. As such, an axial movement of the first push rod 2530 and the adapter 2542 that can otherwise result in an axial misalignment of the first push rod 2530 and/or the adapter 2542 relative to the first coupling member 2380 and the second coupling member 2390, respectively, can be reduced and/or substantially eliminated.

Figure 28:
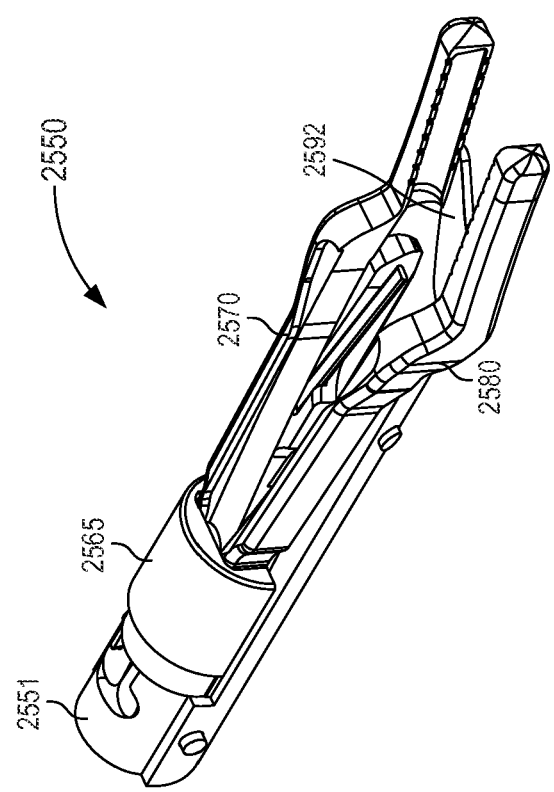
FIG. 28 is a perspective view and FIG. 29 is a top view of a clamp mechanism included in the cartridge assembly of FIGS. 19 and 20.
Figure 29:
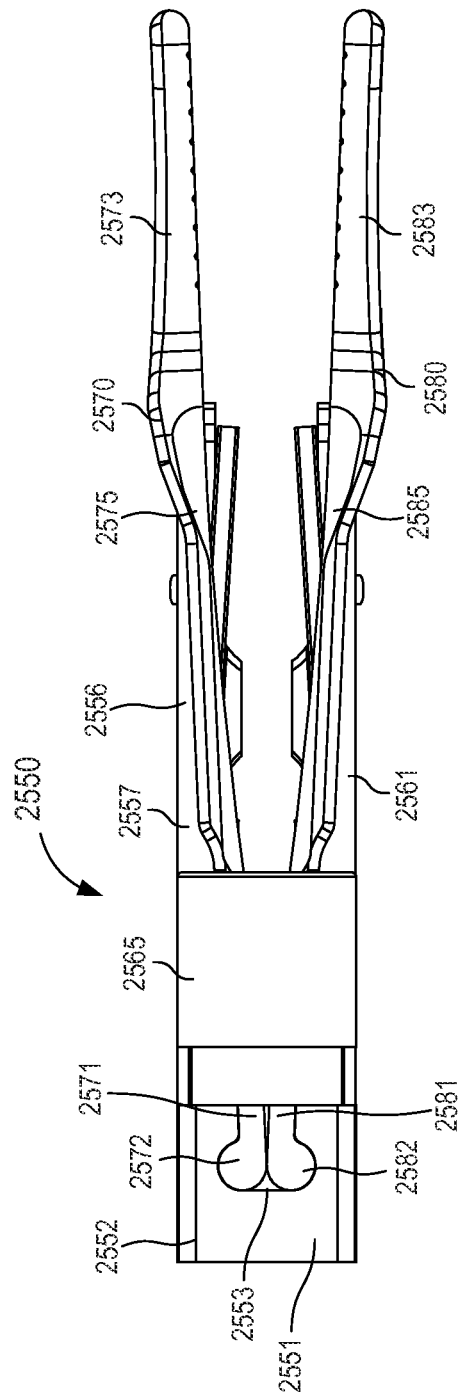
Figure 30:
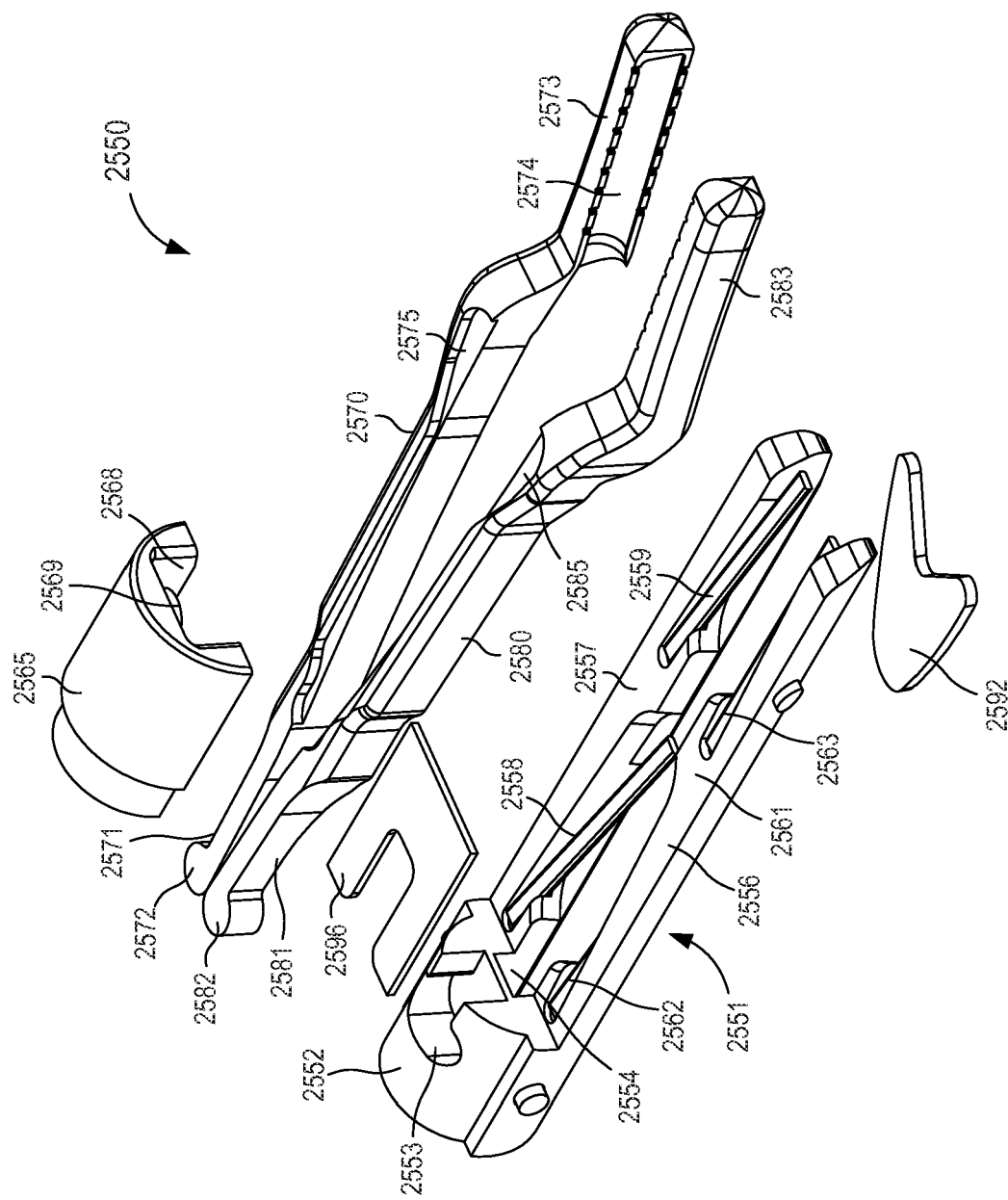
FIG. 30 is an exploded perspective view of the clamp mechanism of FIGS. 28 and 29.

The clamp mechanism 2550 of the cartridge assembly 2500 is coupled to a distal end portion 2515 of the outer sheath 2513 and is configured to sequentially receive the set of surgical clips 2590 (i.e., one after the other). As shown in FIGS. 28-30, the clamp mechanism 2550 includes a shoe 2551, a cinch member 2565, a first clamp member 2570, a second clamp member 2580, and a guard 2592. The shoe 2551 is coupled to the distal end portion 2515 of the outer sheath 2513 such that at least a portion of the shoe 2551 is maintained in a substantially fixed position within the lumen 2516 defined by the outer sheath 2513 (see e.g., FIG. 41). The shoe 2551 includes a coupling portion 2552 and a bifurcated portion 2556. The coupling portion 2552 defines a recess 2553 and a channel 2554 (FIG. 30). The recess 2553 is configured to receive a proximal end portion 2571 of the first clamp member 2570 and a proximal end portion 2581 of the second clamp member 2580, as described in further detail herein. The channel 2554 extends through the coupling portion 2554 such that the distal end portion 2535 of the first push rod 2530 and the set of surgical clips 2590 can advance therethrough, as described in further detail herein.

The bifurcated portion 2556 of the shoe 2551 extends in a distal direction from the coupling portion 2552. As shown in FIG. 30, the bifurcated portion 2556 includes a first arm 2557 and a second arm 2561 that collectively define a space therebetween. The first arm 2557 includes a first guide portion 2558 and a second guide portion 2559. Similarly, the second arm 2561 includes a first guide portion 2562 and a second guide portion 2563. The second arm 2561 can be substantially similar to the first arm 2557 and arranged in a substantially mirrored orientation relative to the first arm 2557. Thus, a discussion of the form and function of the first arm 2557 can apply to the second arm 2561 of the bifurcated portion 2556 unless explicitly stated otherwise.

The first guide portion 2558 and the second guide portion 2559 can be any suitable device, assembly, and/or the like that can selectively engage the set of surgical clips 2590. For example, in some embodiments, the first guide portion 2558 and the second guide portion 2559 can include a set of bias members (e.g., tabs, fingers, clips, clamps, extensions, and/or the like) that extend from a surface of the first arm 2557. In such embodiments, the bias members can include and/or can be formed from a relatively flexible material that can allow the bias members to bend or flex when placed in contact with a surgical clip 2590. Moreover, the bending and/or flexing of the bias members can increase an internal stress in the bias members that can, in turn, exert a reaction force. Thus, as a surgical clip 2590 is advanced in a distal direction along a length of the shoe 2551, the first guide portion 2258 and/or the second guide portion 2559 can guide, direct, limit, and/or otherwise influence the motion of the surgical clip 2590, as described in further detail herein.

The cinch member 2565 of the clamp mechanism 2550 can be any suitable shape and/or size. The cinch member 2565 is configured to be in contact with the distal end portion 2546 of the second push rod 2540. In this manner, movement of the second push rod 2540 in the distal direction and/or the proximal direction can move the cinch member 2565 is a similar and concurrent manner relative to the shoe 2551, as described in further detail herein. As shown in FIG. 30, the cinch member 2565 defines a notch 2568 and includes and/or forms a protrusion 2569 extending therefrom. The first clamp member 2570 and the second clamp member 2580 are movably disposed in the notch 2568 defined by the cinch member 2565. Similarly stated, the cinch member 2565 can be disposed about the first clamp member 2570 and about the second clamp member 2580 and moved between a first position (e.g., a proximal position) and a second position (e.g., a distal position) relative to the first clamp member 2570 and the second clamp member 2580. Expanding further, the cinch member 2565 can be disposed about the first clamp member 2570 and the second clamp member 2580 such that the protrusion 2569 is movably disposed in a track 2575 and 2585 defined by the first clamp member 2570 and the second clamp member 2580, respectively. As shown in FIG. 30, the cinch member 2565 can be coupled to a base plate 2596 that can, for example, be in contact with a surface of the shoe 2551 to facilitate the movement of the cinch member 2565 between its first position and its second position. In this manner, the cinch member 2565 can be configured to pivot the first clamp member 2570 and the second clamp member 2580 relative to the shoe 2551, as described in further detail herein.

The first clamp member 2570 of the clamp mechanism 2550 has the proximal end portion 2571 and a distal end portion 2573. As described above, the proximal end portion 2571 of the first clamp member 2570 is disposed in the recess 2553 defined by the coupling portion 2552 of the shoe 2551. More specifically, the proximal end portion 2571 includes a substantially rounded protrusion 2572 that is disposed in the recess 2553 and that is configured to define an axis about which the first clamp member 2570 can pivot, as described in further detail herein. As shown, for example, in FIG. 19, the clamp mechanism 2550 can be disposed in the lumen 2516 defined by the outer sheath 2513 such that the distal end portion 2573 of the first clamp member 2575 extends beyond the distal end portion 2515 of the outer sheath 2513 (e.g., in the distal direction). The distal end portion 2573 of the first clamp member 2570 can be, for example, substantially hollow and can be configured to sequentially receive the surgical clips 2590 (i.e., one after another). Similarly stated, the distal end portion 2573 defines a recess 2574 that can selectively receive the surgical clips 2590, as described in further detail herein.

The second clamp member 2580 of the clamp mechanism 2550 has the proximal end portion 2571 and a distal end portion 2583. The second clamp member 2571 can be substantially similar in form and/or function to the first clamp member 2570 and can be arranged in a substantially mirrored orientation, as shown in FIGS. 28 and 29. As such, the proximal end portion 2581 of the first clamp member 2570 includes a substantially rounded protrusion 2582 that is disposed in the recess 2553 of the coupling portion 2552 and that is configured to define an axis about which the second clamp member 2580 can pivot. As described above with reference to the first clamp member 2573, the distal end portion 2583 of the second clamp member 2580 defines a recess 2584 that can selectively receive the surgical clips 2590. Moreover, the first clamp arm 2570 and the second clamp arm 2580 can be urged to pivot about the protrusions 2572 and 2582, respectively, to increase or decrease a distance defined between the distal end portion 2573 of the first clamp arm 2570 and the distal end portion 2583 of the second clamp arm 2580.

As shown in FIG. 29, the distal end portion 2573 of the first clamp member 2570 can extend beyond a surface of the first arm 2557 (e.g., a side) of the shoe 2551. Said another way, the distal end portion 2573 of the first clamp member 2750 can extend beyond an outer surface of the first arm 2557 in a substantially perpendicular direction relative to a longitudinal centerline (not shown) defined by the shoe 2551. Similarly, the distal end portion 2583 of the second clamp member 2580 can extend beyond an outer surface of the second arm 2561 of the shoe 2551 in a substantially perpendicular direction relative to the longitudinal centerline. Moreover, the distal end portion 2573 of the first clamp member 2570 and the distal end portion 2583 of the second clamp 2580 can extend beyond an outer surface of the outer sheath 2515 in a substantially perpendicular direction relative to a longitudinal centerline defined by the outer sheath 2515. Thus, any sized surgical clip 2590 that can be disposed in the outer sheath 2590 can be advanced in the distal direction to be disposed in a space defined between the recess 2574 of the first clamp member 2570 and the recess 2584 of the second clamp member 2580. Said another way, the arrangement of the clamp mechanism 2550 can be such that the space defined between the recess 2574 of the first clamp member 2570 and the recess 2584 of the second clamp member 2580 does not limit and/or constrain a size of a surgical clip included in the cartridge assembly 2500.

Figure 31:
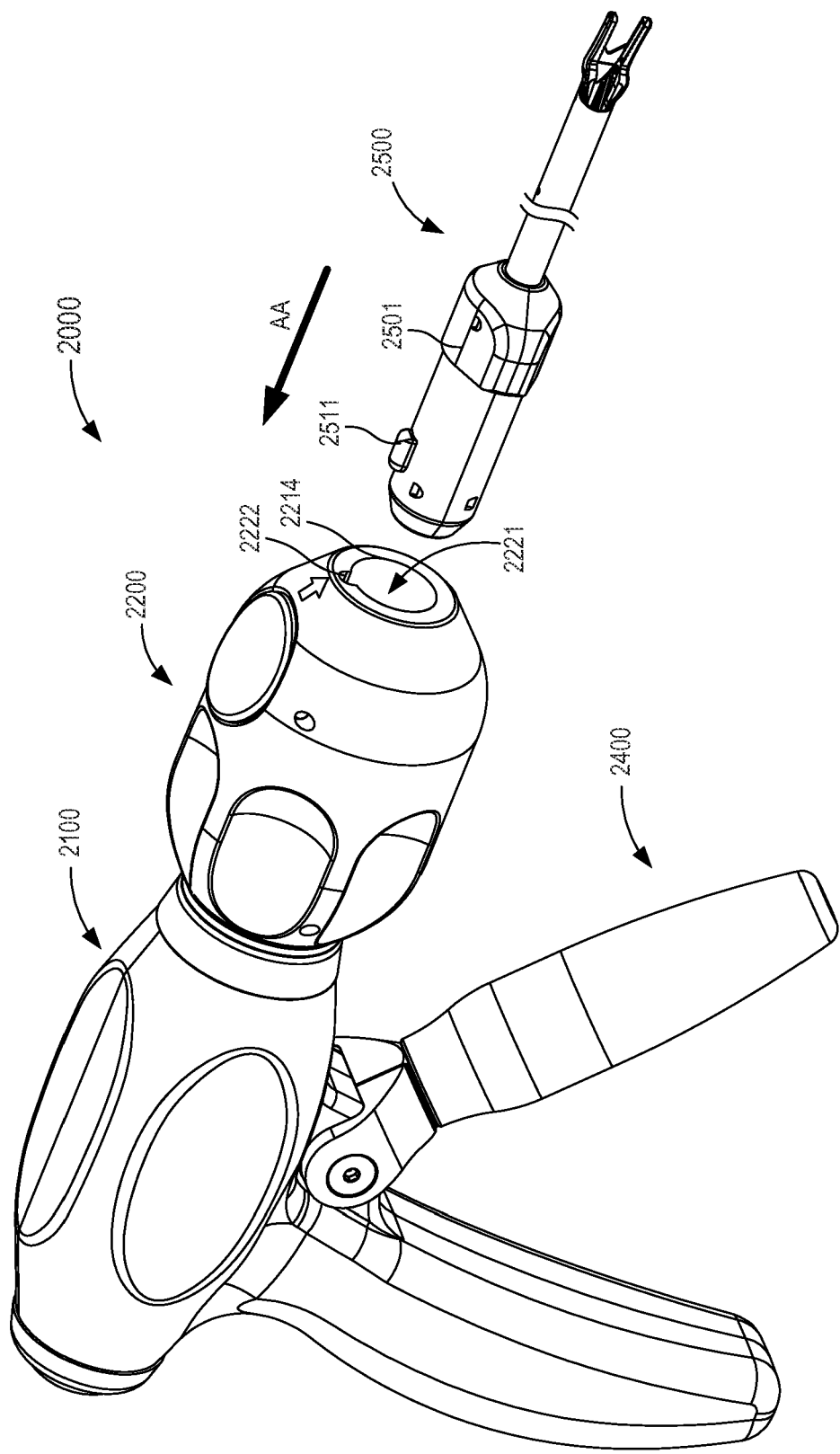
FIG. 31 is a perspective view of the reposable device of FIG. 2 prior to coupling the cartridge assembly of FIG. 19 to the universal handle of FIG. 3.
Figure 32:
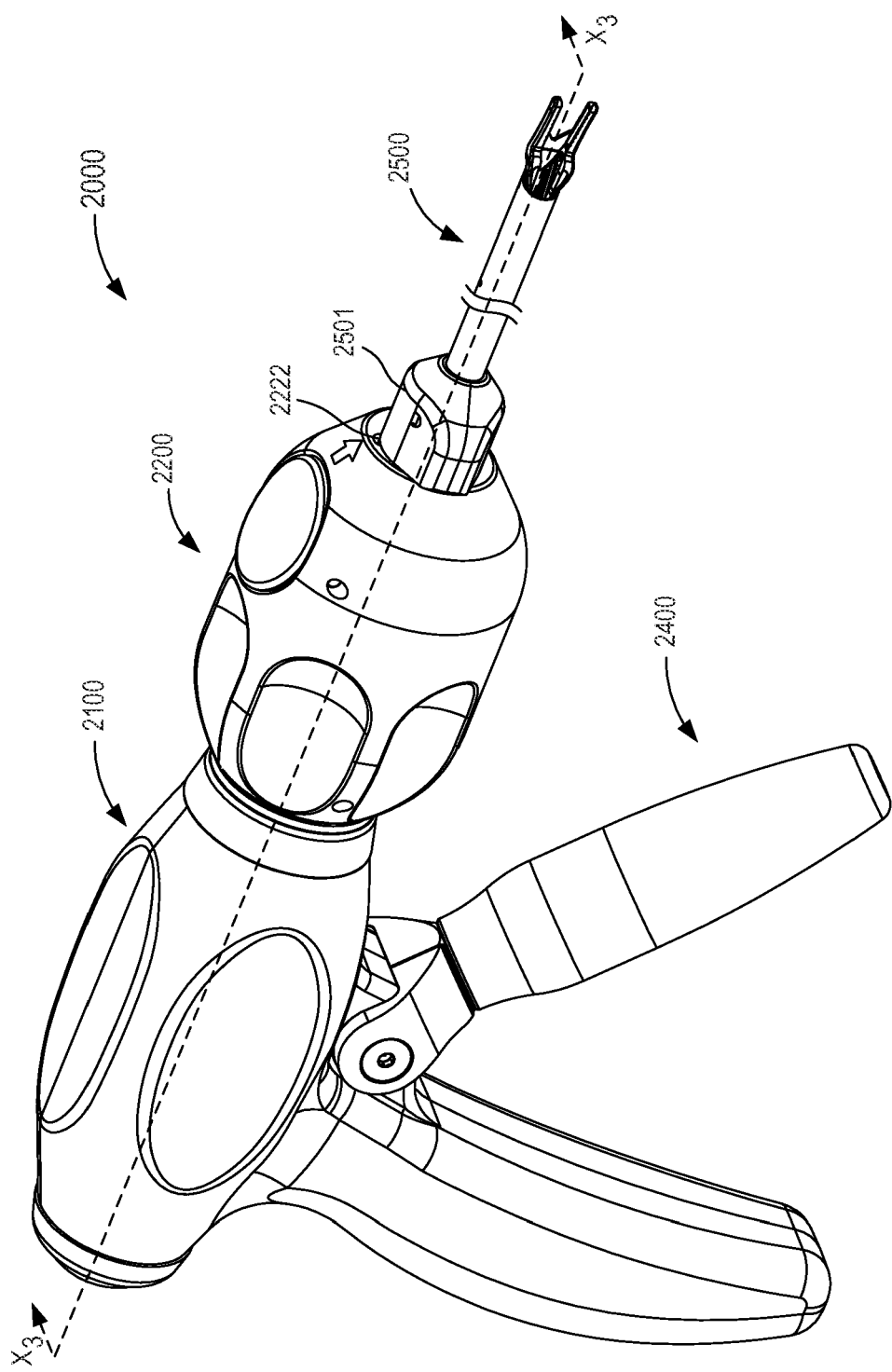
FIG. 32 is a perspective view of the reposable device of FIG. 2 in a first configuration.

The use and/or function of the reposable device 2000 (FIGS. 2-30) is described herein with reference to FIGS. 31-46. In use, a user (e.g., a surgeon, a doctor, a physician, a technician, etc.) can engage the handle 2100 and the cartridge assembly 2500 to removably couple the cartridge assembly 2500 to the handle 210. For example, as shown in FIG. 31, the cartridge assembly 2500 can be moved in a direction towards the lock mechanism 2200 of the handle 2100, as indicated by the arrow AA. More specifically, the user can place the cartridge assembly 2500 in a first orientation relative to the lock mechanism 2200 such that the protrusion 2511 of the adapter 2501 is substantially aligned with the notch 2222 defined and/or formed by the inner surface 2220 of the body portion 2210 included in the lock mechanism 2200. In this manner, the user can insert a portion of the adapter 2501 into the opening 2214 defined by the body portion 2210 to place the reposable device in a first configuration, as shown, for example, in FIG. 32.

Figure 33:
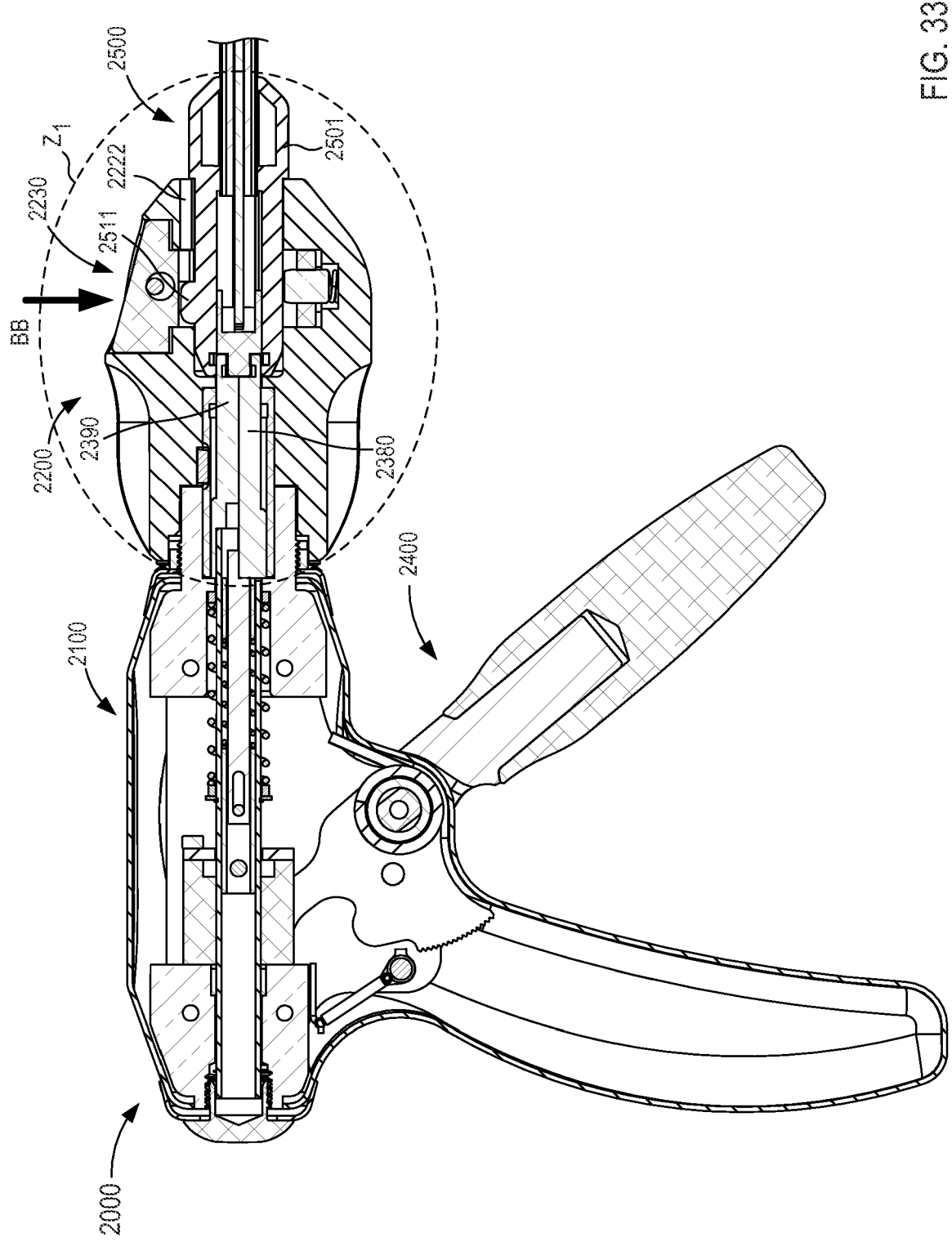
FIG. 33 is a cross-sectional view of a portion of the reposable device of FIG. 2 taken along the line $X_3$-$X_3$ in FIG. 32.
Figure 34:
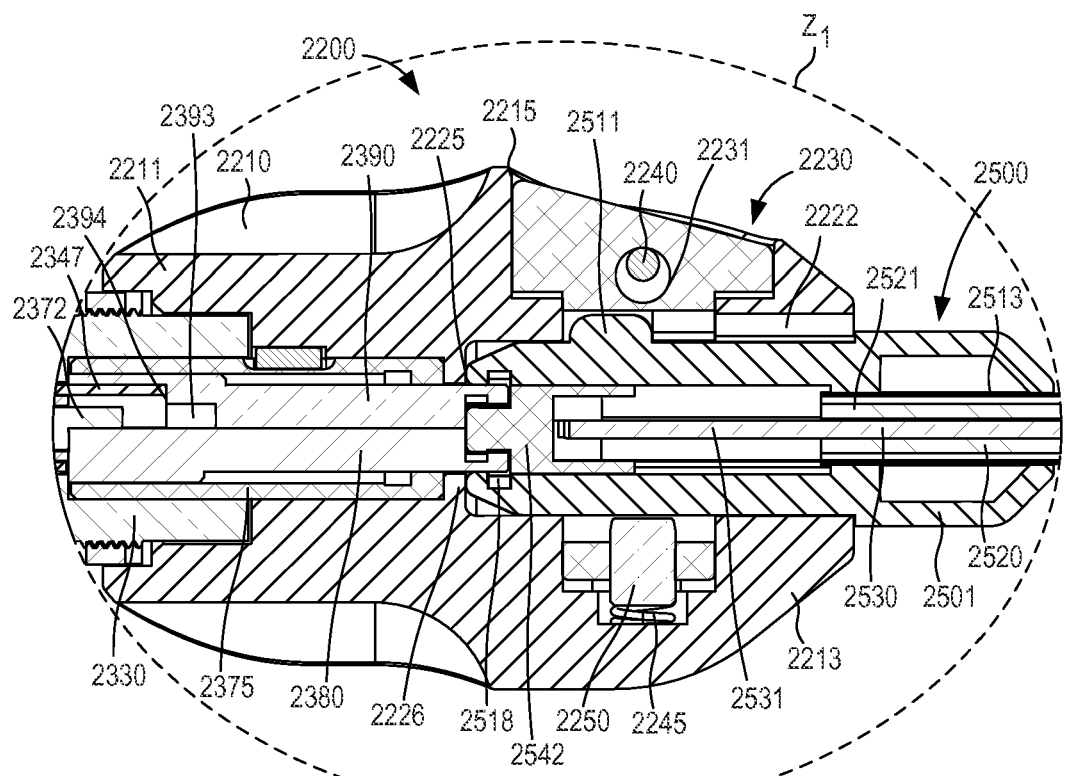
FIG. 34 is an enlarged cross-sectional view of a portion of the reposable device of FIG. 2, identified by the region $Z_1$ in FIG. 33.

In a substantially concurrent process and/or after a portion of the adapter 2501 is inserted into the opening 2214 defined by the body portion 2210 of the lock mechanism 2200, the user can, for example, exert a force on the lock actuator 2230 to move the lock actuator 2300 within the channel 2223 defined by the inner surface 2220 such that the opening 2233 defined by the inner surface 2232 of the lock actuator 2230 is at least partially aligned with the opening 2214 of the body portion 2210 of the lock mechanism 2200, as indicated by the arrow BB in FIG. 33. As such, the lock member 2250 included in and/or coupled to the lock actuator 2230 is moved relative to the inner surface 2220 to, for example, the second position, in which the surface of the lock member 2250 is disposed at the second distance from the portion of the inner surface 2220 (as described above). In this manner, the adapter 2501 of the cartridge assembly 2500 can be inserted into the inner volume 2221 defined by the body portion 2210 to a position in which a proximal surface of the adapter 2501 is substantially placed in contact with the distal shoulder 2224 formed by the medial portion 2226 of the inner surface 2220, as shown, for example, in FIGS. 33 and 34. Although the lock actuator 2230 is described above as being moved by the user, in other embodiments, the adapter 2501 can engage the lock member 2250 when inserted into the inner volume 2221 of the body portion 2210 and as such, can exert a force on the lock member 2250 to move the lock actuator 2230 in the BB direction.

Figure 35:
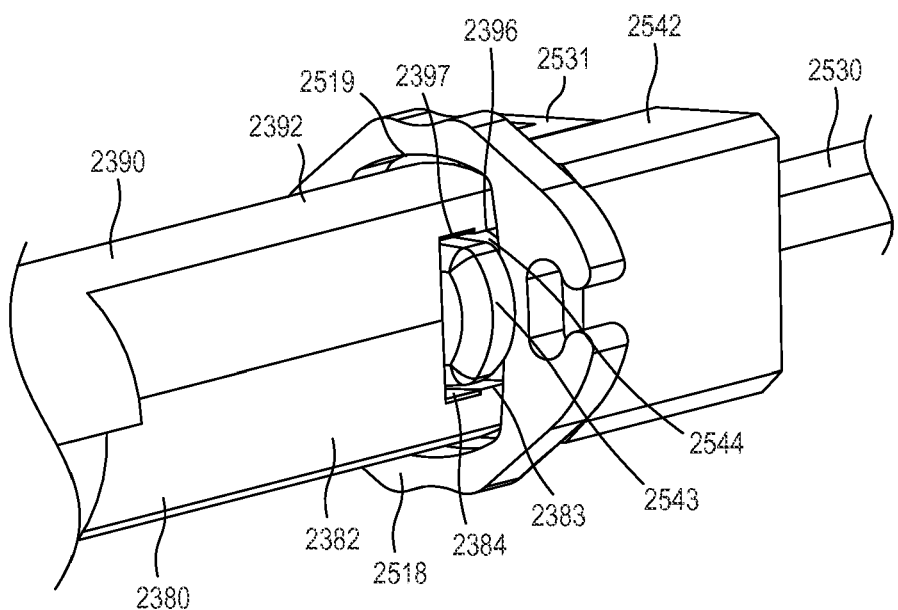
FIG. 35 is a perspective view of a portion of the cartridge assembly of FIGS. 19-20 being coupled to a portion of the drive mechanism of FIG. 10.
Figure 36:
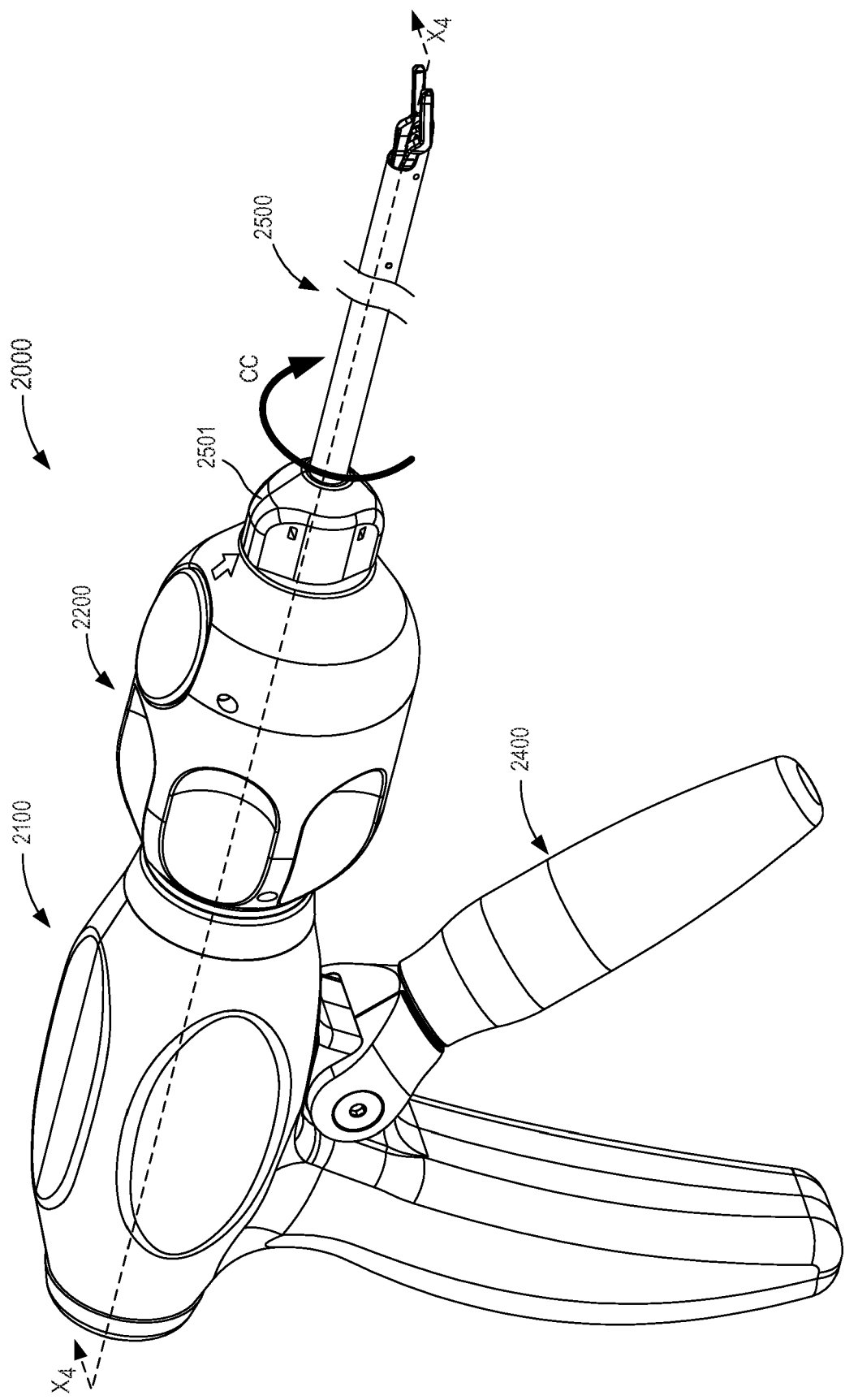
FIG. 36 is a perspective view of the reposable device of FIG. 2 in a second configuration.

As shown in FIG. 35, with the proximal surface of the adapter 2501 in contact with distal shoulder 2224, the proximal end portion 2531 of the first push rod 2530 and the adapter 2542 of the second push rod 2540 can be placed in a desired position relative to the distal end portion 2382 of the first coupling member 2380 and the distal end portion 2395 of the second coupling member 2390, respectively. More particularly, the protrusion 2532 (not shown) included in the proximal end portion 2531 of the first push rod 2530 can be axially aligned with the extension 2383 included in the distal end portion 2382 of the first coupling member 2380 and the protrusion 2543 included in the adapter 2542 of the second push rod 2540 can be axially aligned with the extension 2396 included in the distal end portion 2395 of the second coupling member 2590.

Figure 37:
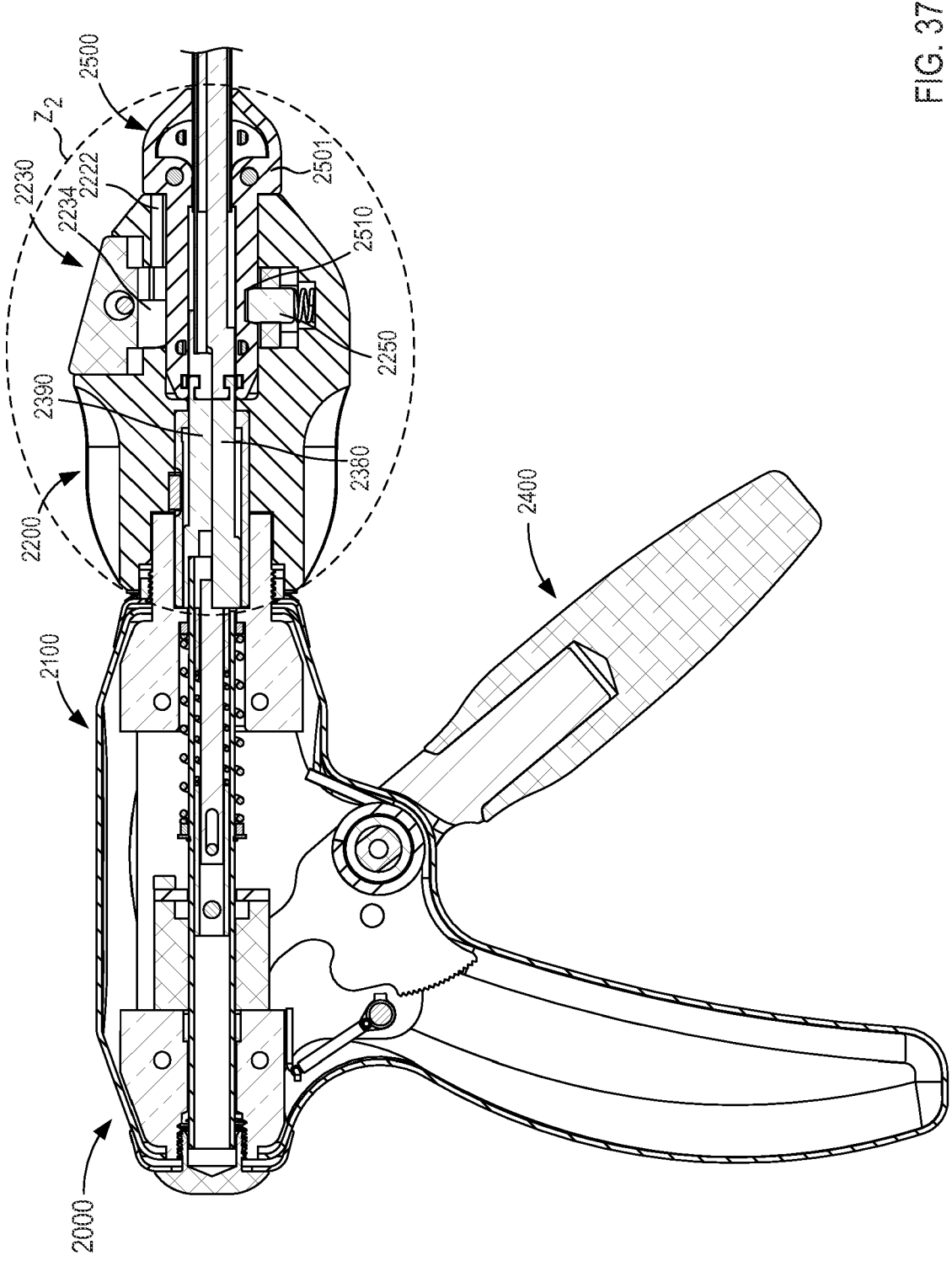
FIG. 37 is a cross-sectional view of a portion of the reposable device of FIG. 2 taken along the line $X_4$-$X_4$ in FIG. 36, illustrating the drive mechanism of FIG. 10 in a first configuration and the cartridge assembly of FIGS. 19 and 20 in a first configuration.
Figure 38:
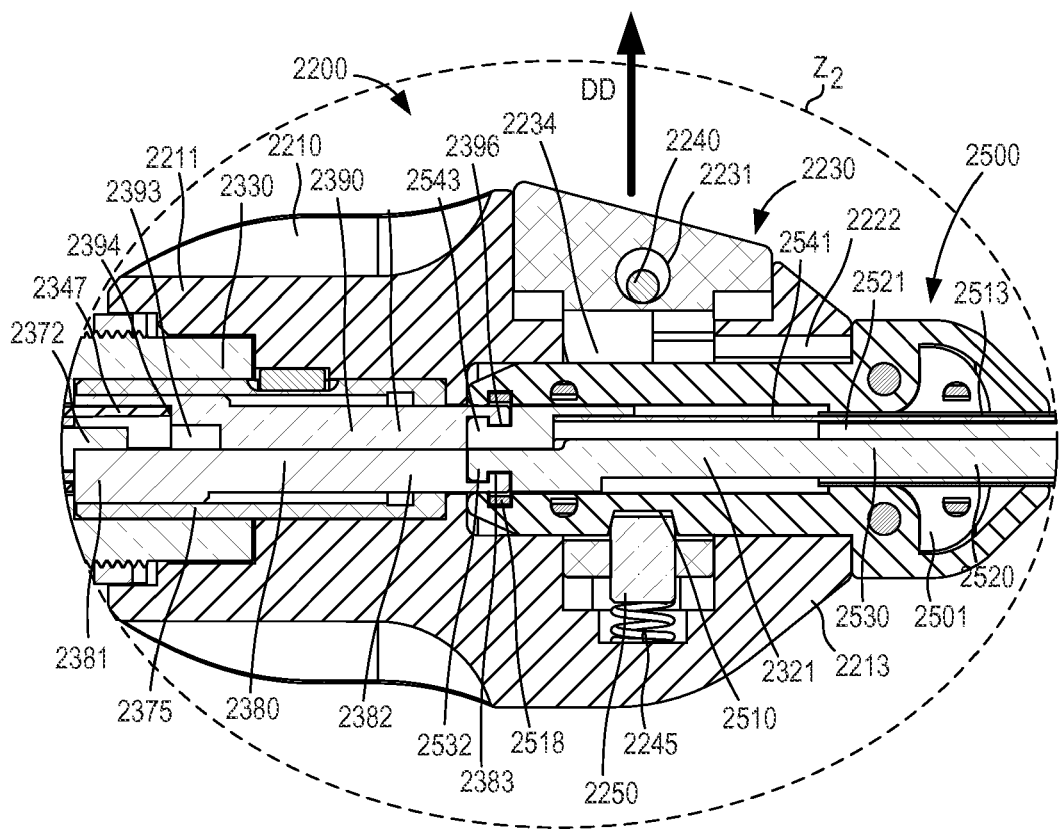
FIG. 38 is an enlarged cross-sectional view of a portion of the reposable device of FIG. 2, identified by the region $Z_2$ in FIG. 37.

With the cartridge assembly 2500 placed in the desired position relative to the lock mechanism 2300 the user can engage the reposable device 2000 to transition the reposable device 2000 from the first configuration to a second configuration. For example, the user can manipulate the cartridge assembly 2500 by rotating the cartridge assembly 2500 from the first orientation relative to the handle 2100 to a second orientation relative to the handle 2100, as indicated by the arrow CC in FIG. 36. In this manner, the protrusion 2511 of the adapter 2501 can be rotated in the channel 2234 defined by the inner surface 2232 of the lock actuator 2230 until the cartridge assembly 2500 is rotated to the second orientation. In addition, as shown in FIGS. 37 and 38, when the cartridge assembly 2500 is placed in the second orientation relative to the handle 2100, the recess 2510 can be substantially aligned with the lock member 2250 of the lock actuator 2230. As such, the force exerted to move the lock actuator 2230 in the channel 2223 defined by the inner surface 2220 of the body portion 2210 can be removed and thus, the lock actuator 2230 can be moved in a substantially opposite direction in the channel 2223, as indicated by the arrow DD in FIG. 38. For example, in some instances, the user can disengage the lock actuator 2230 to remove the force. In other instances, the alignment of the recess 2510 of the adapter 2501 with the lock member 2250 is such that a surface of the adapter 2501 that previously exerted a force of the lock member 2250 to maintain the lock member 2250 in its second position is removed. Thus, the bias members 2245 can exert a force that can move the lock actuator 2230 in the DD direction. In this manner, the lock member 2250 can be moved from its second position to its first position (as described above) such that a portion of the lock member 2250 is disposed in the recess 2510 defined by the adapter 2501, as shown in FIGS. 37 and 38. Therefore, the lock actuator 2230 can temporarily retain the adapter 2501 in a substantially fixed position relative to the lock mechanism 2200 (e.g., a substantially fixed axial position and a substantially fixed angular position), thereby temporarily coupling the cartridge assembly 2500 to the handle 2100.

Figure 39:
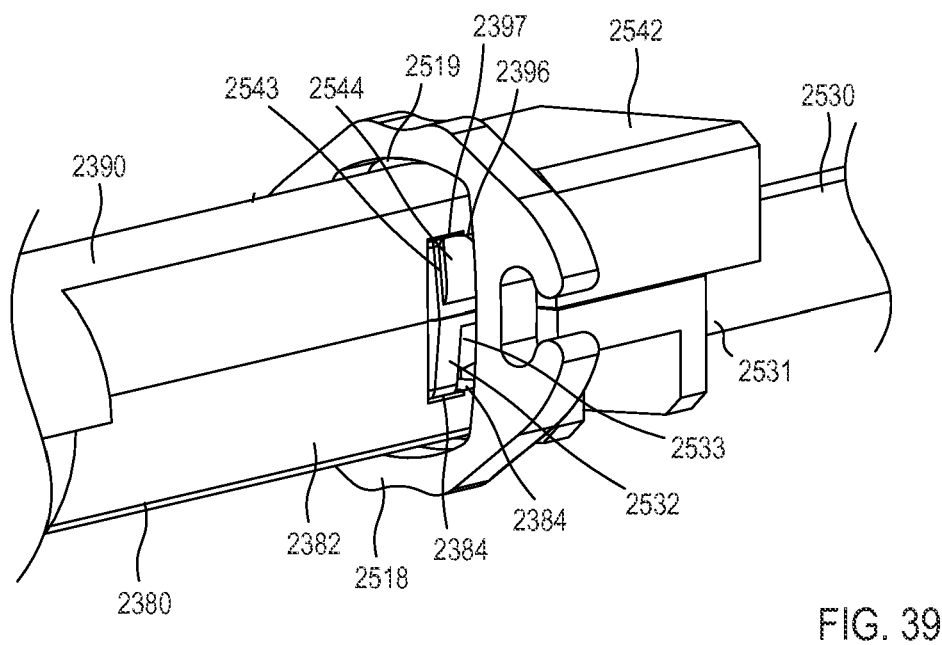
FIG. 39 is a perspective view of a portion of the cartridge assembly of FIGS. 19 and 20 being coupled to a portion of the drive mechanism of FIG. 10.

The rotation of the cartridge assembly 2500 from its first orientation to its second orientation as described above, also rotates the proximal end portion 2531 of the first push rod 2530 and the adapter 2542 of the second push rod 2540 relative to the distal end portion 2382 of the first coupling member 2380 and the distal end portion 2395 of the second coupling member 2390, respectively. For example, as described above with reference to FIG. 35, the protrusion 2532 included in the proximal end portion 2531 of the first push rod 2530 is axially aligned with the extension 2383 included in the distal end portion 2382 of the first coupling member 2380 and the protrusion 2543 included in the adapter 2542 of the second push rod 2540 is axially aligned with the extension 2396 included in the distal end portion 2395 of the second coupling member 2590 when the cartridge assembly 2500 is disposed in the inner volume 2221 of the body portion 2210. Thus, as shown in FIG. 39, the first push rod 2530 of the cartridge assembly 2500 is rotated to an orientation relative to the first coupling member 2380 of the drive mechanism 2300 in which the portion of the protrusion 2532 is disposed in the recess 2384 defined by the extension 2383, and the portion of the extension 2383 is disposed in the notch 2533 defined by the protrusion 2532 (as described above). Similarly, the second push rod 2540 of the cartridge assembly 2500 is rotated to an orientation relative to the second coupling member 2390 of the drive mechanism 2300 in which the portion of the protrusion 2543 of the adapter 2542 is disposed in the recess 2397 defined by the extension 2396, and the portion of the extension 2396 is disposed in the notch 2544 defined by the protrusion 2543 (as described above). Moreover, the coupler 2518 can be disposed about the extensions 2383 and 2396 of the first coupling member 2380 and the second coupling member 2390, respectively, such that an orientation of the coupler 2518 is substantially maintained. Therefore, the rotation of the cartridge assembly 2500 can rotate the protrusions 2532 and 2543 of the first push rod 2530 and the adapter 2542 within the opening 2519 defined by the coupler 2518 and as a result, the coupler 2518 no longer retains the first push rod 2530 in a substantially fixed axial position relative to the adapter 2542, and vice versa (see e.g., FIG. 39). Thus, the first push rod 2530 and the second push rod 2540 of the cartridge assembly 2500 are coupled to the first coupling member 2380 and the second coupling member 2390, respectively, of the drive mechanism 2300.

With cartridge assembly 2500 coupled to the lock mechanism 2200 and the drive mechanism 2300, the user, for example, can insert a portion of the cartridge assembly 2500 of the reposable device 2000 through an incision and/or orifice of the body of a patient. Once inserted into the body, the user can manipulate the reposable device 2000 such that, for example, the distal end portions 2573 and 2583 of the first clamp member 2570 and the second clamp member 2580, respectively, are disposed about a target tissue (e.g., a target vascular tissue to be ligated and/or occluded). With the cartridge assembly 2500 disposed in the desired location in the body, the user, for example, can apply a pressure to the grip portion 2120 of the housing 2110 and the trigger 2420 of the actuator 2400 to rotate the engagement portion 2410 and the cam portion 2425 of the actuator 2400 about the axis defined by the axle 2421 (as described above). In this manner, the actuator 2400 can be rotated relative to the housing 2100 to transition the reposable device 2000 from the second configuration to a third configuration, as indicated by the arrow EE in FIG. 40. Expanding further, with the axle 2421 disposed in a substantially fixed angular position relative to the second arm 2415 of the engagement portion 2410 and the first cam 2430 and the second cam 2435 of the cam portion 2425 (as described above), the pivoting motion of the engagement portion 2410 can concurrently rotate the axle 2421 about its axis, which in turn, can concurrently pivot the cam portion 2425 about the axis defined by the axle 2421. More particularly, as shown in FIG. 40, the second cam 2435 is pivoted about the axis defined by the axle 2421.

As described above, the rack portion 2437 of the second cam 2435 can selectively engage the ratchet portion 2447 such that, as the cam portion 2425 is rotated about the axis defined by the axle 2421, the rack portion 2437 rotates the cam follower 2446 about the axle 2451 from a first angular direction, thereby rotating the return portion 2448 away from the post 2450 and placing the spring 2449, for example, in tension. Thus, the spring 2449 can exert a reaction force in response to the rotation of the cam follower 2446 that is sufficient to maintain the ratchet portion 2447 in contact with the rack portion 2437. Moreover, the pivoting motion of actuator 2400 can, for example, transition the spring 2427 from a first configuration of lower potential energy to a second configuration of greater potential energy (i.e., the spring 2427 exerts a reaction force in response to the rotation of the actuator 2400). For example, as described above, the spring 2427 can be a torsion spring or the like with a first end portion in contact with the post 2428 and a second end portion in contact with an inner surface of the housing 2110. As such, the rotation of the cam portion 2425 places the spring 2427 in compression (e.g., a configuration of greater potential energy). Therefore, with the ratchet portion 2447 in contact with the rack portion 2437, the cam follower 2446 can substantially limit a rotational motion of the cam portion 2425 in a substantially opposite direction (e.g., in response to a force exerted by the spring 2427, as described above) that is sufficient to maintain the actuator 2400 in a substantially fixed angular position if, for example, the user no longer applies pressure to the grip portion 2120 of the housing 2110 and the trigger 2420.

Figure 40:
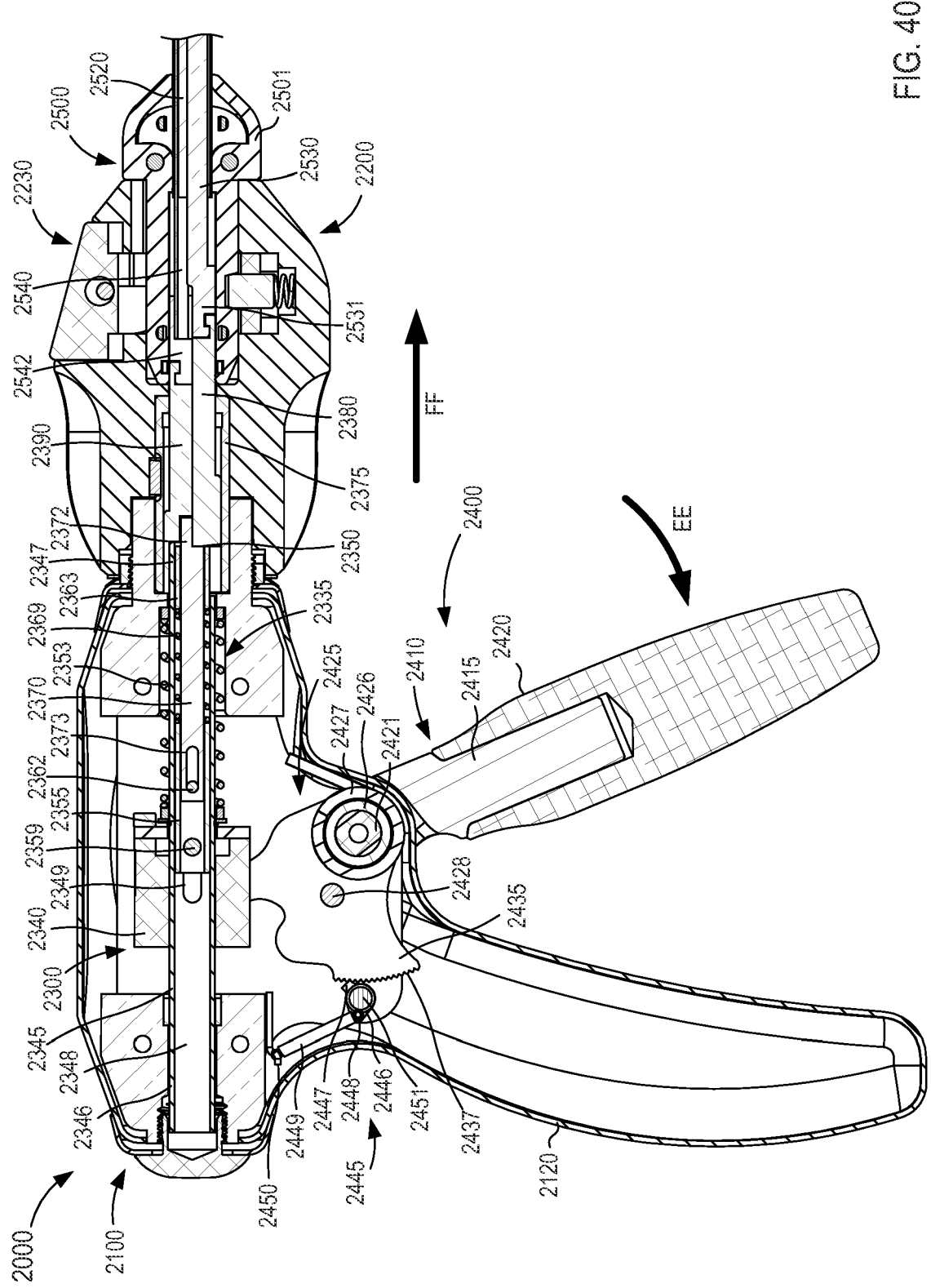
FIG. 40 is a cross-sectional view of the portion of the reposable device taken along the line $X_4$-$X_4$ in FIG. 36, in a third configuration.

With the actuation portion 2436 of the second cam 2435 movably disposed in the corresponding channel 2341 defined by the shuttle 2340 of the drive mechanism 2300 (not shown in FIGS. 31-46) to form the kinematic link (as described above), the pivoting motion of the second cam 2435 exerts a force that is applied to the shuttle 2340 and/or that is otherwise converted by the kinematic link to move the shuttle 2340 in a translational (e.g., axial) motion of the shuttle 2340 in the distal direction, as indicated by the arrow FF in FIG. 40. The motion of the shuttle 2340 in the distal direction results in a similar and/or concurrent movement of at least a part of the movable portion 2335 of the drive mechanism 2300, thereby transitioning the drive mechanism 2300 from a first configuration (i.e., prior to being moved as shown, for example, in FIG. 37) to a second configuration. For example, the distal movement of the shuttle 2340 also moves the first pin 2359 in the distal direction through the slot 2349 defined by the first actuating tube 2345 from a first position (e.g., a proximal position) to a second position (e.g., a distal position) relative to the slot 2349. More particularly, the first pin 2359 can be moved in the slot 2349 to the second position, in which the first pin 2359 is placed in contact with an inner surface (i.e., a distal boundary) defining a portion of the slot 2349. Therefore, with the first pin 2359 maintained in the substantially fixed axial position relative to the second actuating tube 2355 (as described above), the distal movement of the shuttle 2340 results in a similar and/or concurrent movement of the second actuating tube 2355 relative to the first actuating tube 2345. Similarly, with the second pin 2362 maintained in a substantially fixed axial position relative to the second actuating tube 2355, movement of the second actuating tube 2355 in the distal direction results in a similar and/or concurrent movement of the second pin 2362.

As the second actuating tube 2355 is moved in the distal direction, the second actuating tube 2355 exerts a force on the second bias member 2369, which in turn, exerts at least a portion of the force on the push sleeve 2363 to move the push sleeve 2363 in the distal direction. In other words, the portion of the force exerted by the second bias member 2369 is sufficient to overcome a reaction force exerted by the push sleeve 2363, thus the push sleeve 2363 is similarly and/or concurrently moved in the distal direction. In a similar manner, the arrangement of the push rod 2370 and the second actuating tube 2355 can be such that the friction force defined therebetween (as described above) is sufficient to retain the push rod 2370 in a substantially fixed position relative to the second actuating tube 2355 and as such, the push rod 2370 can be moved in the distal direction in a substantially similar and/or concurrent manner as the second actuating tube 2355. As a result of the distal movement of the shuttle 2340, the first actuating tube 2345, the second actuating tube 2355, the push sleeve 2363, and the push rod 2370, the first coupling member 2380 can be moved within the distal sleeve 2375, as indicated by the arrow FF in FIG. 40. Moreover, the first coupling member 2380 can be configured to move in the distal direction relative to the second coupling member 2390. Thus, with the first push rod 2530 of the cartridge assembly 2500 coupled to the first coupling member 2380 of the drive mechanism 2300, the distal movement of the movable portion 2335 moves the first push rod 2530 in the distal direction.

Figure 41:
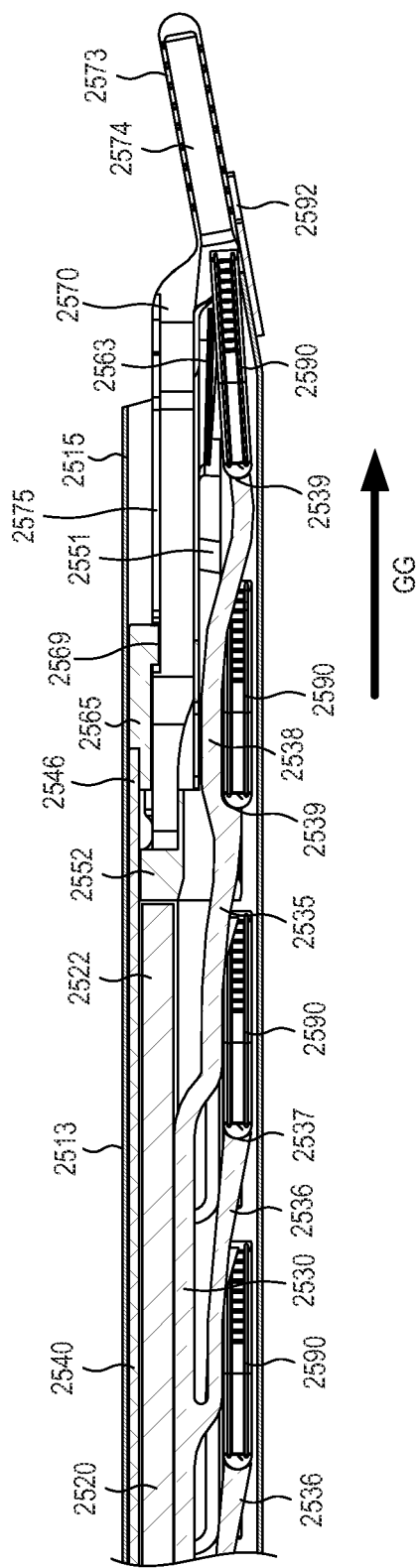
FIG. 41 is a cross-sectional view of a distal end portion of the cartridge assembly taken along the line $X_4$-$X_4$ in FIG. 36, in a second configuration.

In some instances, the distal movement of the first push rod 2530 can, for example, place the engagement surface 2537 of each push arm 2536 in contact with a different surgical clip 2590 retained by a corresponding clip retainer 2524 of the spine 2520, as indicated by the arrow GG in FIG. 41. Similarly, each engagement surface 2529 of the extension 2528 can be placed in contact with a different surgical clip 2590 and as such, cartridge assembly 2500 can be transitioned from a first configuration to a second configuration. In some instances, the distal movement of the first push rod 2530 can be sufficient to collectively move the surgical clips 2590 relative to the clip retainers 2524 and/or the clamp mechanism 2550. In other instances, the engagement surface 2537 of each push arm 2536 can be spaced apart from a corresponding surgical clip 2590 prior to the rotation of the actuator 2400 and as such, the distal movement of the first push rod 2530 places the engagement surfaces 2537 and 2539 in contact with a corresponding surgical clip 2590 substantially without moving the surgical clip 2590.

In some instances, the user can continue to exert a pressure on the grip portion 2120 and the trigger 2420 to rotate the engagement portion 2410 and the cam portion 2425 about the axis defined by the axle 2421 (as described above). Thus, the actuator 2400 can be rotated relative to the housing 2100 to transition the reposable device 2000 from the third configuration to a fourth configuration, as indicated by the arrow HH in FIG. 42. In this manner, the second cam 2435 can be further rotated about the axis defined by the axle 2421 to move the shuttle 2430 relative to the housing 2100, as described above. The rotation of the second cam 2435 also advances the cam follower 2446 along the surface of the rack portion 2437 and increases the potential energy of the spring 2427 included in the cam portion 2425 (e.g., further compresses the spring 2427, as described above).

Figure 42:
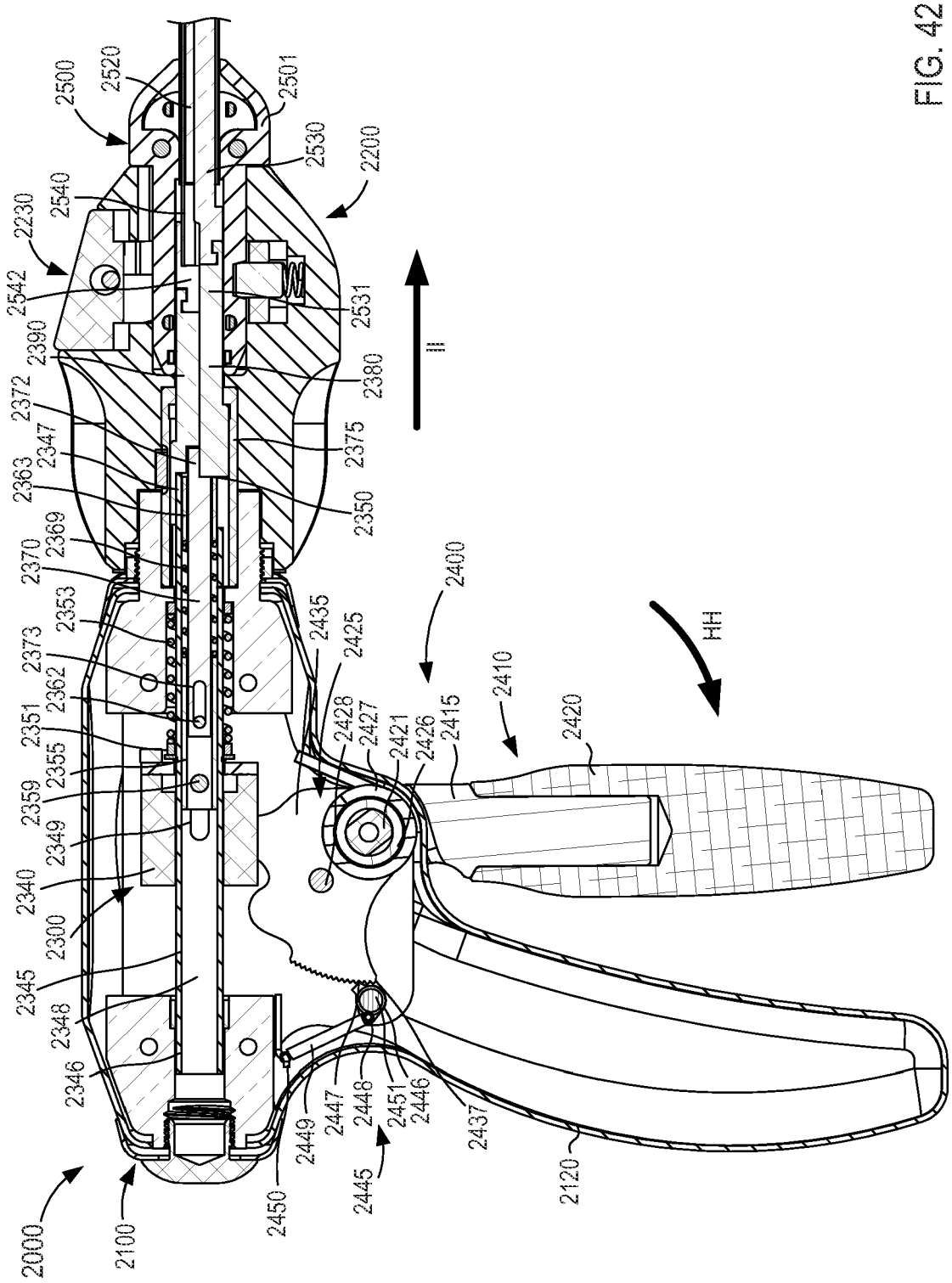
FIG. 42 is a cross-sectional view of the portion of the reposable device taken along the line $X_4$-$X_4$ in FIG. 36, in a fourth configuration.

The rotation of the second cam 2435 can move the shuttle 2430 in the distal direction, which results in a similar and/or concurrent movement of at least a part of the movable portion 2335 of the drive mechanism 2300, as indicated by the arrow II in FIG. 42. Thus, the drive mechanism 2300 can be transitioned from its second configuration to a third configuration. For example, as described above, the distal movement of the shuttle 2340 also moves the first pin 2359 in the distal direction, however, with the first pin 2359 in the second position relative to the slot 2349 defined by the first actuating tube 2345 (e.g., in contact with a distal boundary defining a portion of the slot 2349), the distal movement of the first pin 2359 also moves the first actuating tube 2345 in the distal direction. As shown in FIG. 42, with the first bias member 2353 disposed between the proximal stop 2351 of the first actuating tube 2345 and the distal support member 2230 (as described above), the distal movement of the first actuating tube 2345 can transition the first bias member 2353 from a first configuration (e.g., having a lower potential energy) towards a second configuration (e.g., having a greater potential energy). Thus, the shuttle 2430 can be moved in the II direction with sufficient force to overcome a reaction force exerted by the first bias member 2353 (e.g., a reaction force in response to the first bias member 2353 being, for example, compressed). The distal movement of the shuttle 2430 also results in a similar and/or concurrent movement of the second actuating tube 2355, the second pin 2362, the second bias member 2369, the push sleeve 2363, and the push rod 2370, as described above.

With the distal end portion 2347 of the first actuating tube 2345 in contact with the first shoulder 2394 formed and/or defined by the second coupling member 2390 (as described above), the distal movement of the first actuating tube 2345 results in a distal movement of the second coupling member 2390 relative to the distal sleeve 2375. Similarly, with the first coupling member 2380 in contact with the push rod 2370 and the push sleeve 2350, the distal movement of the push rod 2370 and the push sleeve 2363 further moves the first coupling member 2380 in the distal direction relative to the distal sleeve 2375. In this manner, the first coupling member 2380 and the second coupling member 2390 can be moved with a substantially similar velocity and in a substantially concurrent motion. Moreover, as shown in FIG. 42, the first coupling member 2380 can be moved relative to the distal sleeve 2375 to place the shoulder 2385 in contact with the inner surface of the distal sleeve 2375 that defines a portion of the lumen 2378 (as described above). Thus, the shoulder 2385 and the distal sleeve 2375 can substantially limit a further distal movement of the first coupling member 2380.

Figure 43:
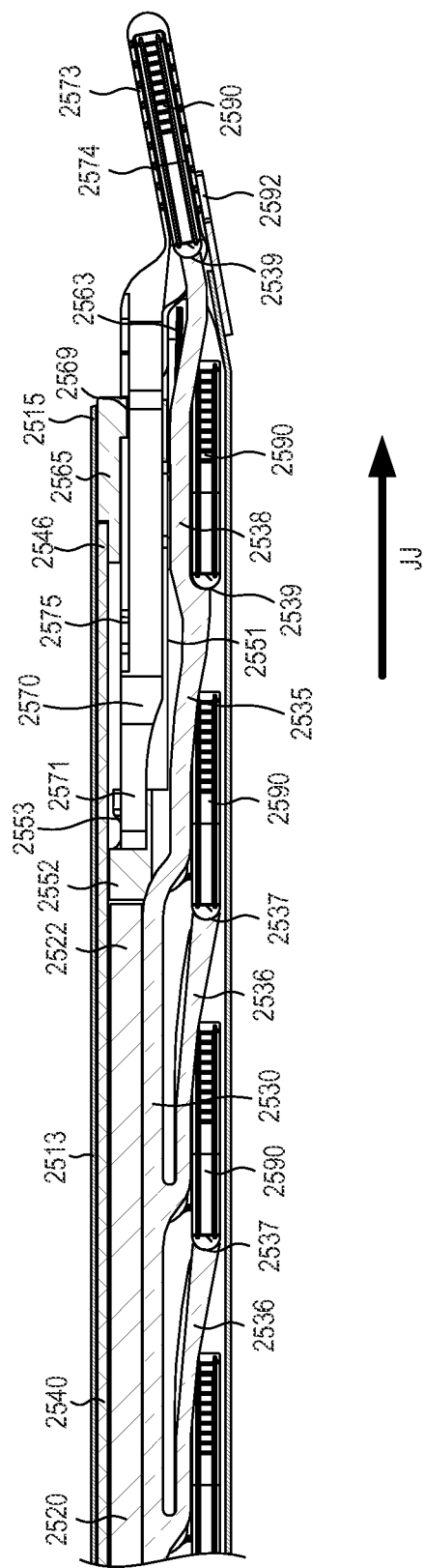
FIG. 43 is a cross-sectional view of the distal end portion of the cartridge assembly taken along the line $X_4$-$X_4$ in FIG. 36, in a third configuration.

With the first push rod 2530 of the cartridge assembly 2500 coupled to the first coupling member 2380 of the drive mechanism 2300, the distal movement of the movable portion 2335 moves the first push rod 2530 in the distal direction, as described above. Similarly, with the second push rod 2540 of the cartridge assembly 2500 coupled to the second coupling member 2390 of the drive mechanism 2300 (as described above), the distal movement of the movable portion 2335 also moves the second push rod 2540 in the distal direction to transition the cartridge assembly 2500 from its second configuration to a third configuration, as shown in FIG. 43. Thus, with the engagement surface 2537 of each push arm 2536 in contact with a different surgical clip 2590 retained by a corresponding clip retainer 2524 of the spine 2520 (as described above), the distal movement of the first push rod 2530 collectively moves the surgical clips 2590 relative to the spine 2520, as indicated by the arrow JJ in FIG. 43. More specifically, the first push rod 2530 can collectively move each surgical clip 2590 in the distal direction relative to the spine 2520 such that each surgical clip 2590 is removed from its corresponding clip retainer 2524 and placed in contact with, and temporarily retained by, the distally adjacent clip retainer 2524. In addition, the distal most surgical clip 2590 and the surgical clip 2590 adjacent thereto can be advanced in the distal direction relative to the clamp mechanism 2550. That is to say, the extension 2538 of the first push rod 2530 can advance the distal most surgical clip 2590 and the surgical clip 2590 adjacent thereto in the distal direction beyond the set of clip retainers 2524 included in the spine 2520 to be disposed in and/or retained by the clamp mechanism 2550. As shown, in FIG. 43, the extension 2538 of the first push rod 2530 can advance the distal most surgical clip 2590 such that the distal most surgical clip 2590 is disposed in the space defined between the recess 2574 defined by the first clamp member 2570 (described above) and the recess 2584 defined by the second clamp member 2580 (described above). Moreover, the arrangement of the bifurcated portion 2556 of the shoe 2551 can substantially guide and/or direct each surgical clip 2590 as that surgical clip 2590 is advanced in the distal direction within the space defined between the first arm 2557 and the second arm 2561.

With the distal end portion 2546 of the second push rod 2540 in contact with the cinch member 2565, the distal movement of the second push rod 2540 results in a distal movement of the cinch member 2565 relative to the first clamp member 2570 and the second clamp member 2580 (not shown in FIG. 43). More specifically, as described above, the first clamp member 2570 and the second clamp member 2580 are disposed in the notch 2568 defined by the cinch member 2565 and the protrusion 2569 of the cinch member 2565 is disposed in the tracks 2575 and 2585 of the first clamp member 2570 and the second clamp member 2580, respectively. Thus, the cinch member 2565 can move along a length of the first clamp member 2570 and a corresponding length of the second clamp member 2580 from a proximal position (see e.g., FIG. 41) towards a distal position, as shown in FIG. 43. The arrangement of the first clamp member 2570 and the second clamp member 2580 can be such that a space defined therebetween at the proximal end portions 2571 and 2581, respectively, is less than a space defined therebetween at the distal end portions 2573 and 2583, respectively. Therefore, as the cinch member 2565 is moved in the distal direction relative to the clamp members 2570 and 2580, a surface defining the notch 2368 of the cinch member 2565 can be placed in contact with an outer surface (e.g., a side, a wall, an edge, etc.) of each clamp member 2570 and 2580 and as a result, the first clamp member 2570 and the second clamp member 2580 can be urged to pivot in the recess 2553 defined by the shoe 2551 (described above) about the axis defined by the protrusions 2572 and 2582, respectively. In this manner, as the distal most surgical clip 2590 is advanced into the space defined between the recess 2574 of the first clamp member 2570 and the recess 2584 of the second clamp member 2580, the cinch member 2565 can decrease the space therebetween such the recesses 2574 and 2584 are brought into contact with opposite sides of the surgical clip 2590, thereby retaining the surgical clip 2590 in a relatively fixed position.

In some instances, the user can continue to exert a pressure on the grip portion 2120 and the trigger 2420 to rotate the engagement portion 2410 and the cam portion 2425 about the axis defined by the axle 2421 (as described above). Thus, the actuator 2400 can be further rotated relative to the housing 2100 to transition the reposable device 2000 from the fourth configuration to a fifth configuration, as indicated by the arrow KK in FIG. 44. In this manner, the second cam 2435 can be further rotated about the axis defined by the axle 2421 to move the shuttle 2430 relative to the housing 2100, as described above. The rotation of the second cam 2435 is such that the rack portion 2437 of the second cam 2435 is rotated to a position that disengages the rack portion 2437 from the cam follower 2446. In this manner, the spring 2448 of the return portion 2445 can exert a force on the return portion 2448 of the cam follower 2446 that rotates the cam follower 2446 about the axle 2451 such that the distance defined between the return portion 2448 of the cam follower 2446 and the post 2450 is reduced (e.g., back to a first angular position and/or the like). In addition, the rotation of the second cam 2435 also increases the potential energy of the spring 2427 included in the cam portion 2425 (e.g., further compresses the spring 2427, as described above).

Figure 44:
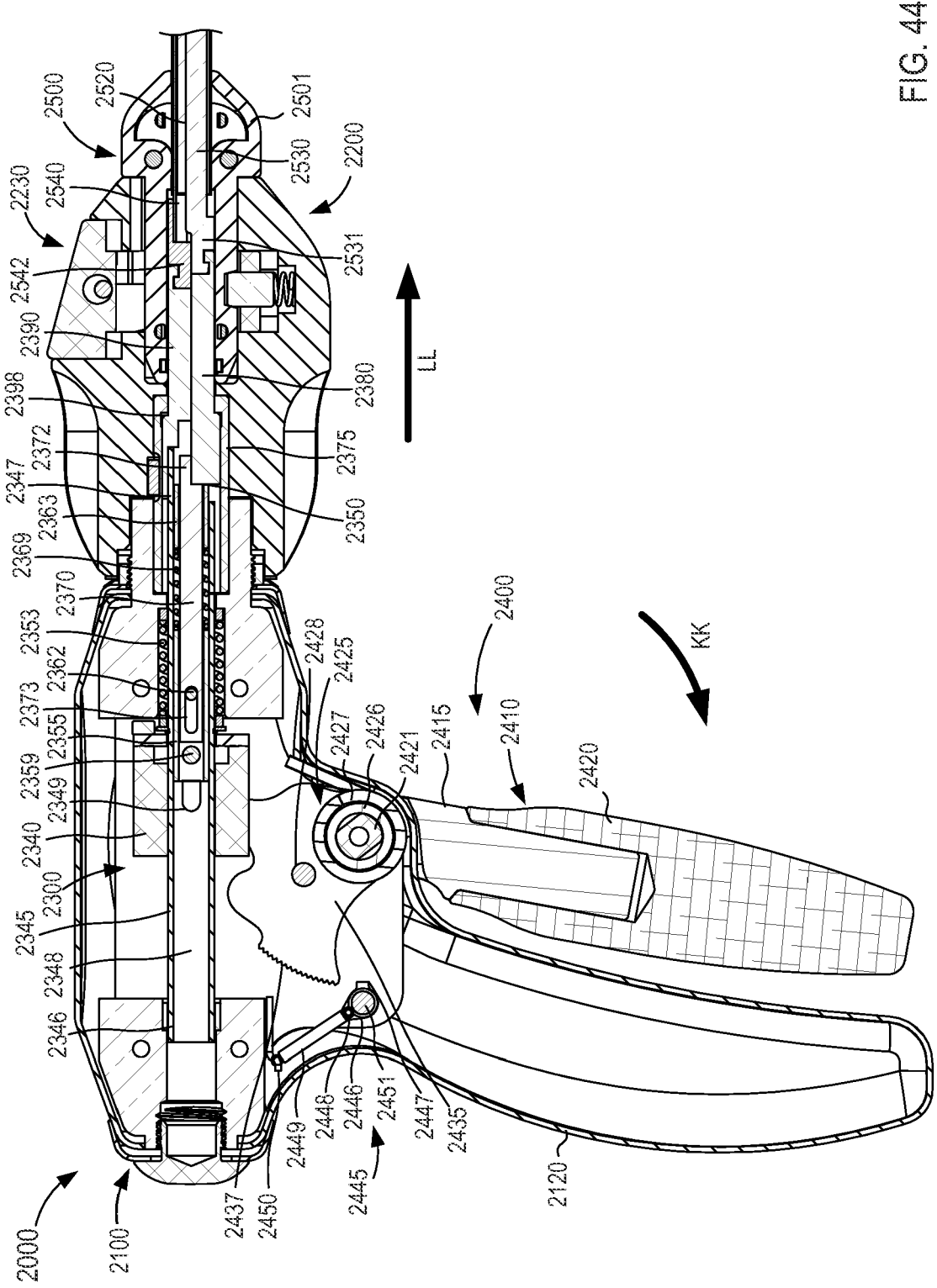
FIG. 44 is a cross-sectional view of the portion of the reposable device taken along the line $X_4$-$X_4$ in FIG. 36, in a fifth configuration.

The rotation of the second cam 2435 also moves the movable portion 2335 of the drive mechanism 2300 in a similar manner as described above to transition the drive mechanism 2300 from its third configuration to a fourth configuration, as indicated by the arrow LL in FIG. 44. For example, as described above, the distal movement of the shuttle 2340 also moves the first pin 2359 and the first actuating tube 2345 in the distal direction, which in turn, can place the first bias member 2353 in its second configuration (as described above) associated with the greater potential energy. Thus, the shuttle 2430 can be moved in the LL direction with sufficient force to overcome a reaction force exerted by the first bias member 2353 (e.g., a reaction force in response to the first bias member 2353 being, for example, compressed). The distal movement of the shuttle 2430 also results in a similar and/or concurrent movement of the second actuating tube 2355 and the second pin 2362, however, with the shoulder 2385 of the first coupling member 2380 in contact with the inner surface of the distal sleeve 2375 (as described above), further distal movement of the push sleeve 2363 and the push rod 2370 is substantially limited and/or prevented. As such, the distal movement of the second actuating tube 2355, for example, can transition the second bias member 2369 disposed between the second actuating tube 2355 and the push sleeve 2363 from a first configuration having a lower potential energy to a second configuration having a greater potential energy (e.g., the second bias member 2369 can be a spring that is compressed to be placed in its second configuration). In other words, the second actuating tube 2355 can exert a force on a first end of the second bias member 2369 and the push sleeve 2363 can exert a reaction force on a second end of the second bias member 2369 that collectively are sufficient to overcome a force exerted by the second bias member 2369 that would otherwise resist the transition from its first configuration to its second configuration. In embodiments in which the second bias member 2369 is a spring or the like, the second configuration can be associated with, for example, a fully compressed and/or solid configuration. In addition, the distal movement of the second actuating tube 2355 also moves the second pin 2362 in the slot 2373 defined by the push rod 2370 from a first position (e.g., a proximal position) to a second position (e.g., a distal position) relative the push rod 2370. Thus, the shuttle 2340 can collectively move the first actuating tube 2345 and the second actuating tube 2355 in the distal direction relative to the push sleeve 2363 and the push rod 2370, as shown in FIG. 44.

With the distal end portion 2347 of the first actuating tube 2345 in contact with the first shoulder 2394 formed and/or defined by the second coupling member 2390 (as described above), the distal movement of the first actuating tube 2345 results in a distal movement of the second coupling member 2390 relative to the distal sleeve 2375. Moreover, the second coupling member 2390 can be moved to a position in which the second pin 2362 is placed in contact with a distal surface defining a portion of the slot 2373. In this manner, with the second bias member 2369 in the second configuration (e.g., a solid and/or fully compressed configuration) and with the second pin 2362 in contact with the distal surface defining the portion of the slot 2373, the first coupling member 2380, the push rod 2370, the push sleeve 2363, the second bias member 22369, and the second actuating tube 2355 can effectively form, for example, a substantially rigid rod that is substantially non-compressible in the axial direction. Thus, further distal movement of the shuttle 2340 can be substantially prevented which in turn, substantially prevents further distal movement of the second coupling member 2390 and further rotation of the actuator 2400 relative to the grip portion 2120 of the housing 2100.

Figure 45:
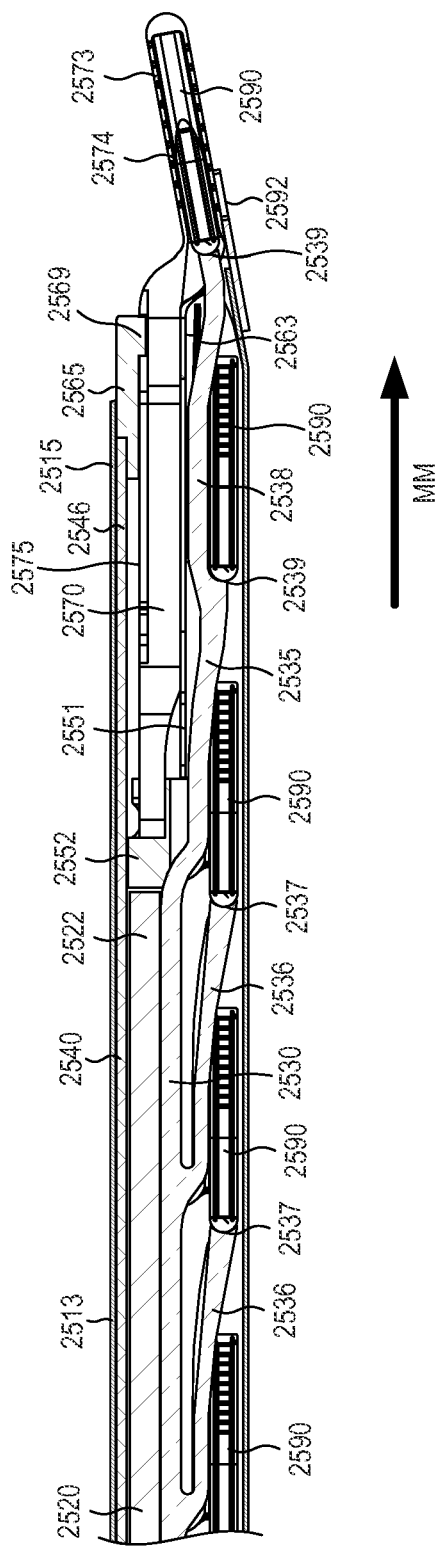
FIG. 45 is a cross-sectional view of the distal end portion of the cartridge assembly taken along the line $X_4$-$X_4$ in FIG. 36, in a fourth configuration.
Figure 46:
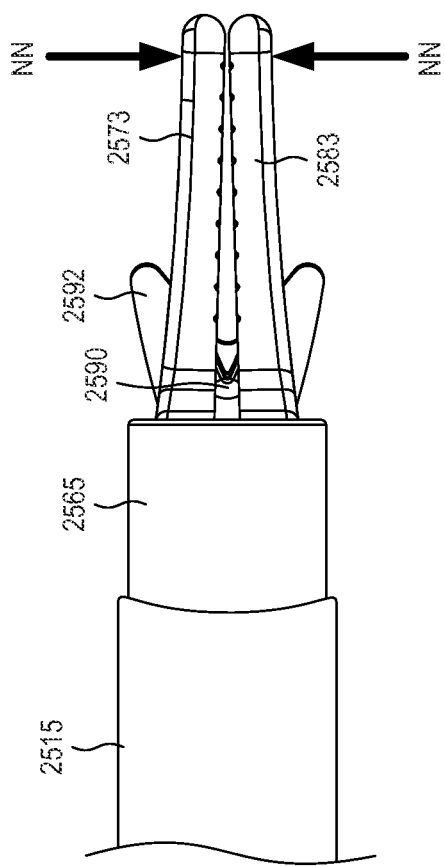
FIG. 46 is a top view of a distal end portion of the cartridge assembly of FIGS. 19 and 20 in the fourth configuration.
Figure 47:
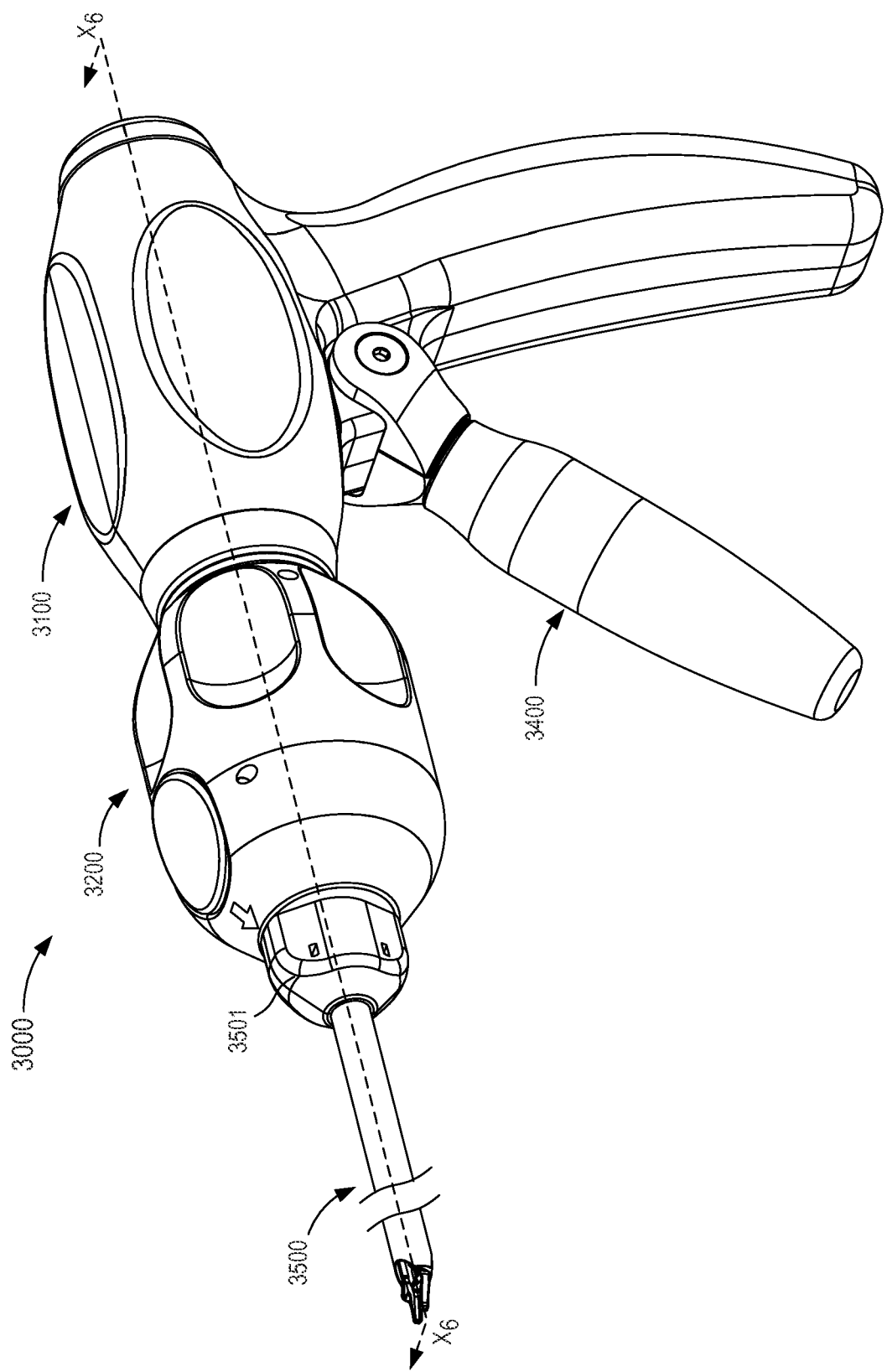
FIG. 47 is a perspective view of a reposable device according to an embodiment.

With the first push rod 2530 of the cartridge assembly 2500 maintained in a substantially fixed position (e.g., due to the first coupling member 2380 being placed in contact with the inner surface of the distal sleeve 2375), the second push rod 2540 of the cartridge assembly 2500 can be moved in the distal direction relative to the first push rod 2530 to transition the cartridge assembly 2500 from its third configuration to a fourth configuration. Thus, as indicated by the arrow MM in FIG. 45, the distal movement of the second push rod 2540 results in a distal movement of the cinch member 2565 relative to the first clamp member 2570 and the second clamp member 2580 (not shown). More specifically, the cinch member 2565 can move along a length of the first clamp member 2570 and a corresponding length of the second clamp member 2580 to be disposed in its distal position, as shown in FIG. 45. As the cinch member 2565 is moved in the distal direction relative to the clamp members 2570 and 2580, the first clamp member 2570 and the second clamp member 2580 are pivoted about the axis defined by the protrusions 2572 and 2582, respectively, such that the space defined between the distal end portions 2573 and 2583, respectively is reduced. Hence, with the recess 2574 of the first clamp member 2570 in contact with a first side of the surgical clip 2590 and the recess 2584 of the second clamp member 2580 in contact with a second, opposite side of the surgical clip 2590, the space between the distal end portions 2573 and 2583 of the clamp members 2570 and 2580, respectively can be reduced to an extent that the surgical clip 2590 is clamped, deformed, closed, bent, and/or otherwise reconfigured, as indicated by the opposing arrows NN in FIG. 46. Moreover, with the cartridge assembly 2500 positioned within the body such that the clamp members 2570 and 2580 are disposed about, for example, the target vascular tissue, the clamping and/or otherwise reconfiguring of the surgical clip 2590 can secure the surgical clip 2590 to the target vascular structure to ligate and/or occlude that target vascular structure.

Once the surgical clip 2590 is disposed about the desired vascular structure, in some instances, the user can, for example, reduce and/or remove the pressure exerted on the grip portion 2120 and the engagement portion 2420 of the handle 2100. As such, at least a portion of a force sufficient to maintain each of the spring 2427 included in the cam portion 2425 of the actuator 2400, and the first bias member 2353 and the second bias member 2369 of the drive mechanism 2300 in its second configuration is removed. Thus, spring 2427, the first bias member 2353, and the second bias member 2369 can collective exert a force (i.e., each converts its potential energy to kinetic energy) to transition the reposable device 2000 from its fifth configuration (e.g., FIGS. 44-46) to its second configuration (e.g., FIGS. 36-39). In some instances, the user can manipulate the reposable device 2000 to reposition the cartridge assembly 2500 in the body such that the distal end portion 2573 of the first clamp member 2570 and the distal end portion 2583 of the second clamp member 2580 is disposed about a different vascular structure (or the same vascular structure at a different location along that vascular structure). Thus, the user can manipulate the reposable device 2000 to ligate and/or occlude that vascular structure in the manner described above with reference to FIGS. 40-46. Once the target vascular structures have been ligated and/or occluded and/or after the surgical procedure (e.g., a laparoscopic procedure, an endoscopic procedure, and/or the like) is completed, the user can remove the cartridge assembly 2500 from the body and can manipulate the reposable device 2000 to decouple the cartridge assembly 2500 from the handle 2100. In some instances, the cartridge assembly 2500 can be safely discarded, while the handle 2100 can be reused.

As described above, the arrangement of the reposable device 2000 can be such that the universal handle 2100 can be used with cartridge assemblies having different configurations. For example, the cartridge assembly 2500 can be associated with and/or can include a set of 5 mm surgical clips. In some instances, the universal handle 2100 can be coupled to a cartridge assembly associated with and/or including a set of surgical clips having any suitable size such as, for example, 1 mm, 2 mm, 3 mm, 4 mm, 6 mm, 7 mm, 8 mm, 9 mm, 10 mm, 15 mm, and/or the like.

For example, FIGS. 47-60 illustrate reposable device 3000 according to an embodiment. The reposable device 3000 includes a cartridge assembly 3500 that can be removably coupled to a universal handle 3100 (see e.g., FIG. 50), for example, to apply one or more surgical clips to a target tissue in the body, as described in further detail herein. The universal handle 3100 (also referred to herein as "handle") can be substantially similar to and/or the same as the universal handle 2100 described in detail above with reference to FIGS. 2-44. Thus, aspects of the handle 3100 are not described in further detail herein. Rather, a high level description of salient mechanisms, assemblies, sub-assemblies, components, and/or the like of the universal handle 3100 is provided in the proceeding discussion to provide context as it relates to the form and/or function of the cartridge assembly 3500.

As shown in FIGS. 47, 53, 54, 56, and 58, the handle 3100 includes a housing 3110, a lock mechanism 3200, a drive mechanism 3300, and an actuator 3400. The housing 3110 is configured to enclose and/or house at least a portion of the drive mechanism 3300 and the actuator 3400, as described above with reference to the housing 2110 of the handle 2100. The lock mechanism 3200 is coupled to a portion of the drive mechanism 3300 and/or the housing 3110. The lock mechanism 3200 defines an opening configured to removably receive a portion of the cartridge assembly 3500, as described above with reference to the lock mechanism 2200 of the handle 2100. As shown, for example, in FIG. 53, the lock mechanism 3200 includes a lock actuator 3230 that has a lock member 3250 configured to selectively engage a portion of the cartridge assembly 3500 to temporarily retain the cartridge assembly 3500 in a substantially fixed position relative to the lock mechanism 3200. More specifically, as described above with reference to the lock actuator 2230, the lock actuator 3230 can be moved within a portion of the lock mechanism 3200 to selectively dispose the lock member 3250 in, for example, a recess (described below) defined by a portion of the cartridge assembly 3500.

Figure 53:
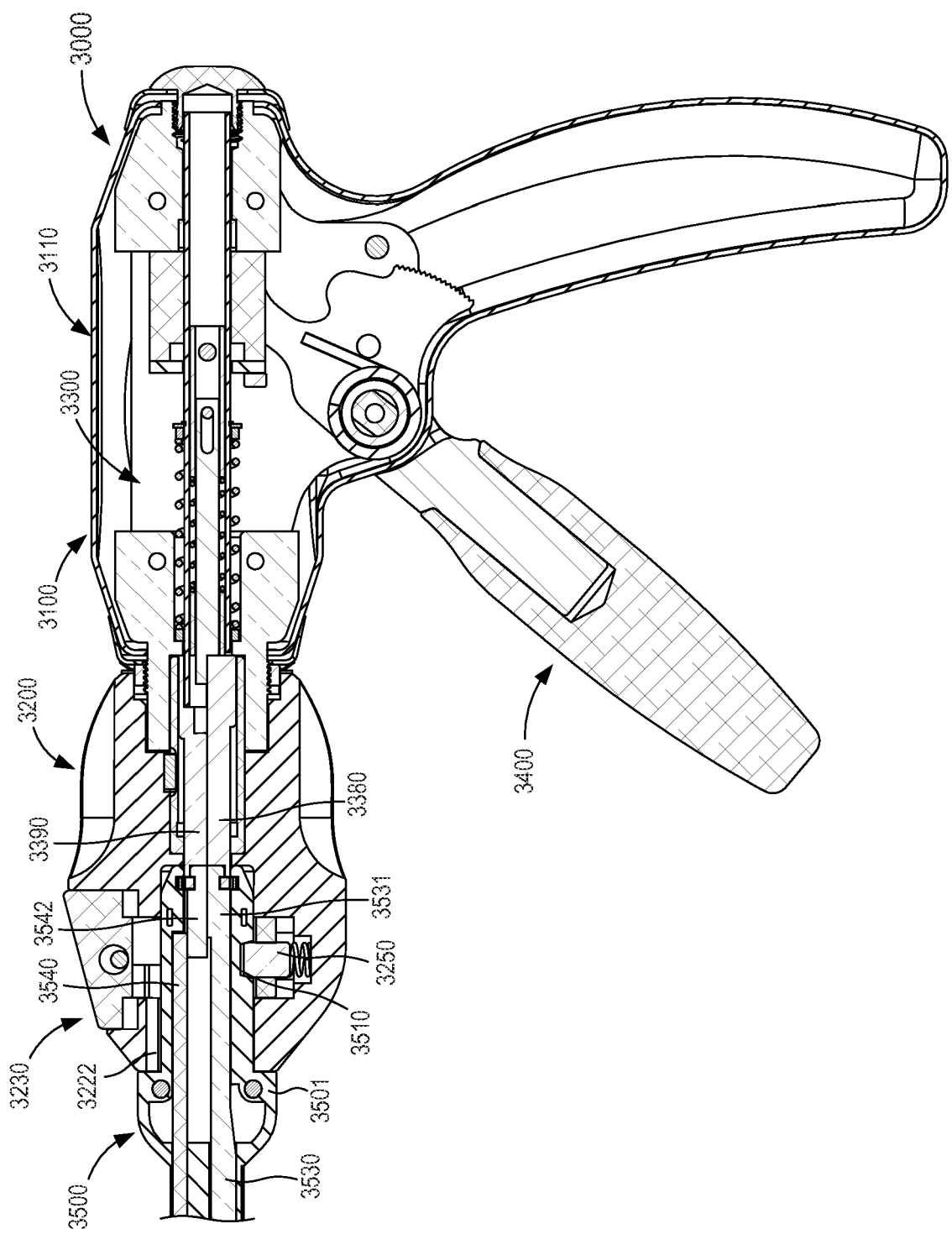
FIG. 53 is a cross-sectional view of the portion of the reposable device taken along the line $X_5$-$X_5$ in FIG. 47, in a second configuration.
Figure 54:
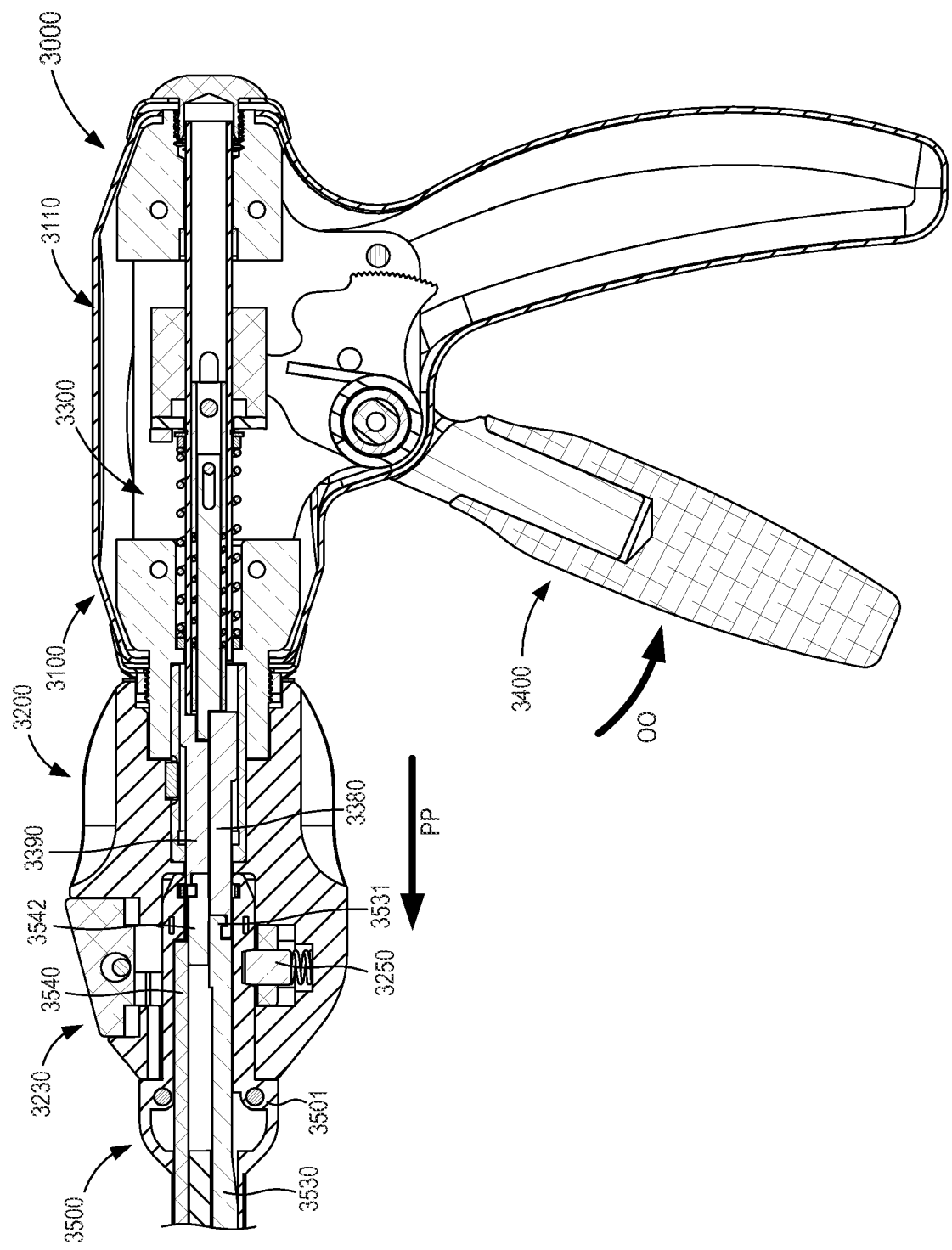
FIG. 54 is a cross-sectional view of the portion of the reposable device taken along the line $X_5$-$X_5$ in FIG. 47, in a third configuration.

At least a portion of the drive mechanisms 3300 is movably disposed within the housing 3110 and is configured to be removably coupled to a portion of the cartridge assembly 3500 such that movement of a portion of the drive mechanism 3300 moves a corresponding portion of the cartridge assembly 3500. For example, as shown in FIG. 53, the drive mechanism 3300 include a first coupling member 3380 and a second coupling member 3390 that can be coupled to a corresponding portion of the cartridge assembly 3500 such that movement of the first coupling member 3380 and/or the second coupling member 3390 results in a similar and/or concurrent motion of the corresponding portion of the cartridge assembly 3500, as described in further detail herein. The actuator 3400 of the handle 3100 is rotatably coupled to the housing 3110 and includes a portion that is movably disposed in the housing 3110 to be in contact with a portion of the drive mechanism 2300. For example, a portion of the actuator 3400 and a portion of the drive mechanism 3300 can form a kinematic link or the like such that a rotation of the actuator 3400 relative to the housing 3110 results in a linear (e.g., axial) motion of a portion of the drive mechanism 3300, as described above with reference to the actuator 2400 and the drive mechanism 2300 included in the handle 2100. Thus, the handle 3100 can function in a substantially similar manner as the handle 2100 described in detail above.

Figure 48:
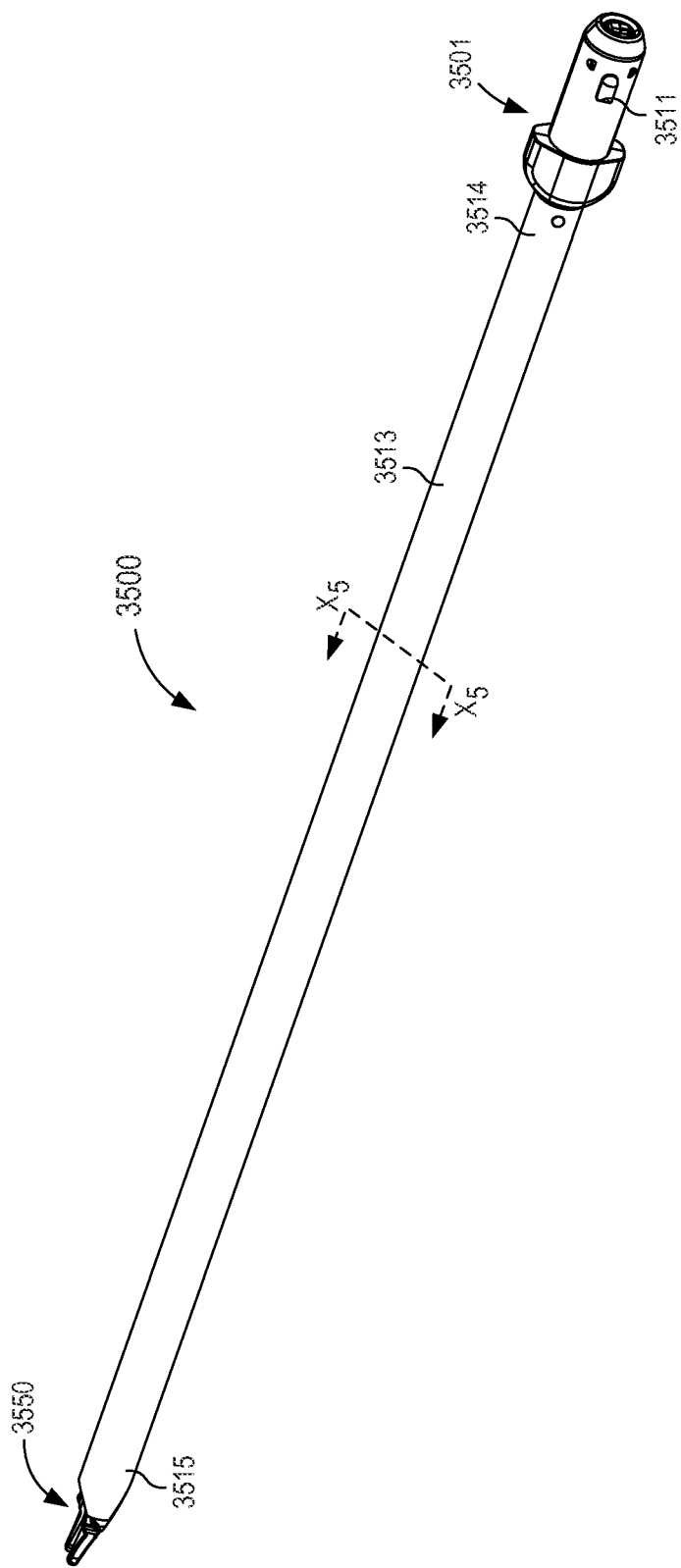
FIG. 48 is a perspective view of a cartridge assembly included in the reposable device of FIG. 47.
Figure 49:
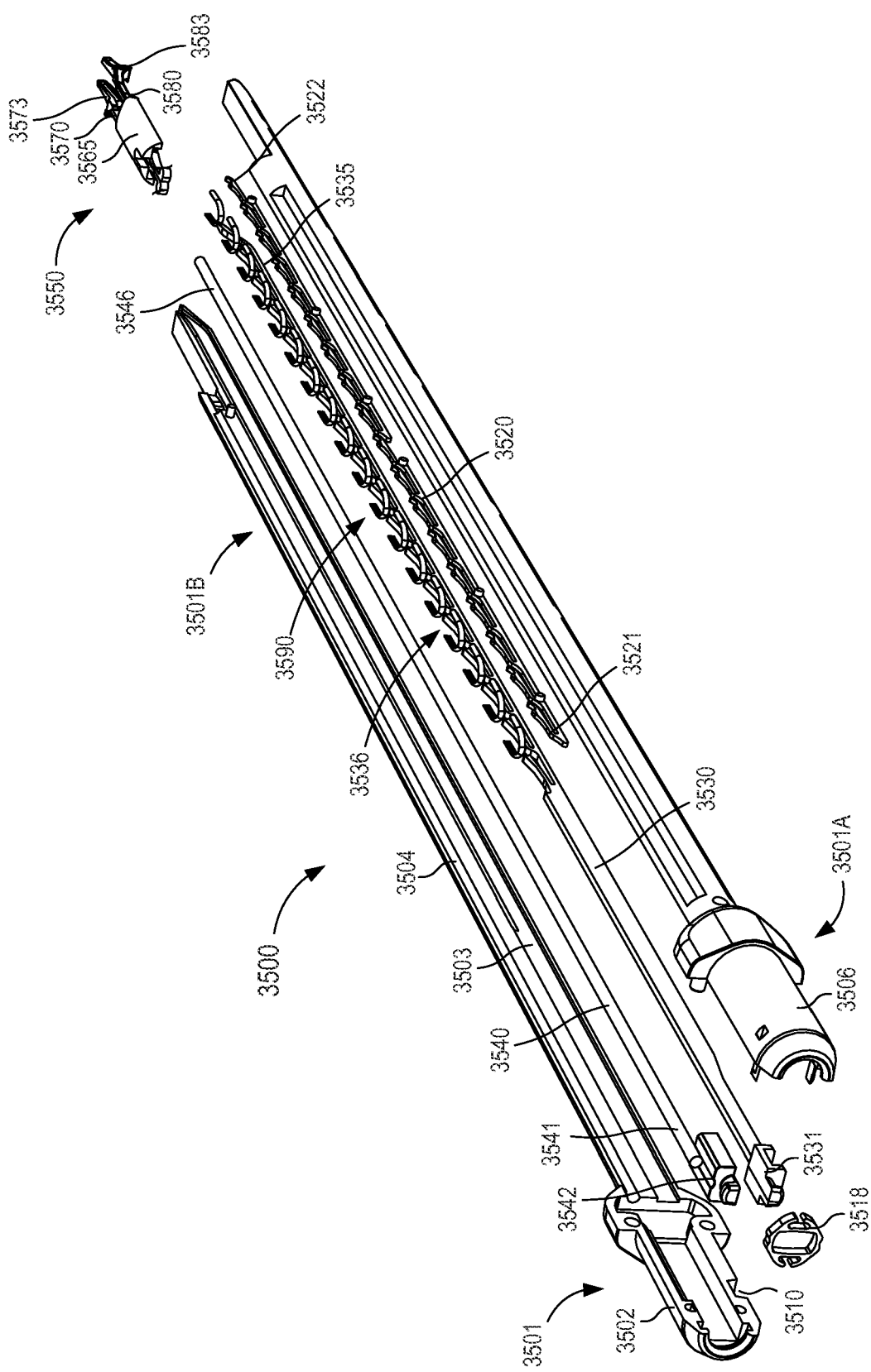
FIG. 49 is an exploded perspective view of a portion of the cartridge assembly of FIG. 48.

As shown FIGS. 48 and 49, the cartridge assembly 3500 of the reposable device 3000 includes an adapter 3501, an outer sheath 3513, a spine 3520, a first push rod 3530, a second push rod 3540, a coupler 3518, a clamp mechanism 3550, and a set of surgical clips 3590. The outer sheath 3513 has a proximal end portion 3514 and a distal end portion 3515 and defines a lumen 3516 (see e.g., FIG. 50) therethrough. The outer sheath 3513 is configured to substantially enclose and/or circumscribe a portion of the adapter 3501, the spine 3520, the first push rod 3530, the second push rod 3540, and the clamp mechanism 3550. More specifically, a portion of the first push rod 3530, a portion of the second push rod 3540, and a portion of the clamp mechanism 3550 can be movably disposed in the lumen 3516 defined by the outer sheath 3513, while the portion of the adapter 3501 and the spine 3520 are fixedly disposed in the lumen 3516. Thus, the first push rod 3530, the second push rod 3540, and the clamp mechanism 3550 can be moved in an axial direction in the lumen 3516 relative to the adapter 3501 and the spine 3520, as described in further detail herein.

Figure 50:
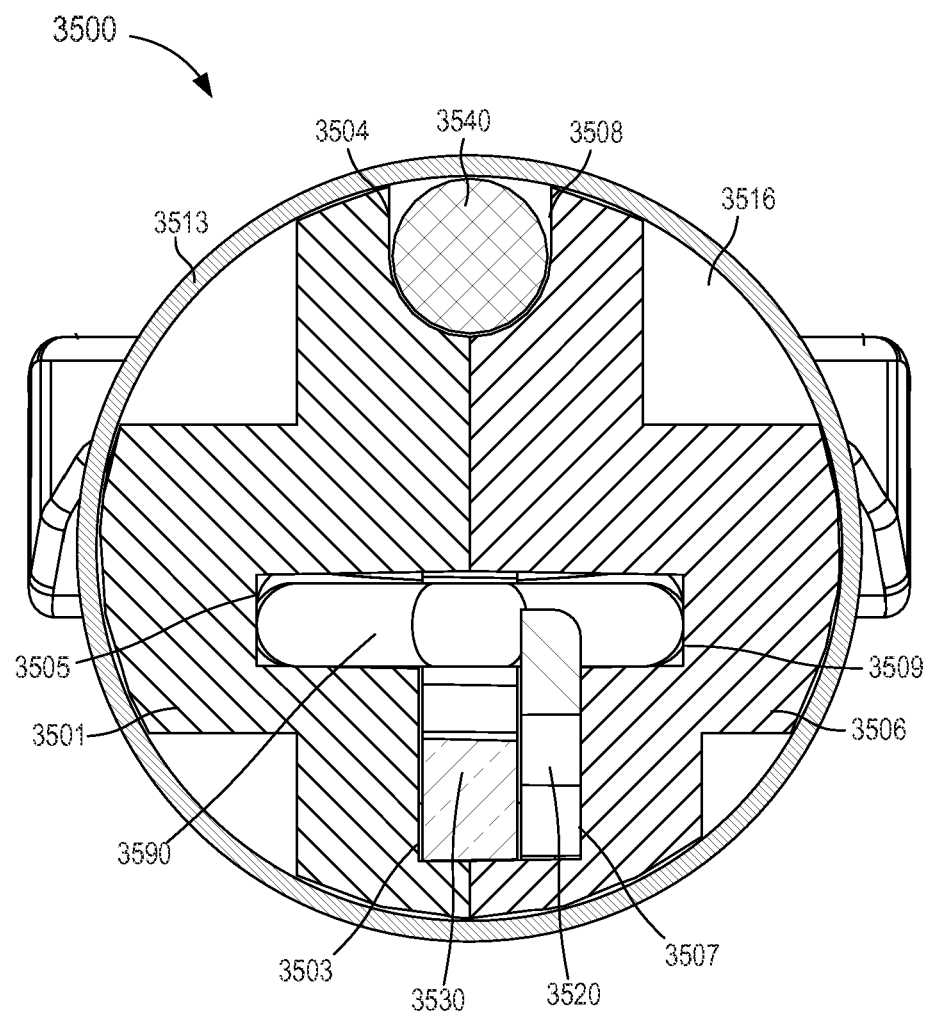
FIG. 50 is a cross-sectional view of the cartridge assembly taken along the line $X_6$-$X_6$ in FIG. 48.

As shown in FIGS. 49-50, the adapter 3501 includes a first member 3502 and a second member 3506 that can be coupled together to collectively form the adapter 3501. The adapter 3501, when the first member 3502 and the second member 3506 are coupled together, has a first portion 3501A and a second portion 3501B. The first portion 3501A of the adapter 3501 is configured to be coupled to the universal handle 3100, as described in further detail herein. The second portion 3501B is configured to be fixedly disposed in the lumen 3516 defined by the outer sheath 3513. The arrangement of the first member 3502 and the second member 3506 is such that, when coupled together, the adapter 3501 is substantially open at an end surface of the first portion 3501A and at an end surface of the second portion 3501B. Moreover, when the first member 3502 and the second member 3506 are coupled together, the adapter 3501 is configured to substantially enclose the spine 3520, the first push rod 3530, and the second push rod 3540. For example, as shown in FIG. 50, the first member 3502 of the adapter 3501 includes a surface that defines a first groove 3503, a second groove 3504, and a third groove 3505. The first groove 3503 defined by the first member 3502 of the adapter 3501 is configured to slidably receive a portion of the first push rod 3530. The second groove 3504 defined by the first member 3502 is configured to slidably receive a portion of the second push rod 3540. The third groove 3505 defined by the first member 3502 is configured to slidably receive a portion of each surgical clip 3590. Similarly, the second member 3506 of the adapter 3501 includes a corresponding surface that defines a first groove 3507, a second groove 3508, and a third groove 3509. The first groove 3507 defined by the second member 3506 of the adapter 3501 is configured to slidably receive a portion of the first push rod 3530. Furthermore, the spine 3520 is configured to be fixedly coupled to the second member 3506 at and/or along the first groove 3507 of the second member 3506. The second groove 3508 defined by the second member 3506 is configured to slidably receive a portion of the second push rod 3540. The third groove 3509 defined by the second member 3506 is configured to slidably receive a portion of each surgical clip 3590. The arrangement of the first push rod 2530 and the second push rod 2540 within the grooves 3503 and 3507 and the grooves 3504 and 3508, respectively, can be such that a proximal end portion 3531 of the first push rod 3530 and a proximal end portion 3541 of the second push rod 3540 extend into the first portion 3501A of the adapter 3501, as described in further detail herein. In this manner, the first member 3502 and the second member 3506 collectively define a set of paths along which the first push rod 3530, the second push rod 3540, and the set of surgical clips 3590 can moved, as described in further detail herein.

As described above, the first portion 3501A of the adapter 3501 is configured to be coupled to the universal handle 3100. The first portion 3501A of the adapter 3501 can be substantially similar to the adapter 2501 described above with reference to FIGS. 19-44. For example, as shown in FIGS. 48, 49, and 53, the first portion of the 3501A includes a protrusion 3511 and defines the recess 3510. More specifically, the first member 3502 of the adapter 3501 includes the protrusion 3511, while the first member 3502 and the second member 3506 collectively define the recess 3510. In this manner, the protrusion 3511 and the recess 3510 can be configured to substantially correspond with a notch 3222 defined by the lock mechanism 3200. Thus, the protrusion 3511 can be, for example, a clocking and/or reference feature configured to substantially align the cartridge assembly 3500 with the lock mechanism 3200 as the cartridge assembly 3500 is inserted therein, as describe above with reference to the cartridge assembly 2500. The recess 3510, collectively defined by the first member 3502 and the second member 3506, is configured to selectively receive a portion of the lock member 3250 included in the lock actuator 3230 to temporarily maintain the cartridge assembly 3500 in a relatively fixed position relative to the handle 3100, as described above.

As described above, the spine 3520 of the cartridge assembly 3500 is fixedly coupled to the second member 3506 of the adapter 3501. More specifically, the spine 3520 is fixedly coupled to a surface of the second member 3506 that defines a portion of the first groove 3507, as shown, for example, in FIG. 51. The spine 3520 can be any suitable shape, size, and/or configuration. For example, the spine 3520 has a proximal end portion 3521 and a distal end portion 3525, and includes a set of clip retainers 3524 that are linearly arranged along a length of the spine 3520 with each clip retainer 3524 being disposed at a substantially uniform spacing from an adjacent clip retainer 3524. More specifically, as shown in FIG. 51, the set of clip retainers 3524 extends from the proximal end portion 3521 to the distal end portion 3522 of the spine 3520 such that the distal most clip retainer 3524 is disposed substantially at the distal end of the spine 3520. Each clip retainer 3524 can selectively receive a surgical clip 3590 to temporarily couple each surgical clip 3590 to a different clip retainer 3524. In some embodiments, the spine 3520 can include, for example, nineteen clip retainers 3524, thereby retaining nineteen surgical clips 3590. Although not shown, in some embodiments, the cartridge assembly 3500 can be configured to retain one surgical clip 3590 in a distal position relative to the spine 3520. Thus, prior to use, the cartridge assembly 3500 can be configured to include and/or retain twenty surgical clips 3590. In other embodiments, the cartridge assembly 3500 can be configured to retain more than twenty surgical clips 3590 or less than twenty surgical clips 3590. Moreover, in some embodiments, the surgical clips 3590 can be, for example, 10 mm surgical clips.

As described above, the first push rod 3530 of the cartridge assembly 3500 is disposed in the adapter 3501 and can be moved in an axial direction between a first position (e.g., a proximal position) and a second position (e.g., a distal position). As shown in FIGS. 49 and 52, the first push rod 3530 has a proximal end portion 3531 and a distal end portion 3535. The proximal end portion 3531 is movably disposed in the first portion 3501A of the adapter 3501 and is configured to be selectively coupled to the first coupling member 3380 of the drive mechanism 3300, as described above with reference to the first push rod 2530 and the first coupling member 2380 included in the reposable device 2000. For example, as described above, the proximal end portion can include a protrusion or the like that can be configured to engage a protrusion included in a distal end portion of the first coupling member 3380. Thus, the first push rod 3530 of the cartridge assembly 3500 can be coupled to the first coupling member 3380 of the drive mechanism 3300 when the cartridge assembly 3500 is coupled to the handle 3100, as described in detail above with reference to the reposable device 2000.

As shown in FIGS. 52, 55, 57, and 59, the first push rod 3530 includes a set of push arms 3536 that are linearly arranged along a length of the first push rod 3530 with each push arm 3536 being disposed at a substantially uniform spacing from an adjacent push arm 3536. Each push arm 3536 includes an engagement surface 3537 that is configured to be placed in contact with a proximal surface of a different surgical clip 3590 included in the cartridge assembly 3500. As shown in FIG. 33, the set of push arms 3536 extend into and/or along the distal end portion 3535 of the first push rod 3530. In this manner, the engagement surfaces 3537 can contact a different surgical clip 3590 (e.g., temporarily retained by the spine 3520 and/or other portion of the cartridge assembly 3500) and can be moved within, for example, the first groove 3503 defined by the first member 3502 of the adapter 3501 and the first groove 3507 defined by the second member 3506 of the adapter 3501 to advance the surgical clips 3590 relative to the spine 3520 within the third groove 3505 defined by the first member 3502 and the third groove 3509 defined by the second member 3506, as described in further detail herein.

As described above, a portion of the second push rod 3540 of the cartridge assembly 3500 is disposed in the adapter 3501 and can be moved in an axial direction between a first position (e.g., a proximal position) and a second position (e.g., a distal position). As shown in FIGS. 49, 55, 57, and 59, the second push rod 3540 has a proximal end portion 3541 and a distal end portion 3545. The distal end portion 3545 is configured to extend through the second groove 3504 defined by the first member 3502 of the adapter 3501 and the second groove 3508 defined by the second member 3506 of the adapter to contact a portion of the clamp mechanism 3550, as described in further detail herein. The proximal end portion 3541 of the second push rod 3540 includes an adapter 3542. The adapter 3542 can be fixedly coupled to the proximal end portion 3541 via, for example, a weld, an adhesive, a friction fit, a press fit, and/or the like. As described above with reference to the second push rod 2540 of the cartridge assembly 2500, the adapter 3542 can include a protrusion or the like that can be configured to engage a protrusion included in a distal end portion of the second coupling member 3390. Thus, the second push rod 3540 of the cartridge assembly 3500 can be coupled to the second coupling member 3390 of the drive mechanism 3300 when the cartridge assembly 3500 is coupled to the handle 3100, as described in detail above with reference to the reposable device 2000.

The coupler 3518 of the cartridge assembly 3500 is configured to be fixedly disposed in the inner volume 3512 of the adapter 3501. The coupler 3518 defines an opening that is configured to receive, for example, the protrusion 3532 of the first push rod 3530 and the protrusion 3543 of the adapter 3542. More specifically, the protrusion 3532 of the first push rod 3530 and the protrusion 3543 of the adapter 3542 can be disposed in the opening 3519 such that the coupler 3518 is disposed about the notch 3533 defined by the protrusion 3532 of the first push rod 3530 and the notch 3544 defined by the protrusion 3543 of the adapter 3542.

The clamp mechanism 3550 of the cartridge assembly 3500 is coupled to a distal end portion of the adapter 3501 and is configured to sequentially receive the set of surgical clips 3590 (i.e., one after the other). The clamp mechanism 3550 includes a cinch member 3565, a first clamp member 3570, and a second clamp member 3580. A proximal end portion of the first clamp member 3570 included in the clamp mechanism 3550 is coupled to a distal end portion of the first member 3502 of the adapter 3501. More specifically, in some embodiments, the proximal end portion can be coupled to the first member 3502 of the adapter 3501 such that the first clamp member 3570 can be pivoted about the proximal end portion, as described in further detail herein. In other embodiments, the proximal end portion can be fixedly coupled to the first member 3502 of the adapter 3501 and, for example, a distal end portion 3573 of the first clamp member 3570 can be configured to bend, flex, and/or deform relative to the proximal end portion, as described in further detail herein. A distal end portion 3573 of the first clamp member 3570 can be, for example, substantially hollow and can be configured to sequentially receive the surgical clips 3590 (i.e., one after another). Similarly stated, the distal end portion 3573 defines a recess (not shown) that can selectively receive the surgical clips 3590, as described in further detail herein.

Similarly, a proximal end portion of the second clamp member 3580 included in the clamp mechanism 3550 is rotatably coupled to a distal end portion of the second member 3506 of the adapter 3501. More specifically, the proximal end portion can be coupled to the second member 3506 of the adapter 3501, as described above with reference to the first clamp member 3570. A distal end portion 3583 of the second clamp member 3580 can be, for example, substantially hollow and can be configured to sequentially receive the surgical clips 3590 (i.e., one after another). Similarly stated, the distal end portion 3583 defines a recess 3584 that can selectively receive the surgical clips 3590, as described in further detail herein.

The cinch member 3565 of the clamp mechanism 3550 can be any suitable shape and/or size. The cinch member 3565 is configured to be in contact with the distal end portion 3546 of the second push rod 3540. In this manner, movement of the second push rod 3540 in the distal direction and/or the proximal direction can move the cinch member 3565 is a similar and concurrent manner relative to the adapter 3501, as described in further detail herein. As described above with reference to the clamp mechanism 2550 included in the cartridge assembly 2500, the cinch member 3565 can define a notch that can movably receive the first clamp member 3570 and the second clamp member 3580. In this manner, the cinch member 3565 can be moved between a first position (e.g., a proximal position) and a second position (e.g., a distal position) relative to the first clamp member 3570 and the second clamp member 3580. Expanding further, the cinch member 3565 can be disposed about the first clamp member 3570 and the second clamp member 3580 such that movement of the cinch member 3565 can be configured to pivot, rotate, bend, flex, and/or deform at least a portion of the first clamp member 3570 and at least a portion of the second clamp member 3580 relative to the adapter 3501, as described in further detail herein.

The use and/or function of the reposable device 3000 is described herein with reference to FIGS. 53-60. More particularly, some aspects of the use and/or function of the reposable device 3000 can be substantially similar to corresponding aspects of the use and/or function of the reposable device 2000. Thus, a detailed description of the use and/or function of the reposable device 3000 is not discussed herein. Rather, a high level discussion of a method of use is provided. For example, in use, a user (e.g., a surgeon, a doctor, a physician, a technician, etc.) can engage the handle 3100 and the cartridge assembly 3500 to removably couple the cartridge assembly 3500 to the handle 3100, in a substantially similar manner as described in detail above with reference to the reposable device 2000. Thus, the first portion 3501A of the adapter 3501 can be inserted into the lock mechanism 3200 such that the protrusion 3511 is substantially aligned with the notch 3222.

Once the first portion 3501A of the adapter 3501 is inserted into the lock mechanism 3200, the user can rotate the cartridge assembly 3500 relative to the lock mechanism 3200. In this manner, the lock actuator 3230 can be moved such that a portion of the lock member 3250 is disposed in the recess 3510 defined by the adapter 3501, as shown in FIG. 53. Thus, the cartridge assembly 3500 can be removably coupled to the handle 3100 to place the reposable device 3000 in, for example, a second configuration, in a similar manner as described above with reference to the reposable device 2000 (see e.g., FIGS. 31-39). The rotation of the cartridge assembly 3500 is such that the first push rod 3530 and the second push rod 3540 are rotated relative to the first coupling member 3380 and the second coupling member 3390, respectively. Thus, the first push rod 3530 can be removably coupled to the first coupling member 3380 and the second push rod 3540 can be coupled to the second coupling member 3390, as described in detail above with reference to the reposable device 2000 (see e.g., FIGS. 37-39).

With cartridge assembly 3500 coupled to the lock mechanism 3200 and the drive mechanism 3300, the user, for example, can insert a portion of the cartridge assembly 3500 of the reposable device 3000 through an incision and/or orifice of the body of a patient. Once inserted into the body, the user can manipulate the reposable device 3000 such that, for example, the distal end portions 3573 and 3583 of the first clamp member 3570 and the second clamp member 3580, respectively, are disposed about a target tissue (e.g., a target vascular tissue to be ligated and/or occluded). With the cartridge assembly 3500 disposed in the desired location in the body, the user, for example, can manipulate the reposable device 3000 to rotate the actuator 3400 relative to the housing 3100, as described above with reference to the reposable device 2000 in FIG. 40. In this manner, the actuator 3400 can be rotated relative to the housing 3100 to transition the reposable device 3000 from the second configuration to a third configuration, as indicated by the arrow OO in FIG. 54.

With the actuator 3400 forming a kinematic link with a portion of the drive mechanism 3300, the pivoting and/or rotating motion of the actuator 3400 can exert a force that is sufficient to move at least a portion of the drive mechanism 3300 relative to the housing 3100 in a distal direction, as described above with reference to the reposable device 2000 in FIG. 40. As a result of the distal movement of the portion of the drive mechanism 3300, the first coupling member 3380 can be moved in the distal direction relative to the housing 3100 and/or the lock mechanism 3200, as indicated by the arrow PP in FIG. 54. Moreover, the first coupling member 3380 can be configured to move in the distal direction relative to the second coupling member 3390. Thus, with the first push rod 3530 of the cartridge assembly 3500 coupled to the first coupling member 3380 of the drive mechanism 3300, the distal movement of the movable portion 3335 moves the first push rod 3530 in the distal direction, as described in detail above with reference to the reposable device 2000 in FIG. 40.

Figure 55:
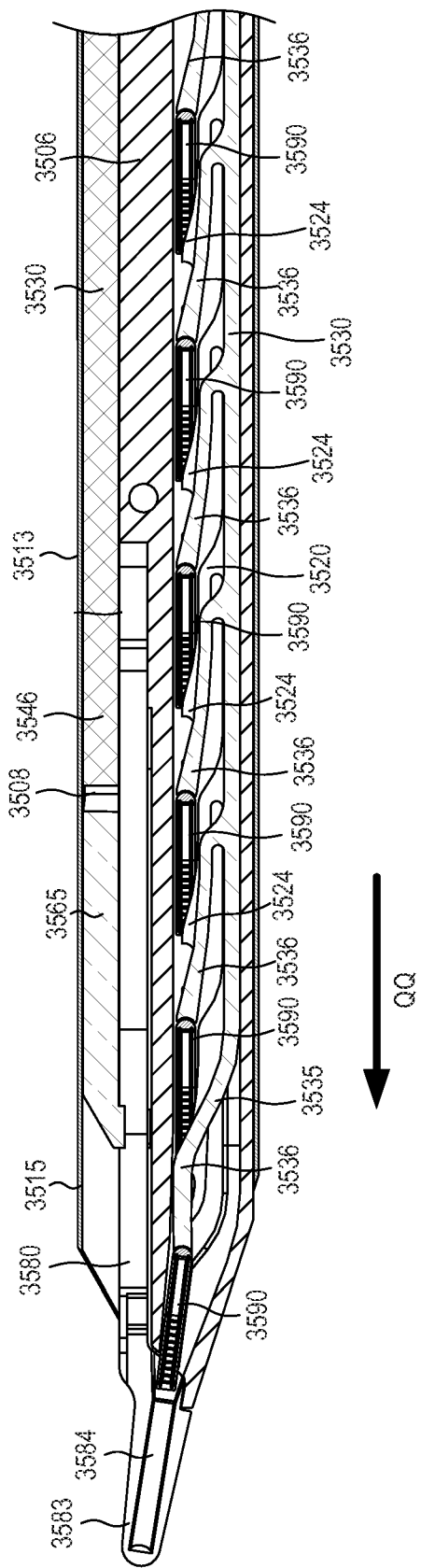
FIG. 55 is a cross-sectional view of a distal end portion of the cartridge assembly taken along the line $X_5$-$X_5$ in FIG. 47, in a first configuration.

In some instances, the distal movement of the first push rod 3530 can, for example, place the engagement surface 3537 of each push arm 3536 in contact with a different surgical clip 3590 retained by a corresponding clip retainer 3524 of the spine 3520, as indicated by the arrow QQ in FIG. 55, thereby transitioning the cartridge assembly 3500 from a first configuration to a second configuration. More particularly, the distal movement of the first coupling member 3380 of the drive mechanism 3300 can result in a distal movement of the first push rod 3530 in the first groove 3503 defined by the first member 3502 of the adapter 3501 and the first groove 3507 defined by the second member 3506 of the adapter 3501. In some instances, the distal movement of the first push rod 3530 can be sufficient to collectively move the surgical clips 3590 within the third grooves 3505 and 3509 defined by the first member 3502 and the second member 3506, respectively, of the adapter 3501. Thus, the set of surgical clips 3590 can be collectively moved in the distal direction relative to the clip retainers 3524 and/or the clamp mechanism 3550, as described above with reference to the cartridge assembly 2500 in FIG. 41.

Figure 56:
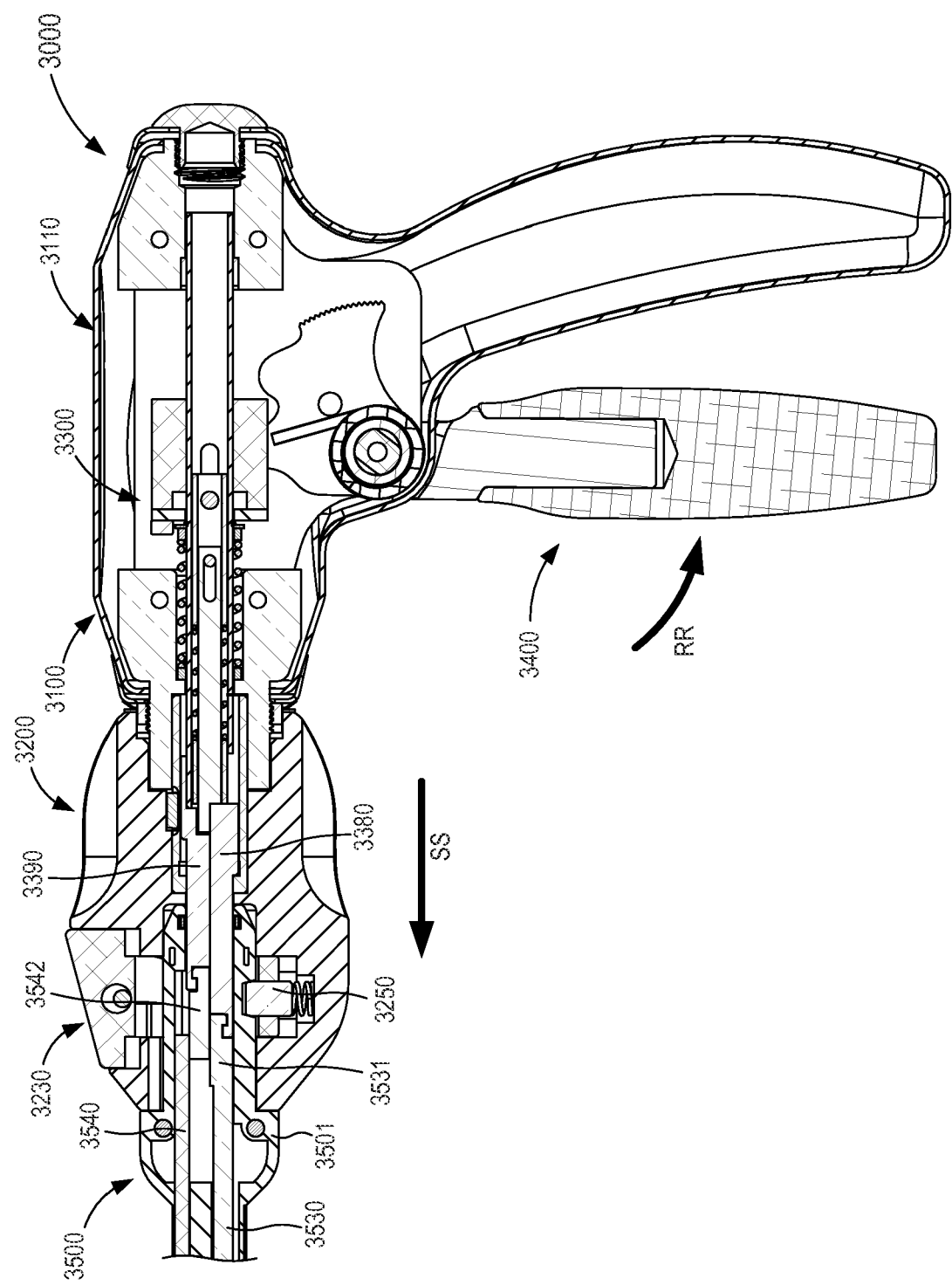
FIG. 56 is a cross-sectional view of the portion of the reposable device taken along the line $X_5$-$X_5$ in FIG. 47, in a fourth configuration.

In some instances, the user can continue to exert a pressure to rotate the actuator 3400 relative to the housing 3100 to transition the reposable device 3000 from the third configuration to a fourth configuration, as indicated by the arrow RR in FIG. 56. In this manner, a portion of the drive mechanism 3300 can be moved in the distal direction relative to the housing 3100 to transition the drive mechanism 3300 from its second configuration to a third configuration. For example, as described in detail above with reference to the drive mechanism 2300 in FIG. 42, the distal movement of the portion of the drive mechanism 3300 results in a distal movement of the second coupling member 3390 relative to the housing 3100 and/or the lock mechanism 3200, as indicated by the arrow SS in FIG. 56. Similarly, the first coupling member 3380 can be further moved in the distal direction. In this manner, the first coupling member 3380 and the second coupling member 3390 can be moved with a substantially similar velocity and in a substantially concurrent motion, as described in detail above with reference to the drive mechanism 2300 in FIG. 42.

Figure 57:
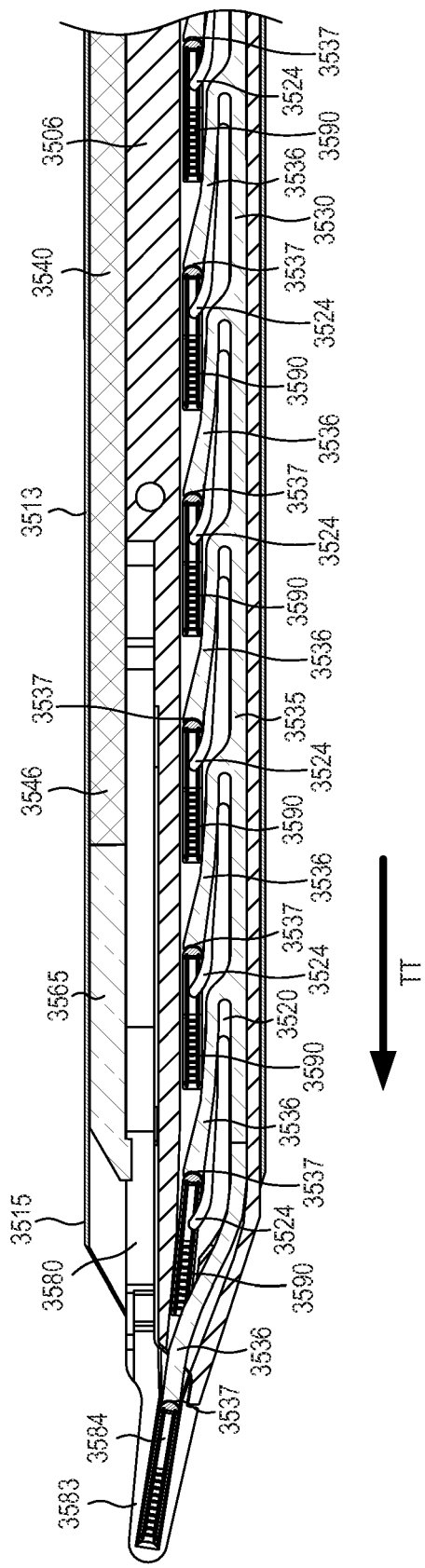
FIG. 57 is a cross-sectional view of the distal end portion of the cartridge assembly taken along the line $X_5$-$X_5$ in FIG. 47, in a second configuration.

With the first push rod 3530 of the cartridge assembly 3500 coupled to the first coupling member 3380 of the drive mechanism 3300, the distal movement of the movable portion 3335 moves the first push rod 3530 in the distal direction, as described above. Similarly, with the second push rod 3540 of the cartridge assembly 3500 coupled to the second coupling member 3390 of the drive mechanism 3300 (as described above), the distal movement of the second coupling member 3390 also moves the second push rod 3540 in the distal direction to transition the cartridge assembly 3500 from its second configuration to a third configuration, as shown in FIG. 57. More particularly, the first push rod 3530 can be moved within the first groove 3503 defined by the first member 3502 of the adapter 3501 and the first groove 3507 defined by the second member 3506 of the adapter 3501 to collectively move the set surgical clips 3590 within the third grooves 3505 and 3509 defined by the first member 3502 and the second member 3506, respectively, of the adapter 3501, as indicated by the arrow TT FIG. 57. Thus, the set of surgical clips 3590 can be collectively moved in the distal direction relative to the clip retainers 3524 and/or the clamp mechanism 3550, as described above with reference to the cartridge assembly 2500 in FIG. 43. Moreover, the distal most surgical clip 3590 and the surgical clip 3590 adjacent thereto can be advanced in the distal direction relative to the clamp mechanism 3550. That is to say, the first push rod 3530 can advance the distal most surgical clip 3590 and the surgical clip 3590 adjacent thereto in the distal direction beyond the set of clip retainers 3524 included in the spine 3520 to be disposed in and/or retained by the clamp mechanism 3550. As described in detail above with reference to the cartridge assembly 2500 in FIG. 43, the first push rod 3530 can advance the distal most surgical clip 3590 such that the distal most surgical clip 3590 is disposed in the space defined between the distal end portion 3573 of the first clamp member 3570 and the distal end portion 3583 of the second clamp member 3580.

With the second push rod 3540 in contact with the cinch member 3565, the distal movement of the second push rod 3540 results in a distal movement of the cinch member 3565 relative to the first clamp member 3570 (not shown in FIG. 57) and the second clamp member 3580. Thus, as described in detail above with reference to the clamp mechanism 2550, at least a portion of the first clamp member 3570 and at least a portion of the second clamp member 3580 can be pivoted relative to the first member 3502 of the adapter 3501 and the second member 3506 of the adapter 3501, respectively. In other embodiments, at least a portion of the first clamp member 3570 and at least a portion of the second clamp member 3580 can be bent, flexed, and/or otherwise deformed relative to the first member 3502 of the adapter 3501 and the second member 3506 of the adapter 3501, respectively. In this manner, as the distal most surgical clip 3590 is advanced into the space defined between a recess (not shown) of the first clamp member 3570 and the recess 3584 of the second clamp member 3580, the cinch member 3565 can decrease the space therebetween such the recess of the first clamp member (not shown) and the recess 3584 of the second clamp member 3580 are brought into contact with opposite sides of the surgical clip 3590, thereby retaining the surgical clip 3590 in a relatively fixed position.

Figure 58:
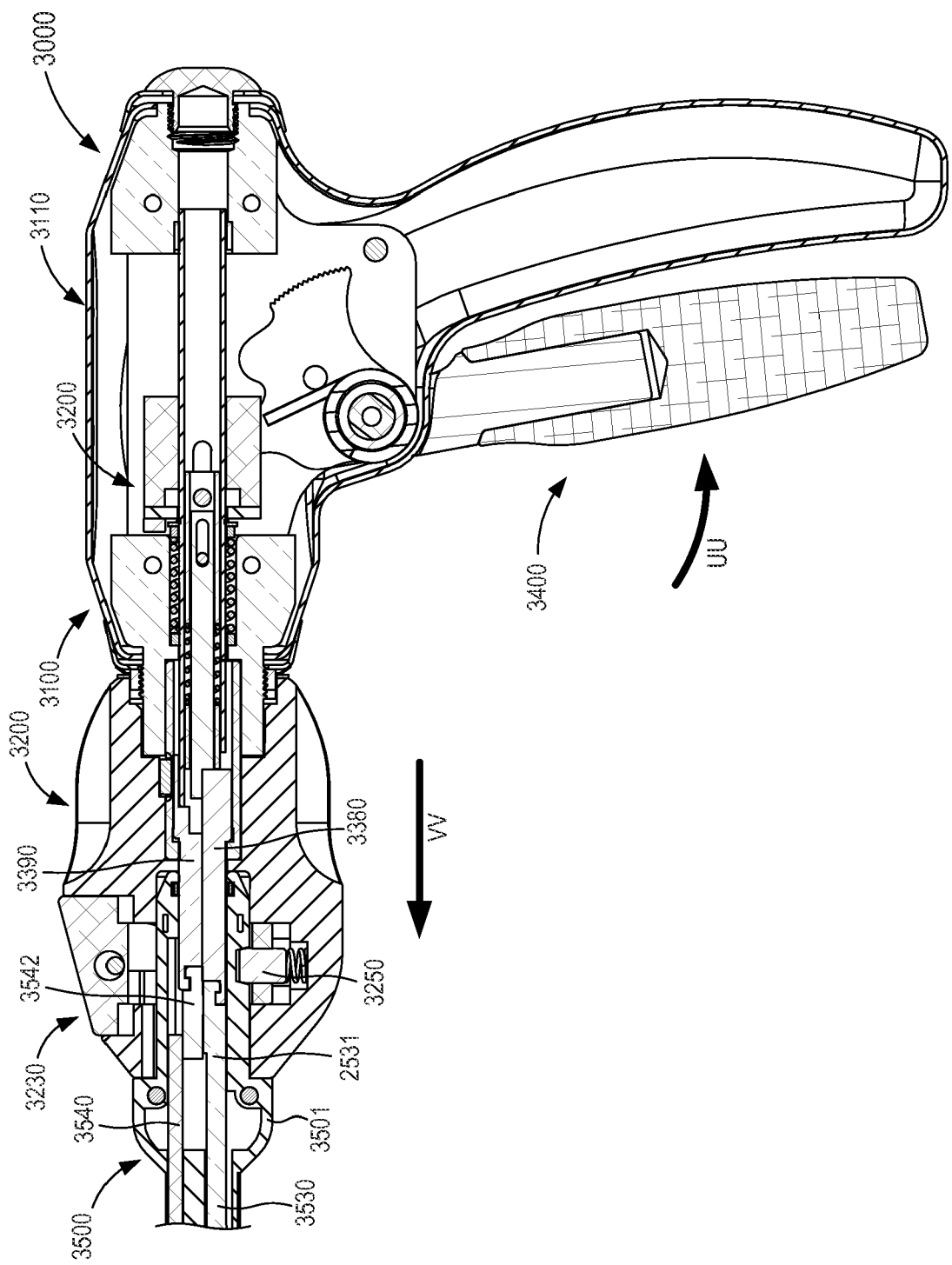
FIG. 58 is a cross-sectional view of the portion of the reposable device taken along the line $X_5$-$X_5$ in FIG. 47, in a fifth configuration.
Figure 59:
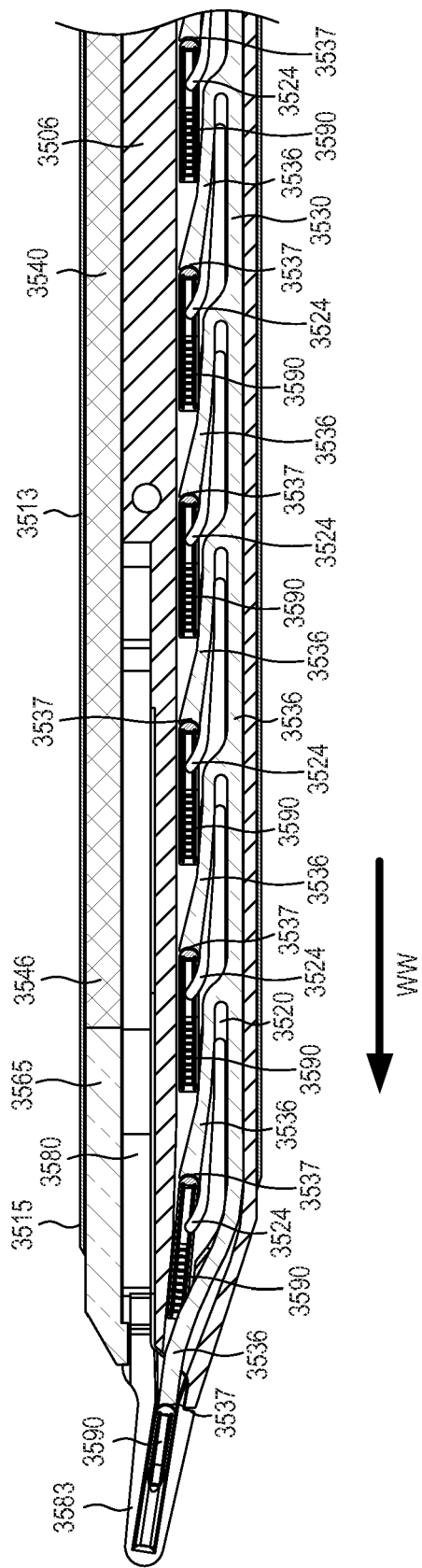
FIG. 59 is a cross-sectional view of the distal end portion of the cartridge assembly taken along the line $X_5$-$X_5$ in FIG. 47, in a third configuration.
Figure 60:
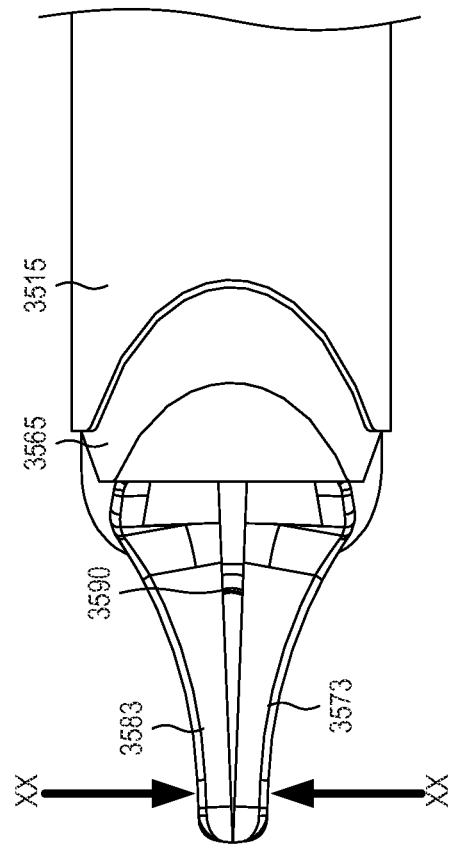
FIG. 60 is a top view of a distal end portion of the cartridge assembly of FIG. 47 in the third configuration.

In some instances, the user can continue to exert a force on the actuator 3400 to rotate the actuator 3400 relative to the housing 3100 to transition the reposable device 3000 from the fourth configuration to a fifth configuration, as indicated by the arrow UU in FIG. 58. In this manner, the actuator 3400 can move a portion of the drive mechanism 3300 in a similar manner as described above to transition the drive mechanism 3300 from its third configuration to a fourth configuration, as indicated by the arrow VV in FIG. 58. For example, as described above with reference to the drive mechanism 2300 in FIG. 44, the distal movement of the portion of the drive mechanism 3300 can result in a distal movement of the second coupling member 3390 relative to the first coupling member 3380. More specifically, the first coupling member 3380 can be placed in a distal position that is associated with an extent of travel in the distal direction. Thus, the first push rod 3530 of the cartridge assembly 3500 can be maintained in a substantially fixed position and the second push rod 3540 of the cartridge assembly 3500 can be moved in the distal direction relative to the first push rod 3530 to transition the cartridge assembly 3500 from its third configuration to a fourth configuration. Thus, as indicated by the arrow WW in FIG. 59, the distal movement of the second push rod 3540 (i.e., within the second grooves 3504 and 3508 defined by the first member 3502 and the second member 3506, respectively, of the adapter 3501 can result in a distal movement of the cinch member 3565 relative to the first clamp member 3570 and the second clamp member 3580 (not shown). More specifically, the cinch member 3565 can move along a length of the first clamp member 3570 and a corresponding length of the second clamp member 3580 to be disposed in its distal position, as shown in FIG. 59. As the cinch member 3565 is moved in the distal direction relative to the clamp members 3570 and 3580, the first clamp member 3570 and the second clamp member 3580 are pivoted, bent, flexed, and/or otherwise deformed relative to the adapter 3501 (as described above) such that the space defined between the distal end portions 3573 and 3583, respectively is reduced. Hence, with the recess of the first clamp member (not shown) in contact with a first side of the surgical clip 3590 and the recess 3584 of the second clamp member 3580 in contact with a second, opposite side of the surgical clip 3590, the space between the distal end portions 3573 and 3583 of the clamp members 3570 and 3580, respectively, can be reduced to an extent that the surgical clip 3590 is clamped, deformed, closed, bent, and/or otherwise reconfigured, as indicated by the opposing arrows XX in FIG. 60. Moreover, with the cartridge assembly 3500 positioned within the body such that the clamp members 3570 and 3580 are disposed about, for example, the target vascular tissue, the clamping and/or otherwise reconfiguring of the surgical clip 3590 can secure the surgical clip 3590 to the target vascular structure to ligate and/or occlude that target vascular structure.

Once the surgical clip 3590 is disposed about the desired vascular structure, in some instances, the user can, for example, reduce and/or remove the force exerted on the actuator 3400 and as such, the reposable device 3000 can be transitioned from its fifth configuration (e.g., FIGS. 58-60) to its second configuration (e.g., FIG. 53) in a substantially similar manner as described above with reference to the reposable device 2000. In some instances, the user can manipulate the reposable device 3000 to reposition the cartridge assembly 3500 in the body such that the distal end portion 3573 of the first clamp member 3570 and the distal end portion 3583 of the second clamp member 3580 is disposed about a different vascular structure (or the same vascular structure at a different location along that vascular structure). Thus, the user can manipulate the reposable device 3000 to ligate and/or occlude that vascular structure in the manner described above with reference to FIGS. 54-60. Once the target vascular structures have been ligated and/or occluded and/or after the surgical procedure (e.g., a laparoscopic procedure, an endoscopic procedure, and/or the like) is completed, the user can remove the cartridge assembly 3500 from the body and can manipulate the reposable device 3000 to decouple the cartridge assembly 3500 from the handle 3100. In some instances, the cartridge assembly 3500 can be safely discarded, while the handle 3100 can be reused.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

By way of example, although the actuator 2400 is shown and described above with reference to FIGS. 17 and 18 as including the return portion 2445 having one cam follower 2446 configured to move along a surface of the rack portion 2437 of the second cam 2435, in other embodiments, an actuator can include a return portion having, for example, two cam followers. Such a return portion can include, for example, a first cam follower configured to move along a surface of a first cam and a second cam follower configured to move along a surface of a second cam.

By way of another example, although the springs, bias members, and/or the like have been particularly shown and described above, in other embodiments, any of the springs, bias members, and/or the like can be, for example, any suitable energy storage member or the like. More specifically, any spring and/or bias member configured to be placed in compression can be arranged to be placed in tension, while functioning in a substantially similar manner as described above. Conversely, any spring and/or bias member configured to be placed in tension can be arranged to be placed in compression, while functioning in a substantially similar manner as described above. In some embodiments, any spring and/or bias member described above as being, for example, a torsion spring can, in other embodiments, be arranged in as, for example, a linear spring, while functioning in a substantially similar manner as described above.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above. For example, although the rotation of the actuators 2400 and 3400 relative to the housings 2100 and 3100, respectively, was shown and described as being, for example, performed in a sequence of discrete events, in other instances, the user can continuously exert a force on the actuators 2400 and 3400 such that the actuators 2400 and 3400 are continuously rotated relative to the housings 2100 and 3100, respectively.

What is claimed:

1. An apparatus, comprising:
   a housing;
   a drive mechanism movably disposed in the housing, the drive mechanism having a fixed support structure and a movable portion, the movable portion including a shuttle, a first actuating tube and a second actuating tube, the shuttle configured to move distally along the first actuating tube relative to the fixed support structure;
   wherein the second actuating tube is movably received within the first actuating tube;
   a single actuator operably coupled to the shuttle of the drive mechanism, the actuator configured to be moved between a first position relative to the housing and a second position relative to the housing to move the shuttle between a first configuration and a second configuration, the shuttle moving the first actuating tube and the second actuating tube distally as the shuttle is moved into the first configuration and the second configuration; and
   a cartridge assembly removably coupled to the housing, the cartridge assembly including a first push rod, a second push rod, and a clamp mechanism, the clamp mechanism comprising a fixed shoe having a recess and a cinch member, the recess configured to receive a first arm and a second arm therein, and the cinch member movable relative to the shoe over the first arm and the second arm;
   the first push rod of the cartridge assembly removably coupled to the first actuating tube such that the moving of the first actuating tube distally moves the first push rod of the cartridge assembly relative to the clamp mechanism to advance a surgical clip included in the cartridge assembly in a distal direction, the second push rod of the cartridge assembly removably coupled to the second actuating tube such that the moving of the second actuating tube distally moves the second push rod of the cartridge assembly, which directly contacts the cinch member of the clamp mechanism, and moves the cinch member in the distal direction the cinch member configured to clamp the surgical clip with the first and second arms when moved in the distal direction.

2. The apparatus of claim 1, wherein the cartridge assembly is one of a 5 millimeter surgical clip cartridge or a 10 millimeter surgical clip cartridge.

3. The apparatus of claim 1, wherein the cartridge assembly is disposable.

4. The apparatus of claim 1, wherein the actuator is coupled to the housing and rotatable between the first position relative to the housing to the second position relative to the housing, the actuator including a cam configured to move the shuttle between the first configuration and the second configuration.

5. The apparatus of claim 1, further comprising:
   a lock mechanism having a body comprising a lock actuator, the body coupled to the housing, a portion of the cartridge assembly configured to be inserted into an inner volume of the body of the lock mechanism when the cartridge assembly is in a first orientation relative to the lock mechanism, the cartridge assembly configured to be rotated to a second orientation relative to the lock mechanism when the portion of the cartridge assembly is disposed in the inner volume, the lock mechanism configured to at least temporarily maintain the cartridge assembly in the second orientation.

6. The apparatus of claim 5, wherein the lock actuator is configured to be transitioned between a first lock actuator configuration and a second lock actuator configuration, the cartridge assembly configured to be inserted into the inner volume of the body of the lock mechanism when the lock actuator is in the first lock actuator configuration, the lock actuator configured to maintain the cartridge assembly in the second orientation when the lock actuator is in the second lock actuator configuration.

7. The apparatus of claim 1, further comprising:
   a lock mechanism having a body comprising a lock actuator, the body coupled to the housing such that a portion of the first actuating tube and a portion of the second actuating tube are configured to extend into an inner volume defined by the body of the lock mechanism, the cartridge assembly configured to be inserted into the inner volume of the body of the lock mechanism such that the first push rod of the cartridge assembly is removably coupled to the first actuating tube, and the second push rod of the cartridge assembly is removably coupled to the second actuating tube.

8. The apparatus of claim 1, wherein the cartridge assembly comprises a spine, the spine including a set of clip retainers, each clip retainer included in the set of clip retainers configured to temporarily retain a different surgical clip of a set of surgical clips.

9. The apparatus of claim 8, wherein the first push rod of the cartridge assembly configured to move relative to the spine to advance the set of surgical clips in the distal direction relative to the spine such that each surgical clip included in the set of surgical clips is moved in the distal direction from a clip retainer included in the set clip retainers to an adjacent clip retainer included in the set of clip retainers, a distal most surgical clip included in the set of surgical clips being moved in the distal direction from a distal most clip retainer included in the set of clip retainers to the clamp mechanism.

10. The apparatus of claim 1, wherein at least the actuator or the drive mechanism includes a bias member configured to move the actuator from the second position relative to the housing to the first position relative to the housing and configured to transition the shuttle from the second configuration to the first configuration.

11. An apparatus, comprising:
    a housing;
    a drive mechanism movably disposed in the housing, the drive mechanism having a fixed support structure and a movable portion, the movable portion including a shuttle, a first actuating tube and a second actuating tube, the shuttle configured to move distally along the first actuating tube relative to the fixed support structure;
    a lock mechanism including a body having an opening extending along a first axial centerline therethrough and a lock actuator, the body coupled to the housing such that a portion of the first actuating tube and a portion of the second actuating tube extend into an inner volume defined by the opening, and the lock actuator comprising a second opening extending along a second axial centerline, which is parallel to the first axial centerline, the second opening configured to receive a lock member and the lock actuator configured to be transitioned between a first configuration and a second configuration relative to the lock member, such that movement of the lock actuator is in a direction that traverses the first axial centerline, which moves the second axial centerline into and out of alignment with the first axial centerline; and a cartridge assembly, a portion of the cartridge assembly configured to be inserted into the inner volume of the lock mechanism when the cartridge assembly is in a first orientation relative to the lock mechanism and when the lock actuator is in the first configuration, the cartridge assembly configured to be moved to a second orientation relative to the lock mechanism when the portion of the cartridge assembly is disposed in the inner volume such that a first push rod of the cartridge assembly is removably coupled to the first actuating tube and a second push rod of the cartridge assembly is removably coupled to the second actuating tube, the lock actuator configured to be moved to the second configuration to at least temporarily maintain the cartridge assembly in the second orientation.

12. The apparatus of claim 11, wherein the first actuating tube defines a notch and the second actuating tube defines a notch, the cartridge assembly configured to be rotated from the first orientation to the second orientation such that a portion of the first push rod of the cartridge assembly is disposed in the notch of the first actuating tube and such that a portion of the second push rod of the cartridge assembly is disposed in the notch of the second actuating tube.

13. The apparatus of claim 11, further comprising:
an actuator operably coupled to the shuttle of the drive mechanism, the actuator configured to be actuated to move the shuttle between a first shuttle configuration and a second shuttle configuration,
the first push rod of the cartridge assembly removably coupled to the first actuating tube such that movement of the first actuating tube into a first actuating tube configuration, moves the first push rod of the cartridge assembly to advance a surgical clip included in the cartridge assembly in a distal direction, the second push rod of the cartridge assembly removably coupled to the second actuating tube such that movement of the second actuating tube into a second actuating tube configuration, moves the second push rod of the cartridge assembly, which directly contacts a cinch member of a clamp mechanism included in the cartridge assembly, from a first cinch member configuration to a second cinch member configuration, the cinch member configured to clamp the surgical clip when in the second cinch member configuration.

14. The apparatus of claim 11, wherein the cartridge assembly includes an adapter configured to be at least partially disposed in the inner volume of the lock mechanism, the adapter including a protrusion such that when the cartridge assembly is in the first orientation relative to the lock mechanism, the protrusion is substantially aligned with a notch defined by an inner surface of the lock mechanism.

15. The apparatus of claim 11, wherein the lock actuator includes an inner surface defining the second opening, the cartridge assembly including an adapter configured to be inserted through the second opening defined by the lock actuator.

16. The apparatus of claim 15, wherein the lock actuator includes a lock member and defines a channel, the lock member being in a first position relative to the inner surface of the lock actuator when the cartridge assembly is in the first orientation and the adapter is inserted into the opening defined by the lock actuator, a protrusion of the adapter configured to move in the channel defined by the lock actuator when the cartridge assembly is moved to the second orientation, the lock member being moved to a second position relative to the inner surface when the lock actuator is moved to the second configuration such that at least a portion of the lock member is disposed in a recess defined by the adapter.

17. An apparatus, comprising:
a drive mechanism disposed in a housing and movable between a first configuration and a second configuration, the drive mechanism including a fixed support structure and a movable shuttle configured to movably receive a first actuating tube such that the shuttle is movably disposed about the first actuating tube, the first actuating tube having a lumen to movably receive a second actuating tube;
wherein the shuttle is configured to move distally along the first actuating tube relative to the fixed support structure;
the first actuating tube configured to be moved between a first axial position relative to the fixed support structure of the drive mechanism and a second axial position relative to the fixed support structure of the drive mechanism as the shuttle moves distally, the second actuating tube configured to move between the first axial position and the second axial position as the shuttle moves distally, at least a portion of the movement of the first actuating tube being independent of at least a portion of the movement of the second actuating tube; and
a cartridge assembly removably coupled to the housing, the cartridge assembly including a first push rod and a second push rod, the first push rod of the cartridge assembly in contact with the first actuating tube of the drive mechanism when the cartridge assembly is coupled to the housing such that movement of the first actuating tube moves the first push rod of the cartridge assembly from a first push rod axial position relative to the cartridge assembly to a second push rod axial position relative to the cartridge assembly to advance a surgical clip included in the cartridge assembly in a distal direction, and the second push rod of the cartridge assembly selectively placed in contact with the second actuating tube when the cartridge assembly is coupled to the housing, such that when in contact, the second push rod is configured to move a cinch member of the cartridge assembly in the distal direction to clamp the surgical clip.

18. The apparatus of claim 17, wherein the first actuating tube defines a notch and the second actuating tube defines a notch, the cartridge assembly configured to be coupled to the housing such that a portion of the first push rod of the cartridge assembly is disposed in the notch of the first actuating tube and such that a portion of the second push rod of the cartridge assembly is disposed in the notch of the second actuating tube.

19. The apparatus of claim 18, wherein a surface defining the notch of the first actuating tube has a radius, a surface defining the notch of the second actuating tube has the radius.

20. The apparatus of claim 17, wherein the housing includes a lock mechanism having a body comprising a lock actuator, the body of the lock mechanism defining an inner volume, a portion of the cartridge assembly is configured to be inserted into the inner volume of the body of the lock mechanism when the cartridge assembly has a first orientation relative to the drive mechanism, the cartridge assembly being rotated to a second orientation relative to the drive mechanism to couple the cartridge assembly to the housing.

* * * * *

UNITED STATES PATENT AND TRADEMARK OFFICE
CERTIFICATE OF CORRECTION

| | | |
|---|---|---|
| PATENT NO. | : 10,792,041 B2 | Page 1 of 1 |
| APPLICATION NO. | : 14/593481 | |
| DATED | : October 6, 2020 | |
| INVENTOR(S) | : Menn et al. | |

It is certified that error appears in the above-identified patent and that said Letters Patent is hereby corrected as shown below:

In the Claims

Column 46, Line 35. please place the word "of" between "set" and "clip"

Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*